United States Patent
Kato et al.

(10) Patent No.: US 9,196,842 B2
(45) Date of Patent: Nov. 24, 2015

(54) AROMATIC AMINE DERIVATIVE AND ORGANIC ELECTROLUMINESCENT ELEMENT

(71) Applicants: IDEMITSU KOSAN CO., LTD., Chiyoda-ku (JP); MITSUI CHEMICALS, INC., Minato-ku (JP)

(72) Inventors: Tomoki Kato, Ichihara (JP); Takayasu Sado, Urayasu (JP); Takahiro Fujiyama, Kisarazu (JP)

(73) Assignees: IDEMITSU KOSAN CO., LTD., Chiyoda-ku (JP); MITSUI CHEMICALS, INC., Minato-ku (JP)

( * ) Notice: Subject to any disclaimer, the term of this patent is extended or adjusted under 35 U.S.C. 154(b) by 0 days.

(21) Appl. No.: 14/410,949

(22) PCT Filed: Jun. 20, 2013

(86) PCT No.: PCT/JP2013/066988
§ 371 (c)(1),
(2) Date: Dec. 23, 2014

(87) PCT Pub. No.: WO2014/002873
PCT Pub. Date: Jan. 3, 2014

(65) Prior Publication Data
US 2015/0287931 A1 Oct. 8, 2015

(30) Foreign Application Priority Data
Jun. 29, 2012 (JP) .................. 2012/147167

(51) Int. Cl.
*H01L 51/00* (2006.01)
*C07D 307/91* (2006.01)
(Continued)

(52) U.S. Cl.
CPC .......... *H01L 51/0061* (2013.01); *C07D 307/77* (2013.01); *C07D 307/91* (2013.01);
(Continued)

(58) Field of Classification Search
CPC ........... H01L 51/0061; H01L 51/0073; G09G 3/3208
See application file for complete search history.

(56) References Cited

U.S. PATENT DOCUMENTS

| 4,720,432 A | 1/1988 | VanSlyke et al. |
| 5,061,569 A | 10/1991 | VanSlyke et al. |

(Continued)

FOREIGN PATENT DOCUMENTS

| JP | 11 111460 | 4/1999 |
| JP | 2005 112765 | 4/2005 |

(Continued)

OTHER PUBLICATIONS

International Search Report Issued Jul. 23, 2013 in PCT/JP13/066988 Filed Jun. 20, 2013.

*Primary Examiner* — Yu-Hsi D Sun
*Assistant Examiner* — Ankush Singal
(74) *Attorney, Agent, or Firm* — Oblon, McClelland, Maier & Neustadt, L.L.P.

(57) ABSTRACT

An organic electroluminescence device having a long lifetime and a higher emission efficiency and a specific aromatic amine derivative which provides such an organic electroluminescence device are provided. In the specific aromatic amine derivative, a dibenzofuranyl group or a dibenzothiophenyl group is bonded via a p-phenylene and a heteroaryl group is bonded via a m-phenylene. The organic electroluminescence device includes a cathode, an anode and an organic thin film layer including one or more layers which is disposed between the cathode and the anode. The organic thin film layer includes at least one light emitting layer and at least one layer of the organic thin film layer includes the aromatic amine derivative singly or in combination.

13 Claims, 1 Drawing Sheet

(51) Int. Cl.
    *C07D 409/12*     (2006.01)
    *C07D 405/12*     (2006.01)
    *C07D 409/14*     (2006.01)
    *C07D 405/14*     (2006.01)
    *C07F 7/08*     (2006.01)
    *C07D 307/77*     (2006.01)
    *H01L 51/52*     (2006.01)
    *H01L 51/50*     (2006.01)

(52) U.S. Cl.
    CPC ............ *C07D405/12* (2013.01); *C07D 405/14* (2013.01); *C07D 409/12* (2013.01); *C07D 409/14* (2013.01); *C07F 7/0812* (2013.01); *H01L 51/006* (2013.01); *H01L 51/0094* (2013.01); *H01L 51/0052* (2013.01); *H01L 51/0054* (2013.01); *H01L 51/0073* (2013.01); *H01L 51/0074* (2013.01); *H01L 51/5012* (2013.01); *H01L 51/5016* (2013.01); *H01L 51/5056* (2013.01); *H01L 51/5206* (2013.01); *H01L 51/5221* (2013.01)

(56) References Cited

U.S. PATENT DOCUMENTS

| | | | | |
|---|---|---|---|---|
| 2007/0287029 | A1* | 12/2007 | Kawamura et al. | 428/704 |
| 2008/0106190 | A1* | 5/2008 | Yabunouchi et al. | 313/504 |
| 2009/0066225 | A1* | 3/2009 | Kimura et al. | 313/504 |
| 2009/0309488 | A1* | 12/2009 | Kato et al. | 313/504 |
| 2010/0201259 | A1* | 8/2010 | Kobayashi | 313/504 |
| 2011/0278551 | A1 | 11/2011 | Yabunouchi et al. | |
| 2012/0074395 | A1 | 3/2012 | Yabunouchi et al. | |
| 2013/0105771 | A1 | 5/2013 | Ryu et al. | |

FOREIGN PATENT DOCUMENTS

| | | |
|---|---|---|
| JP | 2006 151844 | 6/2006 |
| JP | 2008 21687 | 1/2008 |
| WO | 2006 122630 | 11/2006 |
| WO | 2006 128800 | 12/2006 |
| WO | 2007 125714 | 11/2007 |
| WO | 2009 145016 | 12/2009 |
| WO | 2010 061824 | 6/2010 |
| WO | 2010 114017 | 10/2010 |
| WO | 2011 133007 | 10/2011 |

* cited by examiner

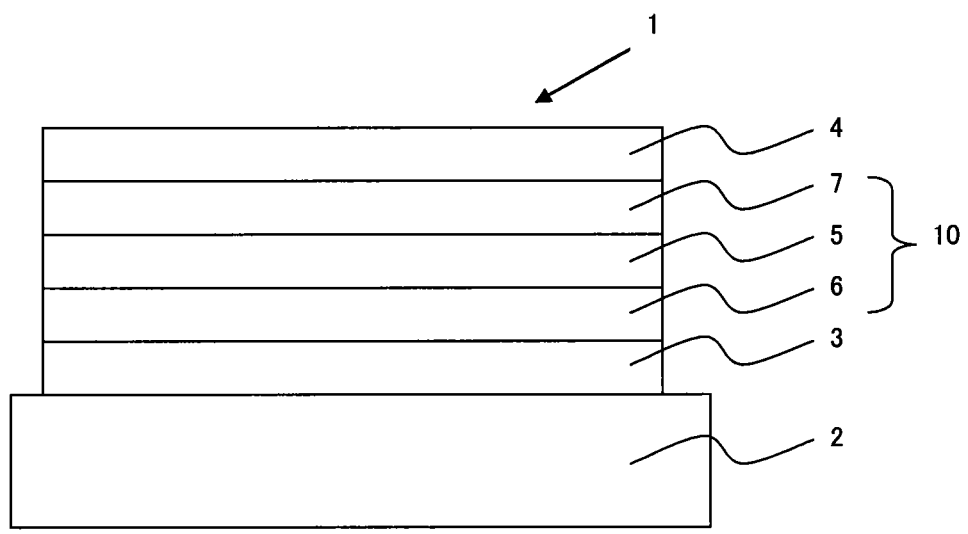

AROMATIC AMINE DERIVATIVE AND ORGANIC ELECTROLUMINESCENT ELEMENT

TECHNICAL FIELD

The present invention relates to aromatic amine derivatives and organic electroluminescence (organic EL) devices employing the aromatic amine derivatives.

BACKGROUND ART

An organic EL device is a spontaneous light emitting device which utilizes a principle that a fluorescent substance emits the light by the energy due to recombination of holes injected from an anode and electrons injected from a cathode when an electric field is applied. Since an organic EL device of laminate type capable of driving at low voltage has been reported by C. W. Tang et al. of Eastman Kodak Company (C. W. Tang and S. A. Vanslyke, Applied Physics Letters, Volume 51, Page 913, 1987, or the like), many studies have been conducted for an organic EL device which comprises an organic material. Tang et al. used a light emitting layer of tris(8-quinolinolato)aluminum and a hole transport layer of a triphenyldiamine derivative. Advantages of the laminate structure are that the efficiency of hole injection into the light emitting layer can be increased, that the efficiency of forming excitons by recombination can be increased by blocking electrons injected from the cathode, and that excitons formed can be confined in the light emitting layer. As the structure of organic EL devices, a two-layered structure having a hole transporting (injecting) layer and an electron transporting light emitting layer and a three-layered structure having a hole transporting (injecting) layer, a light emitting layer and an electron transporting (injecting) layer are well known. To increase the efficiency of recombination of injected holes and electrons in laminated devices, the structure of the device and the process for forming the device have been studied.

In general, when an organic EL device is driven or stored in high-temperature environment, adverse effects, such as, a change in the luminescent color, a decrease in current efficiency, an increase in driving voltage, and a decrease in a lifetime of light emission, are caused. In order to prevent the adverse effects, it has been necessary to increase the glass transition temperature (Tg) of the hole transporting material. Therefore, a hole transporting material having many aromatic groups, preferably 8 to 12 benzene rings in its molecule has been used (for example, an aromatic diamine derivative of Patent Document 1 and a fused aromatic diamine derivative of Patent Document 2).

However, a hole transporting material, such as, a highly symmetric compound and a highly planar compound each comprising a large number of aromatic groups in its molecule, easily crystallizes when made into a thin film during the production of organic EL device, thereby causing a problem of reducing the yields of organic EL device because the outlet of a crucible used in vapor deposition is clogged and a problem of a defective thin film due to crystallization. In addition, a compound comprising a large number of aromatic groups in its molecule generally has a high glass transition temperature (Tg), but has a high sublimation temperature. Therefore, it decomposes during vapor deposition and is deposited into a nonuniform film to reduce the lifetime.

Patent Documents 3 to 5 report diamine compounds comprising a central dibenzofuran skeleton. Patent Documents 6 to 10 report compounds in which a dibenzofuran is bonded to a monoamine via an aryl group. However, the performance of the proposed compounds as the materials of organic EL devices is insufficient.

As described above, the efficiency and lifetime of the reported organic EL devices are not sufficient, and therefore, the development of an organic EL device having more excellent performance has been strongly demanded.

CITATION LIST

Patent Documents

Patent Document 1: U.S. Pat. No. 4,720,432
Patent Document 2: U.S. Pat. No. 5,061,569
Patent Document 3: JP 2005-112765A
Patent Document 4: JP 11-111460A
Patent Document 5: WO 2006/122630
Patent Document 6: WO 2006/128800
Patent Document 7: JP 2006-151844A
Patent Document 8: JP 2008-021687A
Patent Document 9: WO 2007/125714
Patent Document 10: WO 2009/145016

SUMMARY OF THE INVENTION

Problems to be Solved by the Invention

The present invention has been made to solve the above problems and an object of the invention is to provide an organic electroluminescence device having a long lifetime and a higher emission efficiency and provide an aromatic amine derivative which realizes such an organic electroluminescence device.

Means for Solving the Problems

As a result of extensive research for achieving the above object, the inventors have found that a specific aromatic amine derivative in which a dibenzofuranyl group or a dibenzothiophenyl group is bonded via a p-phenylene and a heteroaryl group is bonded via a m-phenylene solves the above problems. The present invention is based on this finding.

The present invention provides:
1. an aromatic amine derivative represented by formula (1):

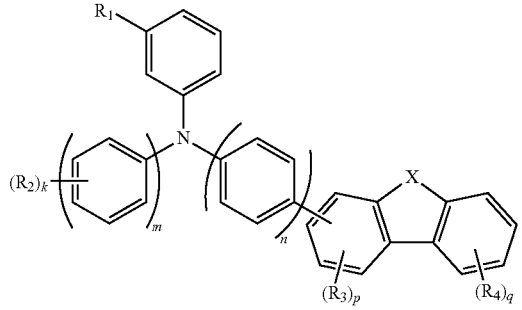

wherein:
$R_1$ represents a substituted or unsubstituted heteroaryl group having 5 to 30 ring atoms;
each $R_2$ independently represents a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted haloalkyl group having 1 to 30 carbon atoms, a substituted or unsubstituted cycloalkyl group having 3 to 30 ring carbon atoms, a substituted or unsubstituted silyl group, a cyano group, a substituted or unsubstituted alkoxy group having 1 to 30 carbon atoms, a substituted or unsubstituted aryloxy group having 6 to 30 ring carbon atoms, a substituted or unsubstituted aralkyl group having 7 to 30 carbon atoms, a halogen atom, or a substituted carbonyl group, and when k is 2 or more, the groups $R_2$ on adjacent ring carbon atoms may be bonded to each other to form a hydrocarbon ring;

each of $R_3$ and $R_4$ independently represents a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted haloalkyl group having 1 to 30 carbon atoms, a substituted or unsubstituted cycloalkyl group having 3 to 30 ring carbon atoms, a substituted or unsubstituted silyl group, a cyano group, a substituted or unsubstituted alkoxy group having 1 to 30 carbon atoms, a substituted or unsubstituted aryloxy group having 6 to 30 ring carbon atoms, a substituted or unsubstituted aralkyl group having 7 to 30 carbon atoms, a halogen atom, or a substituted carbonyl group, when p is 2 or more, the groups $R_3$ on adjacent ring carbon atoms may be bonded to each other to form a hydrocarbon ring, and when q is 2 or more, the groups $R_4$ on adjacent ring carbon atoms may be bonded to each other to form a hydrocarbon ring;

X represents an oxygen atom or a sulfur atom;

k represents an integer of 0 to 5;

m represents an integer of 1 to 2;

n represents an integer of 1 to 2;

p represents an integer of 0 to 3; and q represents an integer of 0 to 4;

2. the aromatic amine derivative according to item 1, wherein the aromatic amine derivative is represented by formula (2):

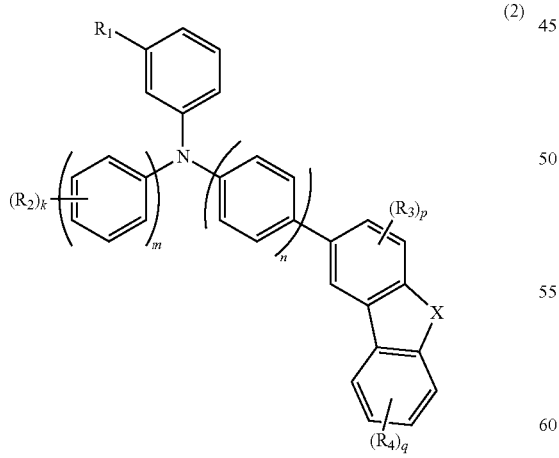

(2)

wherein $R_1$, $R_2$, $R_3$, $R_4$, X, k, m, n, p, and q are as defined above;

3. the aromatic amine derivative according to item 2, wherein the aromatic amine derivative is represented by formula (3):

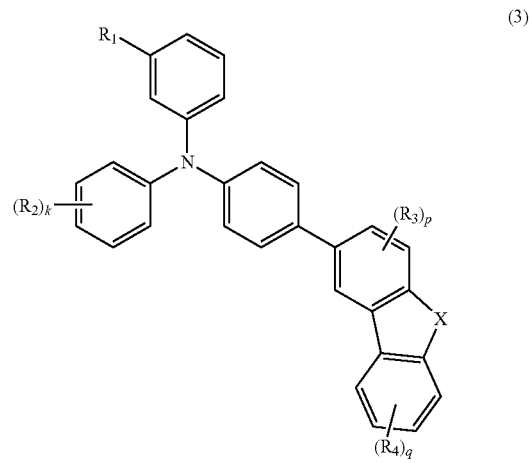

(3)

wherein $R_1$, $R_2$, $R_3$, $R_4$, X, k, p, and q are as defined above;

4. the aromatic amine derivative according to item 1, wherein the aromatic amine derivative is represented by formula (4):

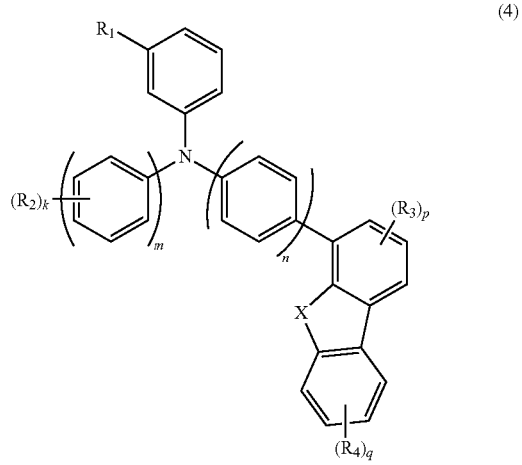

(4)

wherein $R_1$, $R_2$, $R_3$, $R_4$, X, k, m, n, p, and q are as defined above;

5. the aromatic amine derivative according to item 4, wherein the aromatic amine derivative is represented by formula (5):

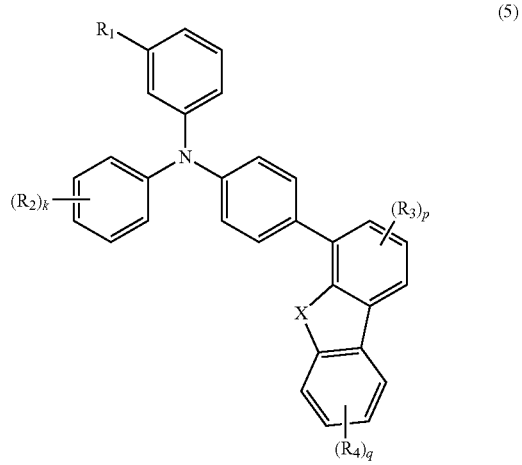

(5)

wherein $R_1$, $R_2$, $R_3$, $R_4$, X, k, p, and q are as defined above;

6. the aromatic amine derivative according to item 1, wherein the aromatic amine derivative is represented by formula (6):

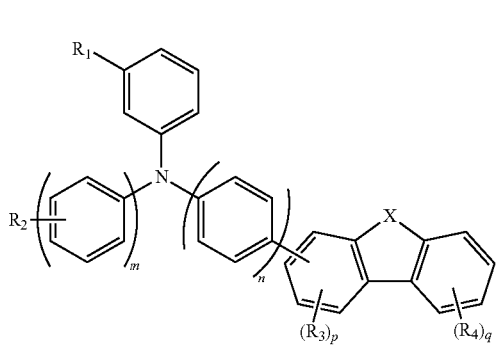

(6)

wherein $R_1$, $R_2$, $R_3$, $R_4$, X, m, n, p, and q are as defined above;

7. the aromatic amine derivative according to item 3, wherein the aromatic amine derivative is represented by formula (7):

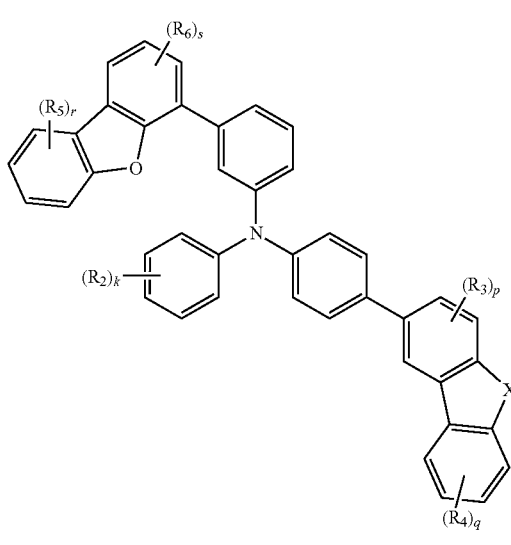

(7)

wherein:
$R_2$, $R_3$, $R_4$, X, k, p, and q are as defined above;
each of $R_5$ and $R_6$ independently represents a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted haloalkyl group having 1 to 30 carbon atoms, a substituted or unsubstituted cycloalkyl group having 3 to 30 ring carbon atoms, a substituted or unsubstituted silyl group, a cyano group, a substituted or unsubstituted alkoxy group having 1 to 30 carbon atoms, a substituted or unsubstituted aryloxy group having 6 to 30 ring carbon atoms, a substituted or unsubstituted aralkyl group having 7 to 30 carbon atoms, a halogen atom, or a substituted carbonyl group, when r is 2 or more, the groups $R_5$ on adjacent ring carbon atoms may be bonded to each other to form a hydrocarbon ring, and when s is 2 or more, the groups $R_6$ on adjacent ring carbon atoms may be bonded to each other to form a hydrocarbon ring;
r represents an integer of 0 to 4; and
s represents an integer of 0 to 3;

8. the aromatic amine derivative according to item 5, wherein the aromatic amine derivative is represented by formula (8):

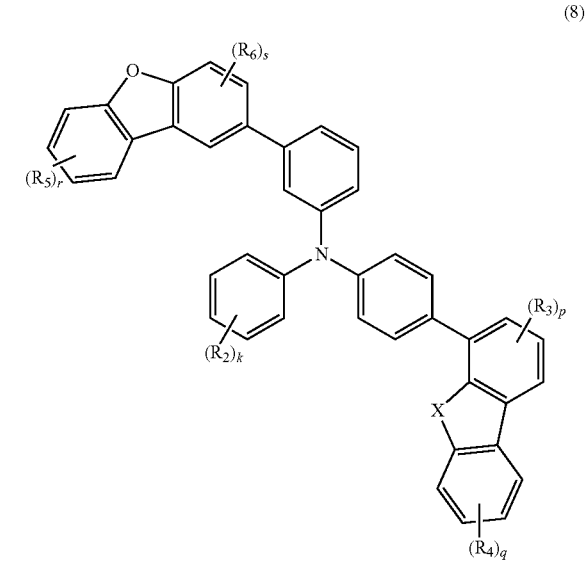

(8)

wherein $R_2$, $R_3$, $R_4$, $R_5$, $R_6$, X, k, p, q, r, and s are as defined above;

9. the aromatic amine derivative according to any one of items 1 to 6, wherein $R_1$ in formulae (1) to (6) is represented by any one of formulae (11-1) to (11-4):

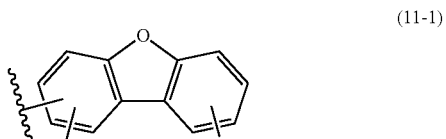

(11-1)

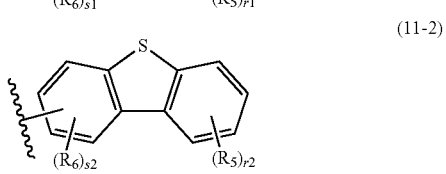

(11-2)

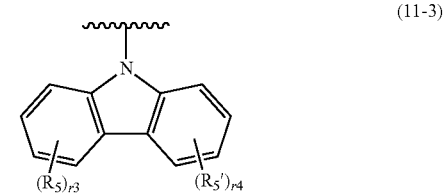

(11-3)

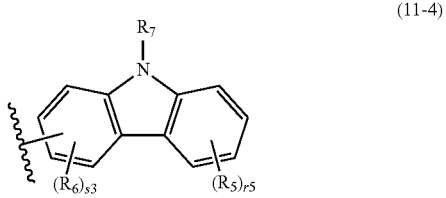

(11-4)

wherein:
each of $R_5$, $R_5'$ and $R_6$ independently represents a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted haloalkyl group having 1 to 30 carbon atoms, a substituted or unsubstituted cycloalkyl group having 3 to 30 ring carbon atoms, a substituted or unsubstituted silyl group, a cyano group, a substituted or unsubstituted alkoxy group having 1 to 30 carbon atoms, a substituted or unsubstituted aryloxy group having 6 to 30 ring carbon atoms, a substituted or unsubstituted aralkyl group having 7 to 30 carbon atoms, a halogen atom, or a substituted carbonyl group;

when each of r1 to r5 is 2 or more, the groups $R_5$ or the groups $R_5'$ on adjacent ring carbon atoms may be bonded to each other to form a hydrocarbon ring, and when each of s1 to s3 is 2 or more, the groups $R_6$ on adjacent ring carbon atoms may be bonded to each other to form a hydrocarbon ring;

$R_7$ represents a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted haloalkyl group having 1 to 30 carbon atoms, a substituted or unsubstituted cycloalkyl group having 3 to 30 ring carbon atoms, or a substituted or unsubstituted aralkyl group having 7 to 30 carbon atoms;

each of r1 to r5 independently represents an integer of 0 to 4; and each of s1 to s3 independently represents an integer of 0 to 3;

10. the aromatic amine derivative according to any one of items 1 to 9, wherein the aromatic amine derivative is a material for an organic electroluminescence device;

11. the aromatic amine derivative according to any one of items 1 to 9, wherein the aromatic amine derivative is a hole injecting material or a hole transporting material for an organic electroluminescence device;

12. an organic electroluminescence device which comprises a cathode, an anode, and an organic thin film layer comprising one or more layers between the cathode and the anode, wherein the organic thin film layer comprises a light emitting layer, and at least one layer of the organic thin film layer comprises the aromatic amine derivative according to any one of items 1 to 9 singly or in combination; and 13. the organic electroluminescence device according to item 12, wherein the organic thin film layer comprises a hole transporting layer and the hole transporting layer comprises the aromatic amine derivative.

Effects of the Invention

By using the aromatic amine derivative of the invention as a material for an organic EL device, an organic electroluminescence device having a long lifetime and a higher emission efficiency is obtained.

BRIEF DESCRIPTION OF THE DRAWINGS

FIG. 1 is a schematic cross-sectional view of an example of the organic EL device of the invention.

MODE FOR CARRYING OUT THE INVENTION

The "carbon number of a to b" referred to in the term of "a substituted or unsubstituted X group having a to b carbon atoms" is the carbon number of the unsubstituted X group and does not include the carbon atom of the optional substituent of the X group.

The definition of hydrogen atom in the present specification includes isotopes different in the neutron numbers, i.e., light hydrogen (protium), heavy hydrogen (deuterium), and tritium.

The aromatic amine derivative of the invention is represented by formula (1):

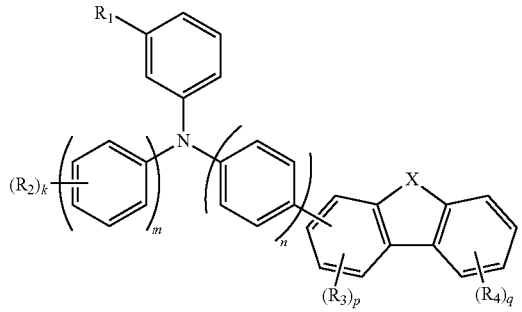

wherein:

$R_1$ represents a substituted or unsubstituted heteroaryl group having 5 to 30 ring atoms;

each $R_2$ independently represents a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted haloalkyl group having 1 to 30 carbon atoms, a substituted or unsubstituted cycloalkyl group having 3 to 30 ring carbon atoms, a substituted or unsubstituted silyl group, a cyano group, a substituted or unsubstituted alkoxy group having 1 to 30 carbon atoms, a substituted or unsubstituted aryloxy group having 6 to 30 ring carbon atoms, a substituted or unsubstituted aralkyl group having 7 to 30 carbon atoms, a halogen atom, or a substituted carbonyl group, and when k is 2 or more, the groups $R_2$ on adjacent ring carbon atoms may be bonded to each other to form a hydrocarbon ring;

each of $R_3$ and $R_4$ independently represents a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted haloalkyl group having 1 to 30 carbon atoms, a substituted or unsubstituted cycloalkyl group having 3 to 30 ring carbon atoms, a substituted or unsubstituted silyl group, a cyano group, a substituted or unsubstituted alkoxy group having 1 to 30 carbon atoms, a substituted or unsubstituted aryloxy group having 6 to 30 ring carbon atoms, a substituted or unsubstituted aralkyl group having 7 to 30 carbon atoms, a halogen atom, or a substituted carbonyl group, when p is 2 or more, the groups $R_3$ on adjacent ring carbon atoms may be bonded to each other to form a hydrocarbon ring, and when q is 2 or more, the groups $R_4$ on adjacent ring carbon atoms may be bonded to each other to form a hydrocarbon ring;

X represents an oxygen atom or a sulfur atom;

k represents an integer of 0 to 5;

m represents an integer of 1 to 2;

n represents an integer of 1 to 2;

p represents an integer of 0 to 3; and q represents an integer of 0 to 4.

The aromatic amine derivative has a structure in which a dibenzofuranyl group or a dibenzothiophenyl group is bonded via p-phenylene. With this structure, the lifetime of an organic EL device which comprises the aromatic amine derivative is prolonged. Absent the above structure, the effect of the invention to prolong the lifetime cannot be obtained.

The molecular weight of the aromatic amine derivative is preferably 300 to 2000, more preferably 400 to 1500, and particularly preferably 500 to 1200. If the molecular weight is 300 to 2000, the aromatic amine derivative can be purified by sublimation to provide a highly pure compound which improves the performance of a device comprising it, in addition, a device can be produced preferably by a vapor deposition method.

The aromatic amine derivative represented by formula (1) is preferably represented by any of formulae (2) to (10).

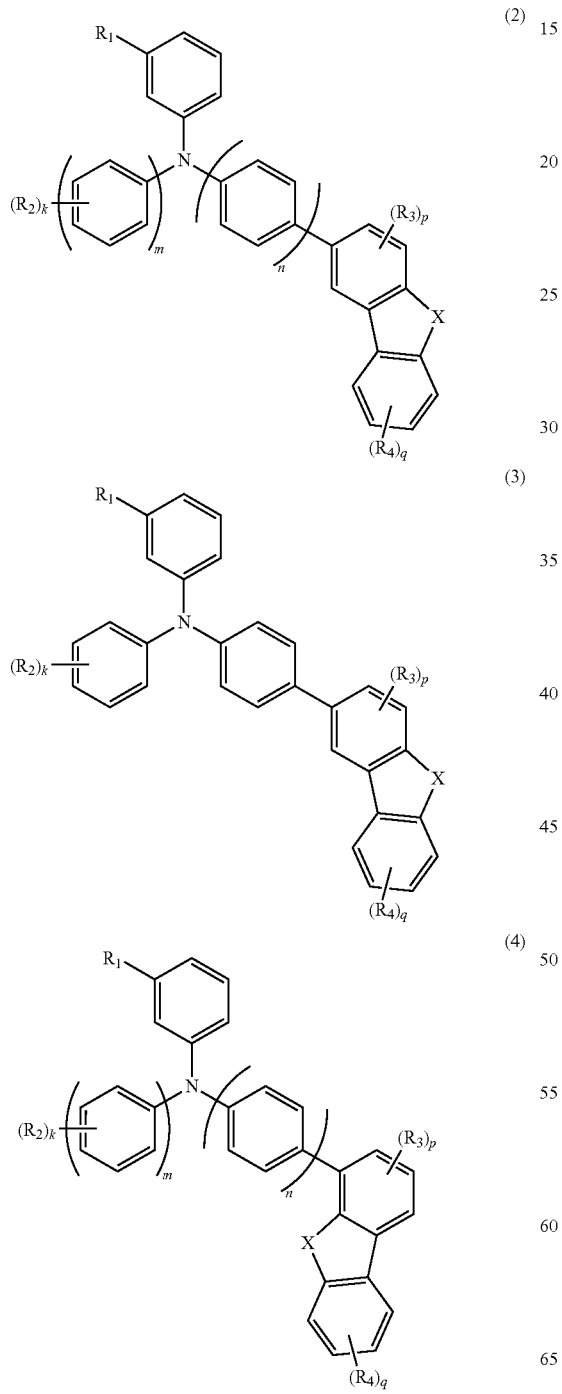

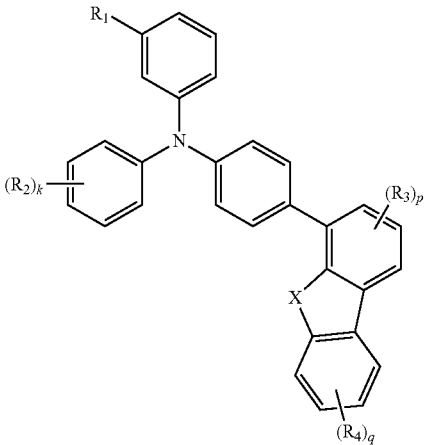

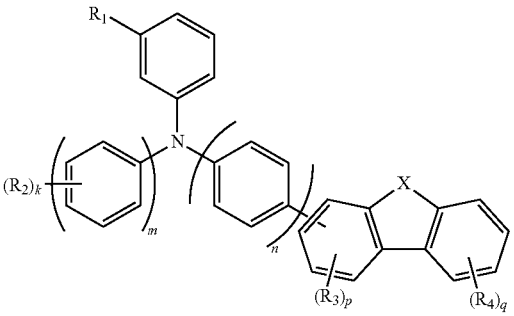

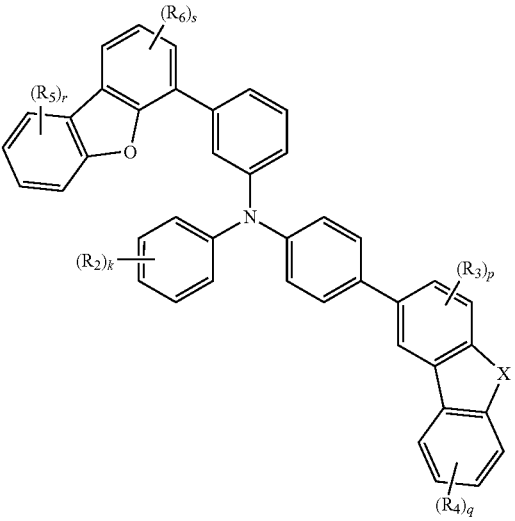

-continued

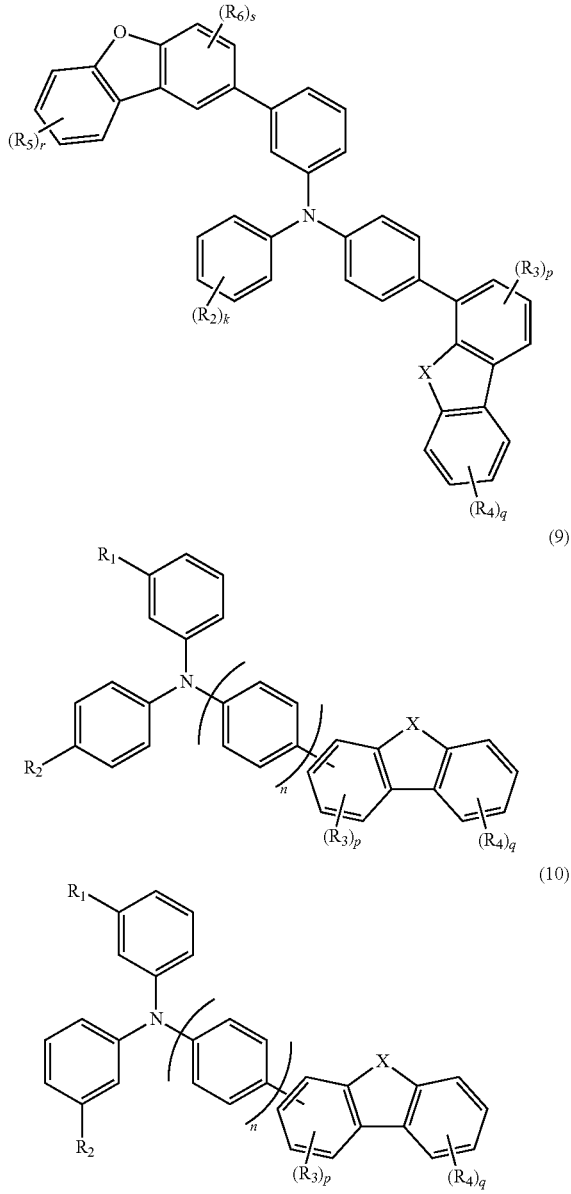

In formulae (2) to (10), $R_1$, $R_2$, $R_3$, $R_4$, X, k, m, n, p, and q are as defined in formula (1); and In formula (7):

each of $R_5$ and $R_6$ independently represents a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted haloalkyl group having 1 to 30 carbon atoms, a substituted or unsubstituted cycloalkyl group having 3 to 30 ring carbon atoms, a substituted or unsubstituted silyl group, a cyano group, a substituted or unsubstituted alkoxy group having 1 to 30 carbon atoms, a substituted or unsubstituted aryloxy group having 6 to 30 ring carbon atoms, a substituted or unsubstituted aralkyl group having 7 to 30 carbon atoms, a halogen atom, or a substituted carbonyl group;

when r is 2 or more, the groups $R_5$ on adjacent ring carbon atoms may be bonded to each other to form a hydrocarbon ring, and when s is 2 or more, the groups $R_6$ on adjacent ring carbon atoms may be bonded to each other to form a hydrocarbon ring;

r represents an integer of 0 to 4; and s represents an integer of 0 to 3.

In view of obtaining an organic EL device having a long lifetime, the aromatic amine derivative is preferably represented by formula (9), and in view of the emission efficiency, the aromatic amine derivative is preferably represented by formula (10).

Each of $R_1$ and $R_2$ in formulae (1) to (4) is independently represented preferably by any of formulae (11-1) to (11-4):

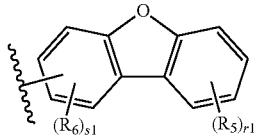

(11-1)

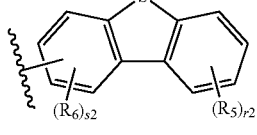

(11-2)

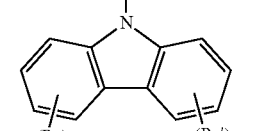

(11-3)

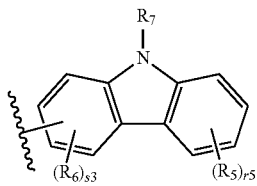

(11-4)

wherein:

each of $R_5$, $R_5'$ and $R_6$ independently represents a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted haloalkyl group having 1 to 30 carbon atoms, a substituted or unsubstituted cycloalkyl group having 3 to 30 ring carbon atoms, a substituted or unsubstituted silyl group, a cyano group, a substituted or unsubstituted alkoxy group having 1 to 30 carbon atoms, a substituted or unsubstituted aryloxy group having 6 to 30 ring carbon atoms, a substituted or unsubstituted aralkyl group having 7 to 30 carbon atoms, a halogen atom, or a substituted carbonyl group;

when each of r1 to r5 is 2 or more, the groups $R_5$ or the groups $R_5'$ on adjacent ring carbon atoms may be bonded to each other to form a hydrocarbon ring, and when each of s1 to s3 is 2 or more, the groups $R_6$ on adjacent ring carbon atoms may be bonded to each other to form a hydrocarbon ring;

$R_7$ represents a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted haloalkyl group having 1 to 30 carbon atoms, a substituted or unsubstituted cycloalkyl group having 3 to 30 ring carbon atoms, or a substituted or unsubstituted aralkyl group having 7 to 30 carbon atoms;

each of r1 to r5 independently represents an integer of 0 to 4; and each of s1 to s3 independently represents an integer of 0 to 3.

The aromatic amine derivative is preferably represented by formula (9) or (10), wherein $R_2$ is represented by any of formulae (11-1) to (11-4).

Examples of the aryl group mentioned above include a phenyl group, a 2-methylphenyl group, a 3-methylphenyl group, a 4-methylphenyl group, a 4-ethylphenyl group, a biphenylyl group, a 4-methylbiphenylyl group, a 4-ethylbiphenylyl group, a 4-cyclohexylbiphenylyl group, an anthracenyl group, a naphthacenyl group, a terphenyl group, a triphenylyl group, a 3,5-dichlorophenylyl group, a naphthyl group, a 5-methylnaphthyl group, a phenanthryl group, a chrysenyl group, a benzophenanthryl group, a terphenyl group, a benzanthranyl group, a benzochrysenyl group, a pentacenyl group, a picenyl group, a pentaphenyl group, a pyrenyl group, a chrysenyl group, a fluorenyl group, an indenyl group, an acenaphthylenyl group, a fluoranthenyl group, and a perylenyl group, with a phenyl group, a biphenylyl group, and a naphthyl group being preferred.

Examples of the heteroaryl group mentioned above include a pyrrolyl group, a furyl group, a thienyl group, a silolyl group, a pyridyl group, a quinolyl group, an isoquinolyl group, a benzofuryl group, a benzothienyl group, an imidazolyl group, a pyrimidyl group, a carbazolyl group, a selenophenyl group, an oxadiazolyl group, a triazolyl group, a pyrazinyl group, a pyridazinyl group, a triazinyl group, a quinoxalinyl group, an acridinyl group, an imidazo[1,2-a]pyridinyl group, an imidazo[1,2-a]pyrimidinyl group, a dibenzofuryl group, and a dibenzothienyl group.

Examples of the alkyl group mentioned above include a methyl group, an ethyl group, a propyl group, an isopropyl group, a n-butyl group, an isobutyl group, a sec-butyl group, a tert-butyl group, a n-pentyl group, a n-hexyl group, a n-heptyl group, a n-octyl group, a hydroxymethyl group, a 1-hydroxyethyl group, a 2-hydroxyethyl group, a 2-hydroxyisobutyl group, a 1,2-dihydroxyethyl group, a 1,3-dihydroxyisopropyl group, a 2,3-dihydroxy-t-butyl group, and a 1,2,3-trihydroxypropyl group, with a methyl group, an ethyl group, a propyl group, an isopropyl group, a n-butyl group, an isobutyl group, a sec-butyl group, and a tert-butyl group being preferred.

Examples of the cycloalkyl group mentioned above include a cyclopropyl group, a cyclobutyl group, a cyclopentyl group, a cyclohexyl group, a cyclopentylmethyl group, a cyclohexylmethyl group, a cyclohexylethyl group, a 4-fluorocyclohexyl group, a 1-adamantyl group, a 2-adamantyl group, a 1-norbornyl group, and a 2-norbornyl group, with a cyclopentyl group and a cyclohexyl group being preferred.

Examples of the haloalkyl group mentioned above include those obtained by replacing one or more hydrogen atoms of the alkyl groups mentioned above by at least one halogen atom selected from fluorine, chlorine, iodine, and bromine.

Examples of the aralkyl group mentioned above include those having the alkyl group mentioned above as the alkyl portion and the aryl group mentioned above as the aryl portion.

Examples of the halogen atom mentioned above include fluorine, chlorine, and iodine.

Examples of the hydrocarbon ring mentioned above which is formed by the groups $R_1$ to $R_6$ and $R_5'$ on adjacent ring carbon atoms by bonding to each other include the aryl groups and the cycloalkyl groups, each mentioned above.

In a preferred embodiment, each of $R_3$ to $R_7$ and $R_5'$ in formulae (1) to (10) and (11-1) to (11-4) independently represents an aryl group having 6 to 16, preferably 6 to 10 ring carbon atoms, a heteroaryl group having 5 to 16, preferably 5 to 10 ring atoms, a linear or branched alkyl group having 1 to 10, preferably 1 to 6 carbon atoms, a linear or branched haloalkyl group having 1 to 10, preferably 1 to 6 carbon atoms, a cycloalkyl group having 3 to 10, preferably 5 to 7 ring carbon atoms, a trialkylsilyl group having 3 to 10, preferably 3 to 6 carbon atoms, a triarylsilyl group having 18 to 30, preferably 18 to 24 ring carbon atoms, an alkylarylsilyl group 8 to 15, preferably 8 to 12 carbon atoms in which the aryl portion has 6 to 14, preferably 6 to 10 ring carbon atoms, or a halogen atom, preferably a fluorine atom. The groups $R_3$ to the groups $R_6$ and the groups $R_5'$ on adjacent ring carbon atoms may be bonded to each other to independently form a hydrocarbon ring.

Examples of the trialkylsilyl group mentioned above include a trimethylsilyl group, a vinyldimethylsilyl group, a triethylsilyl group, a tripropylsilyl group, a propyldimethylsilyl group, a tributylsilyl group, a t-butyldimethylsilyl group, a tripentylsilyl group, a triheptylsilyl group, and a trihexylsilyl group, with a trimethylsilyl group and a triethylsilyl group being preferred. The alkyl substituents of the silyl group may be the same or different.

Examples of the triarylsilyl group mentioned above include a triphenylsilyl group, a trinaphthylsilyl group, and a trianthrylsilyl group, with a triphenylsilyl group being preferred. The aryl substituents of the silyl group may be the same or different.

Examples of the alkylarylsilyl group mentioned above include a dimethylphenylsilyl group, a diethylphenylsilyl group, a dipropylphenylsilyl group, a dibutylphenylsilyl group, a dipentylphenylsilyl group, a diheptylphenylsilyl group, a dihexylphenylsilyl group, a dimethylnaphthylsilyl group, a dipropylnaphthylsilyl group, a dibutylnaphthylsilyl group, a dipentylnaphthylsilyl group, a diheptylnaphthylsilyl group, a dihexylnaphthylsilyl group, a dimethylanthrylsilyl group, a diethylanthrylsilyl group, a dipropylanthrylsilyl group, a dibutylanthrylsilyl group, a dipentylanthrylsilyl group, a diheptylanthrylsilyl group, a dihexylanthrylsilyl group, and a diphenylmethyl group, with a dimethylphenylsilyl group, a diethylphenylsilyl group and a diphenylmethyl group being preferred.

Examples of the optional substituent referred to by the term "a substituted or unsubstituted" mentioned above and below include a halogen atom, a cyano group, an alkyl group having 1 to 20, preferably 1 to 5 carbon atoms, a cycloalkyl group having 3 to 20, preferably 5 to 12 carbon atoms, an alkoxy group having 1 to 20, preferably 1 to 5 carbon atoms, a haloalkyl group having 1 to 20, preferably 1 to 5 carbon atoms, a haloalkoxy group having 1 to 20, preferably 1 to 5 carbon atoms, an alkylsilyl group having 1 to 10, preferably 1 to 5 carbon atoms, an aryl group having 6 to 30, preferably 6 to 18 ring carbon atoms, an aryloxy group having 6 to 30, preferably 6 to 18 ring carbon atoms, an arylsilyl group having 6 to 30, preferably 6 to 18 carbon atoms, an aralkyl group having 7 to 30, preferably 7 to 20 carbon atoms, and a heteroaryl group having 5 to 30, preferably 5 to 18 ring atoms. Specific examples thereof are the same as those described above.

Examples of the aromatic amine derivative represented by any of formulae (1) to (10) include the following compounds.

15
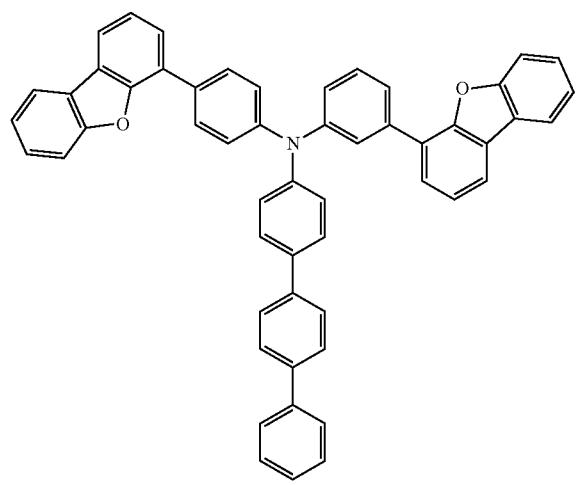
16
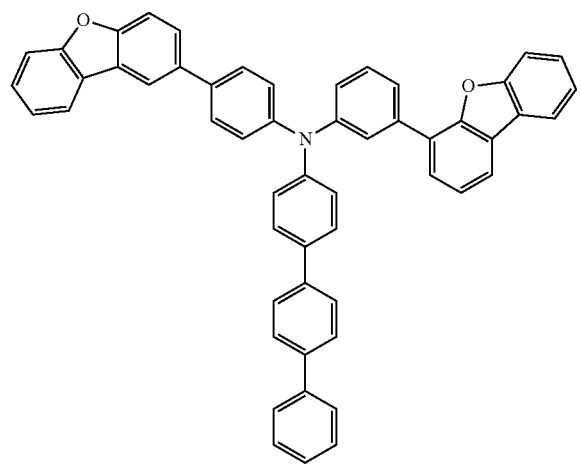
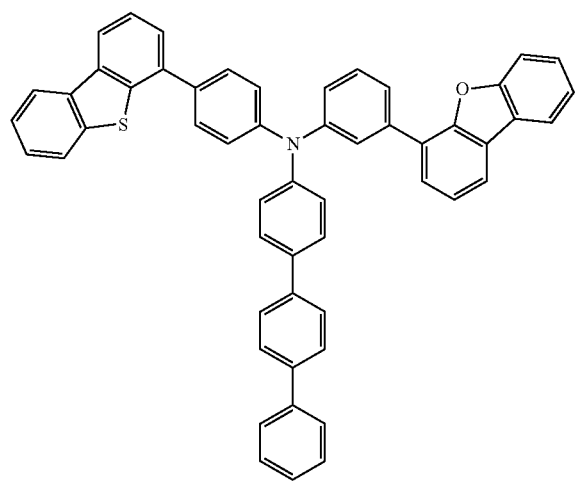
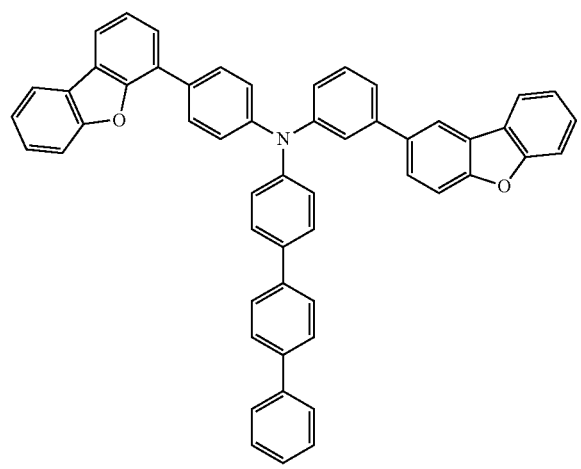
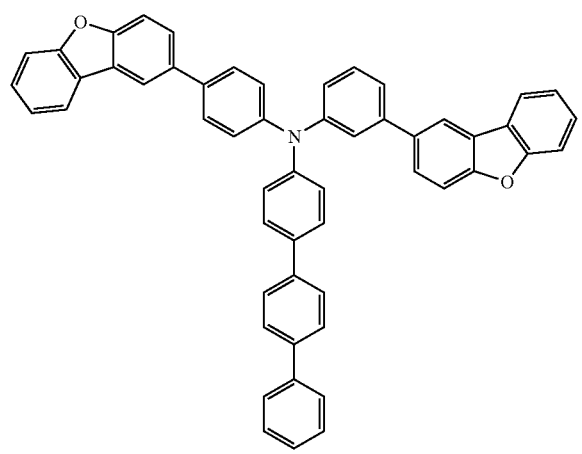
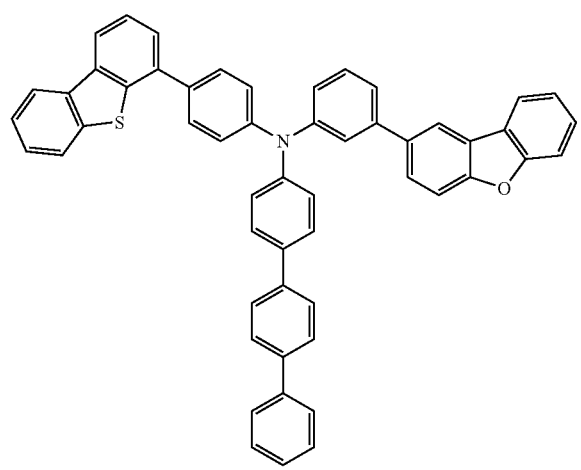

-continued
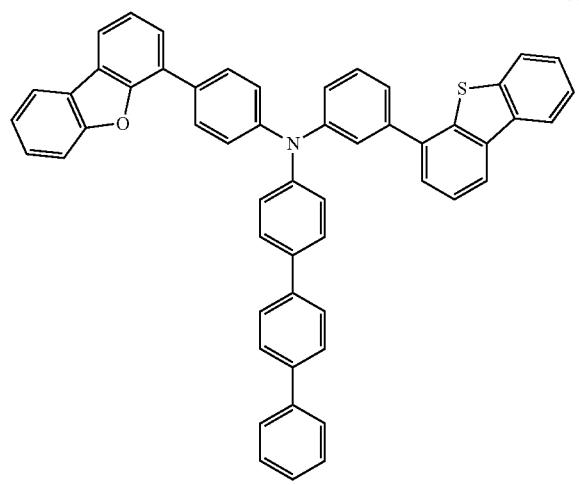
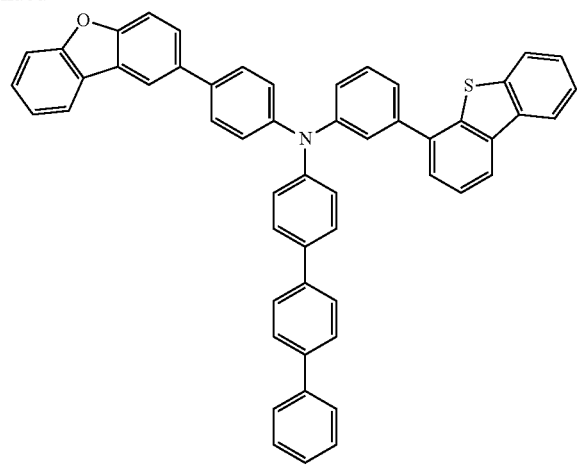
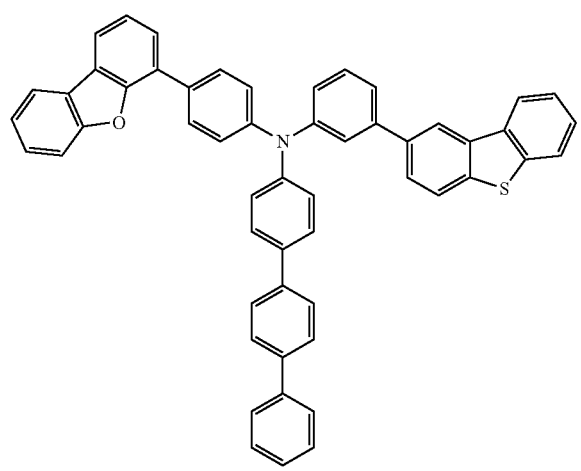
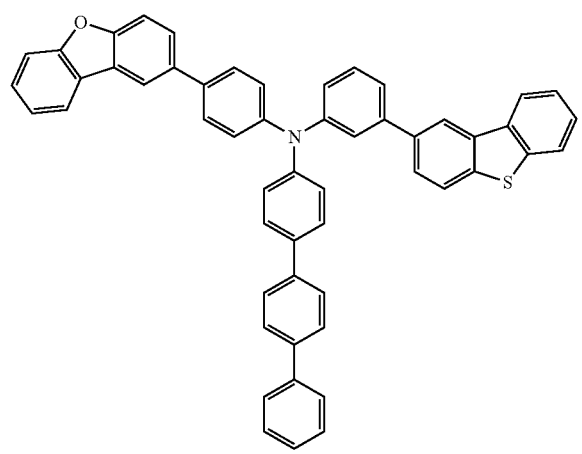
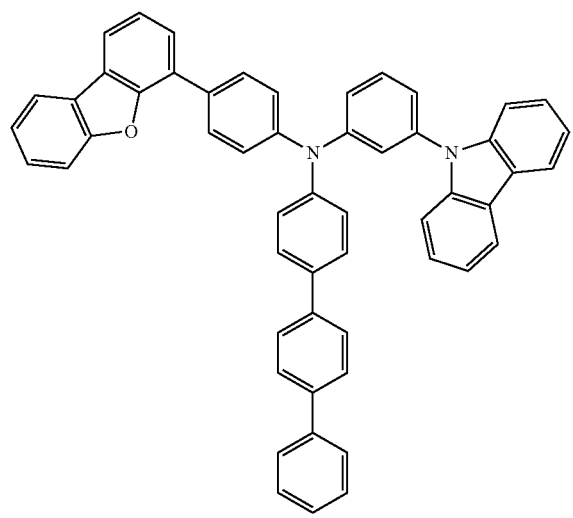
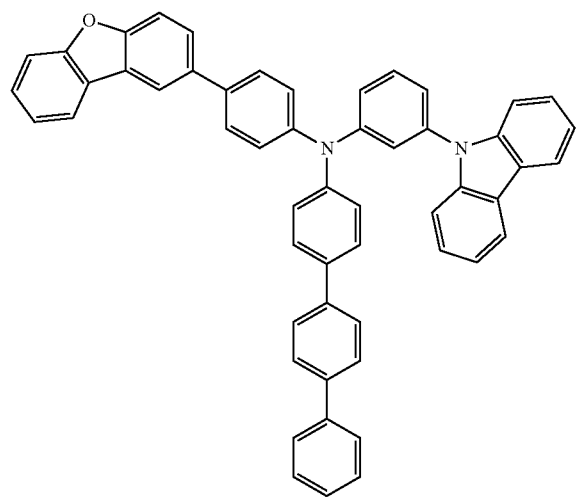

-continued
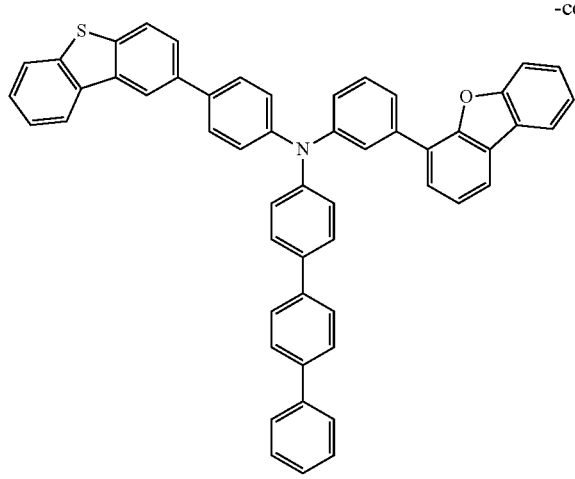
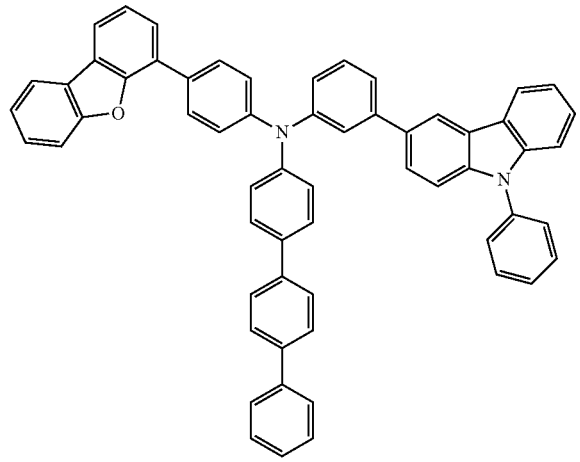
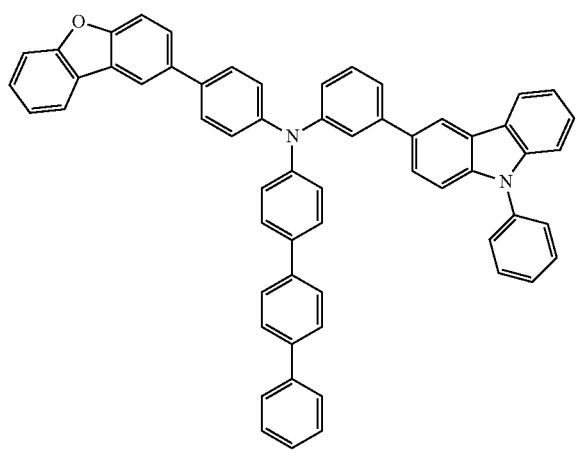
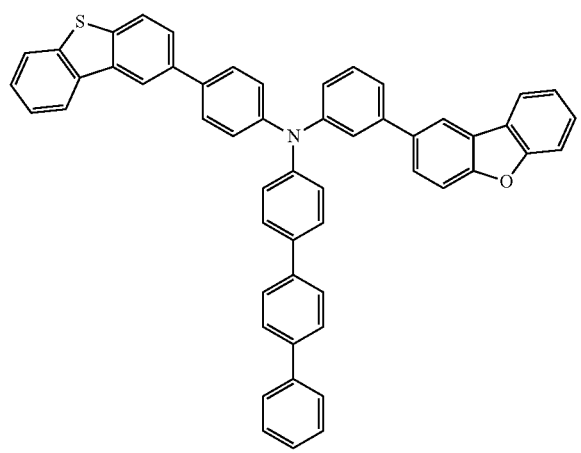
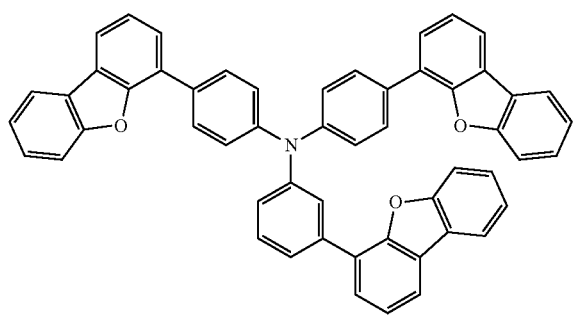
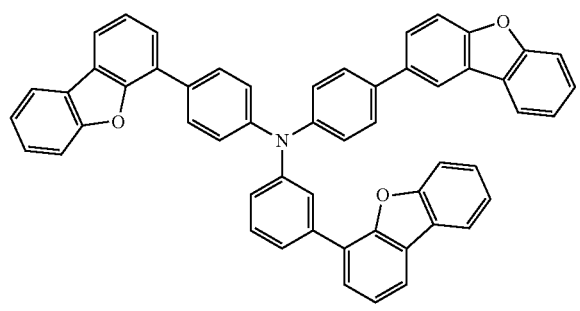
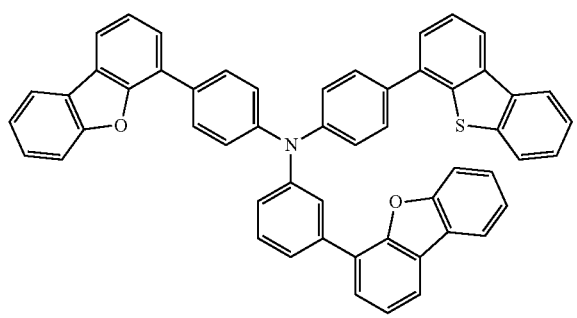
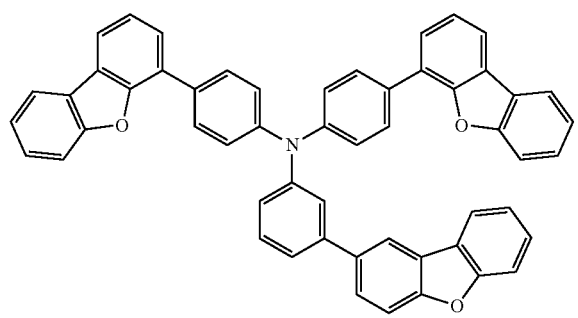

21
22
-continued
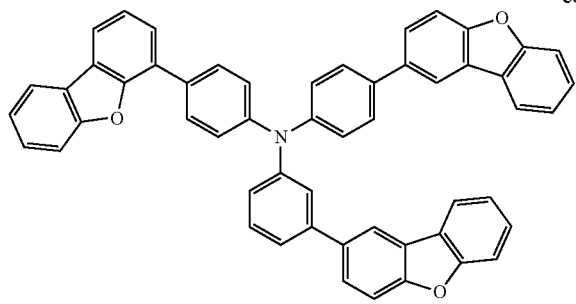
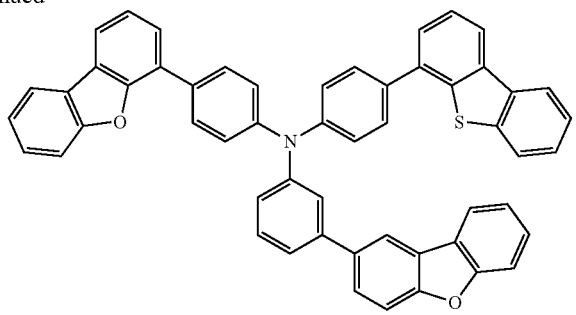
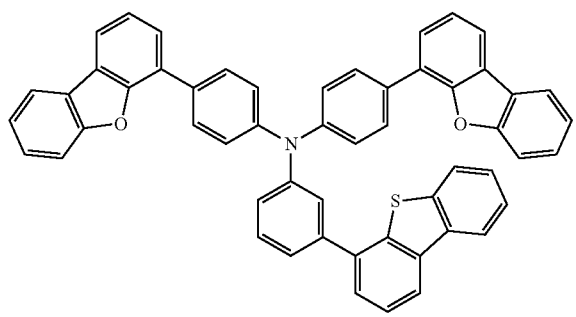
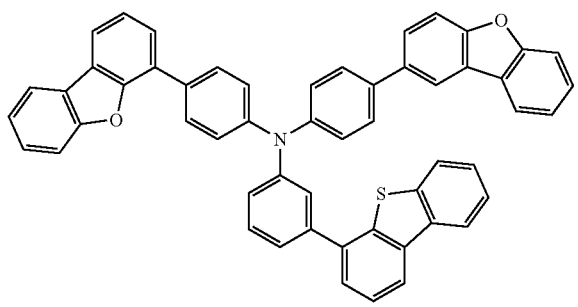
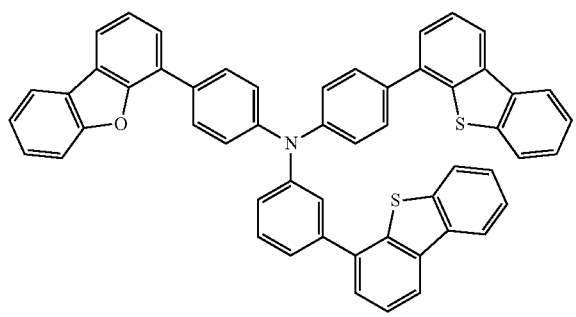
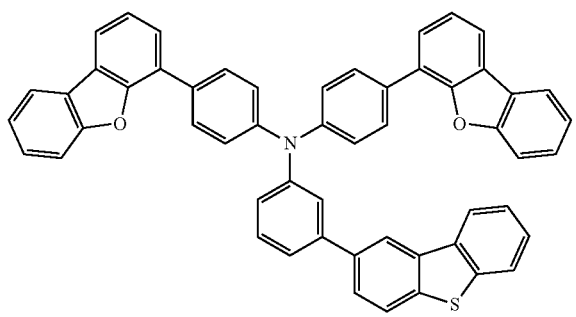
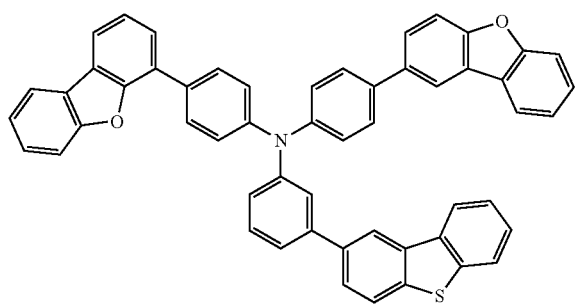
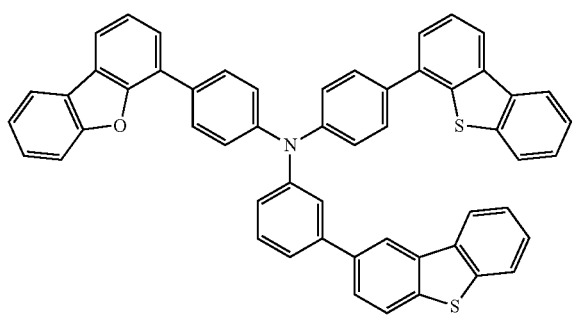
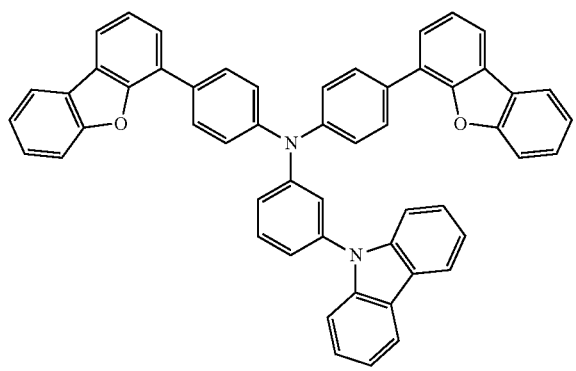
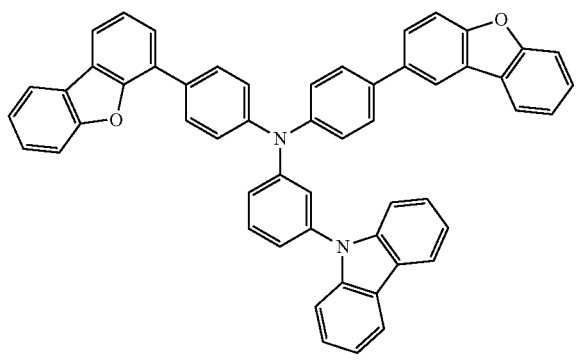

-continued
23
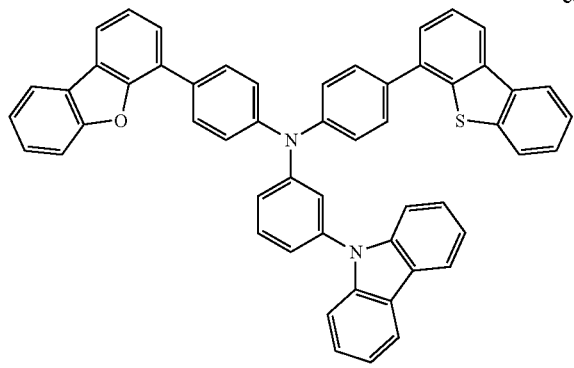
24
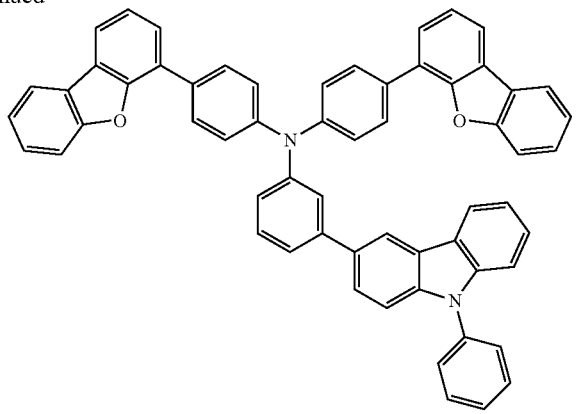
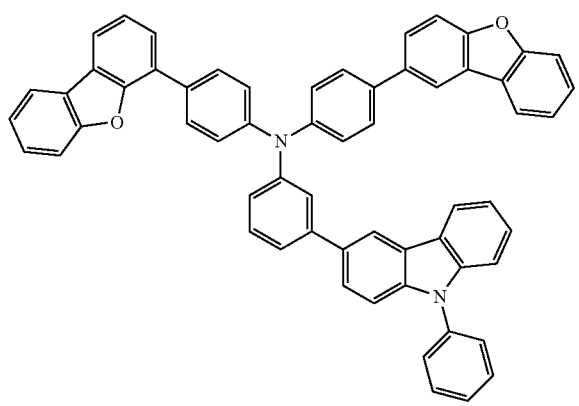
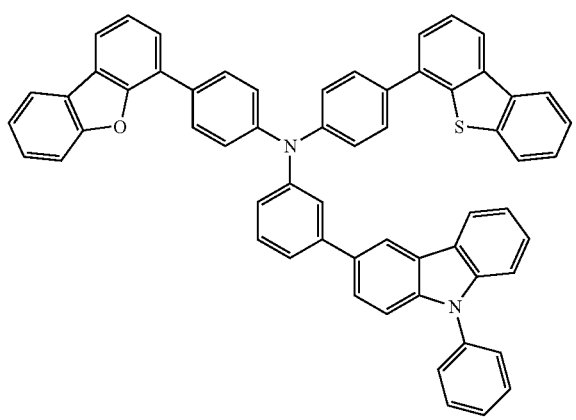
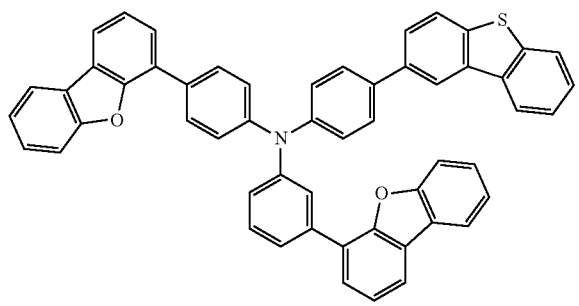
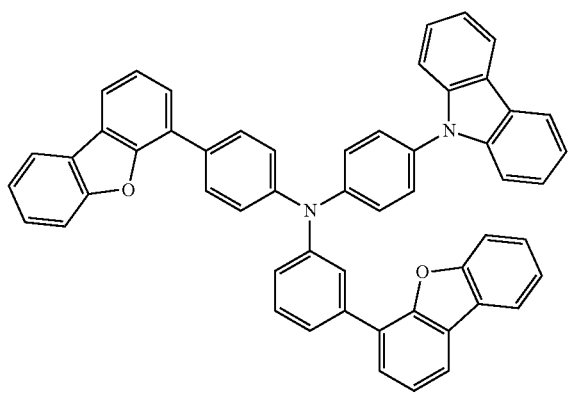
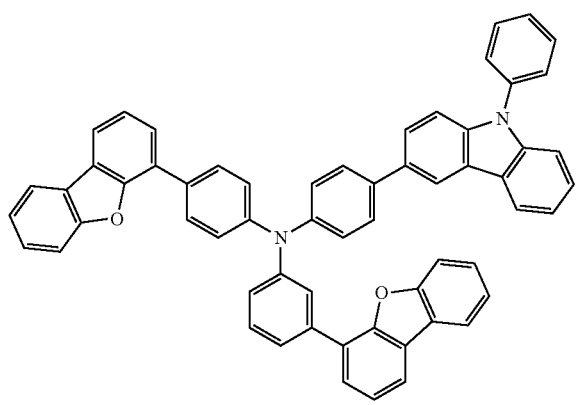
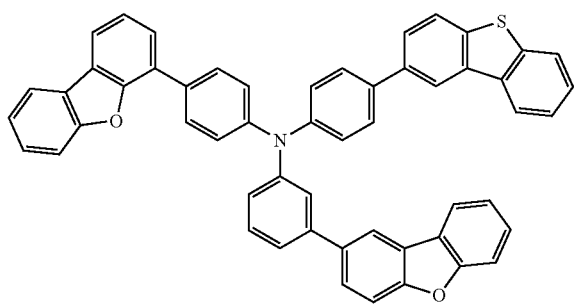

-continued
| 25 | 26 |
|---|---|
| 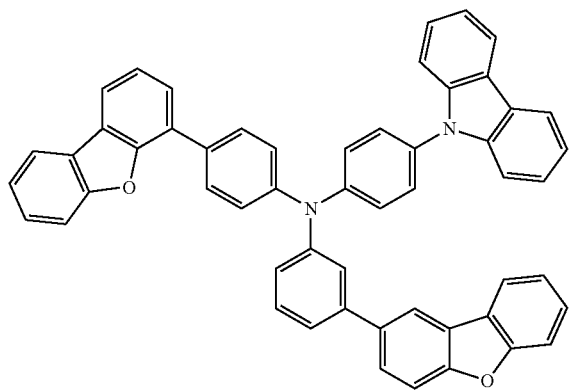 | 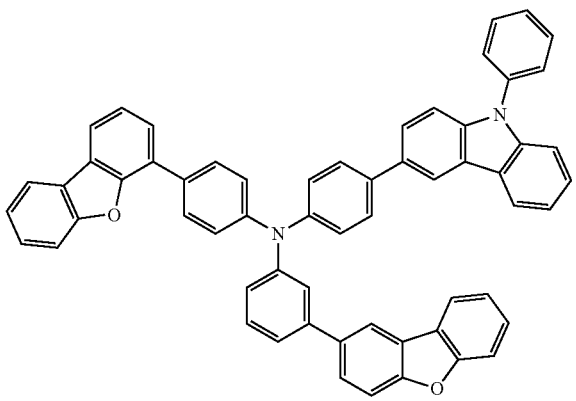 |
| 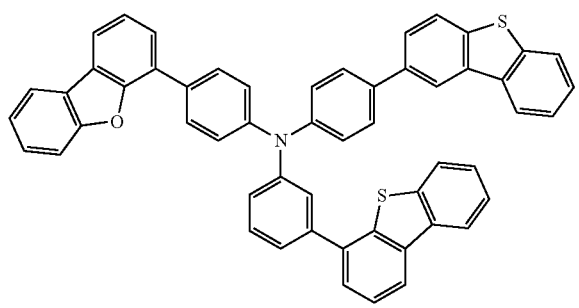 | 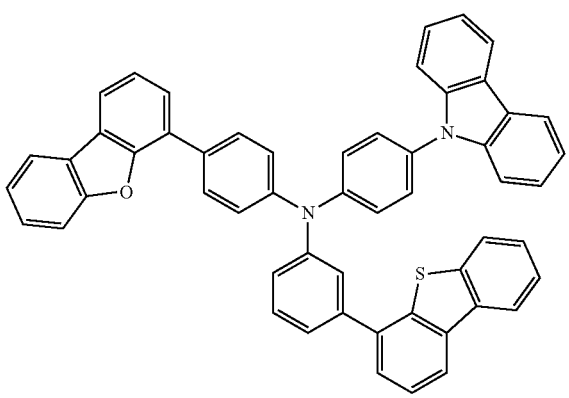 |
| 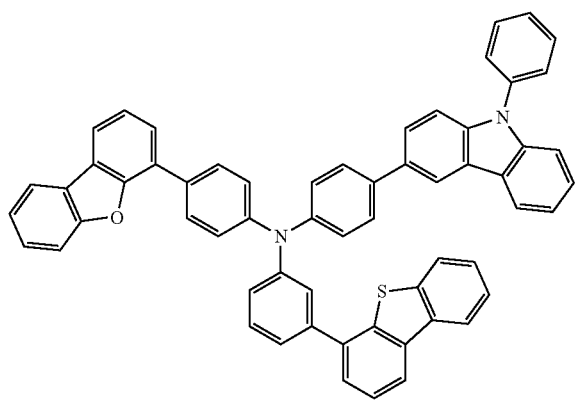 | 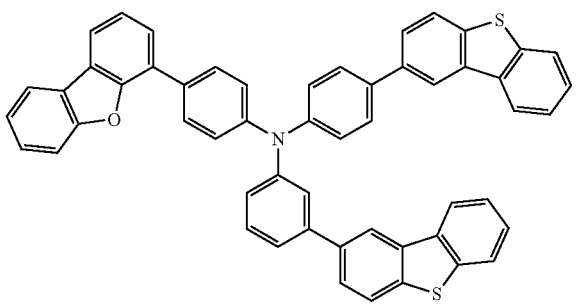 |
| 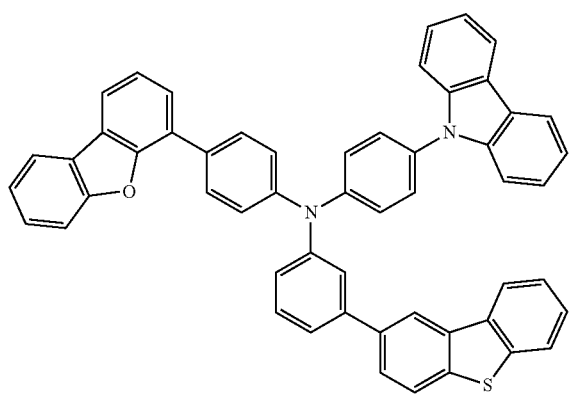 | 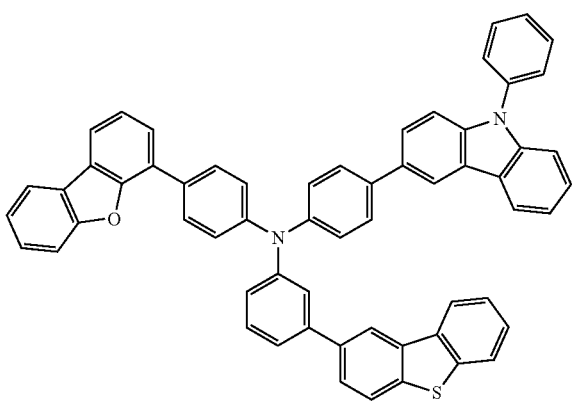 |

-continued
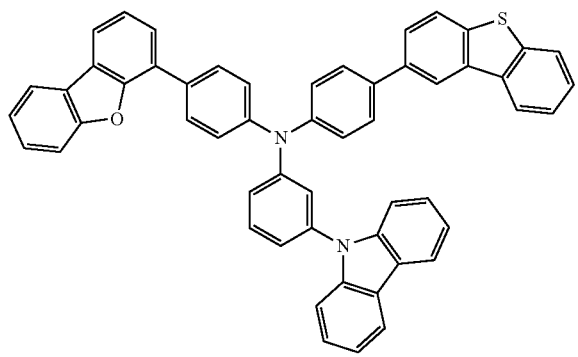
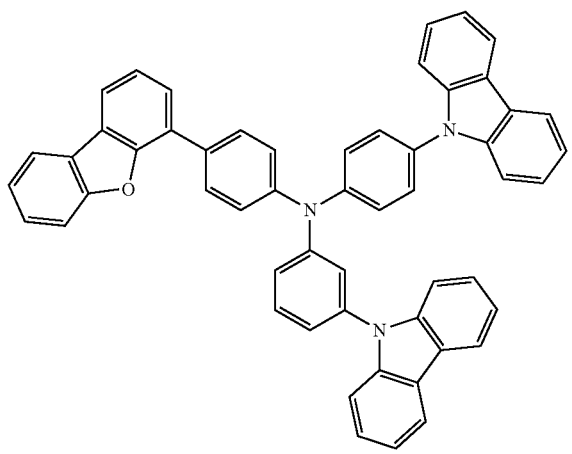
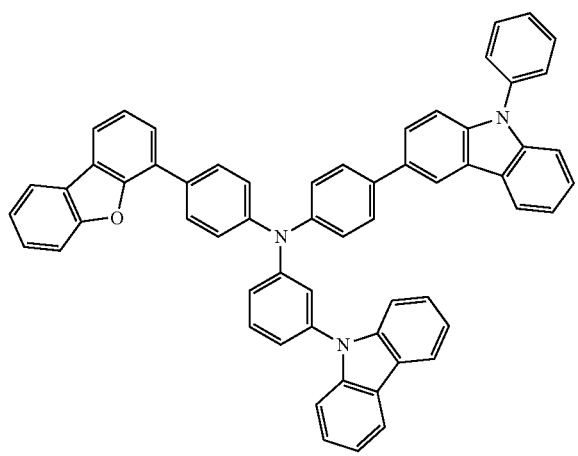
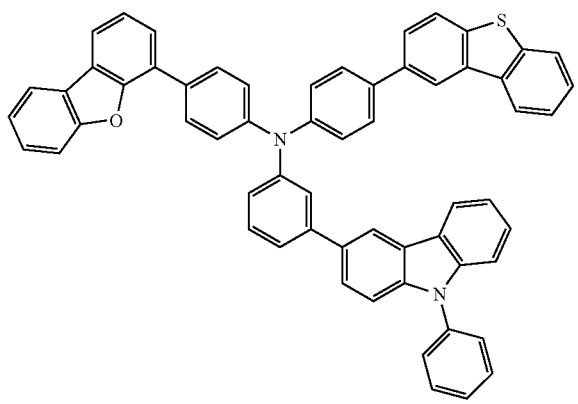
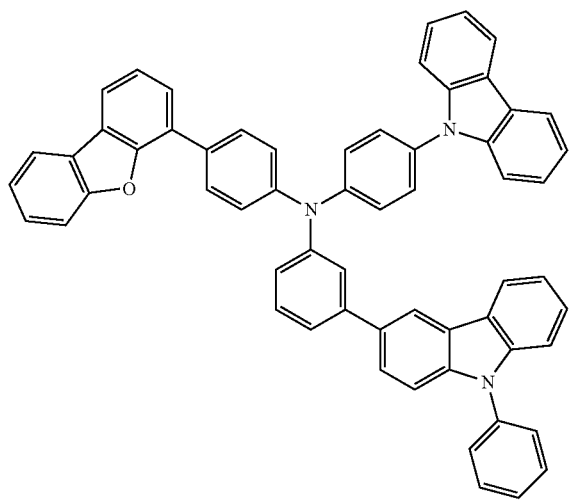
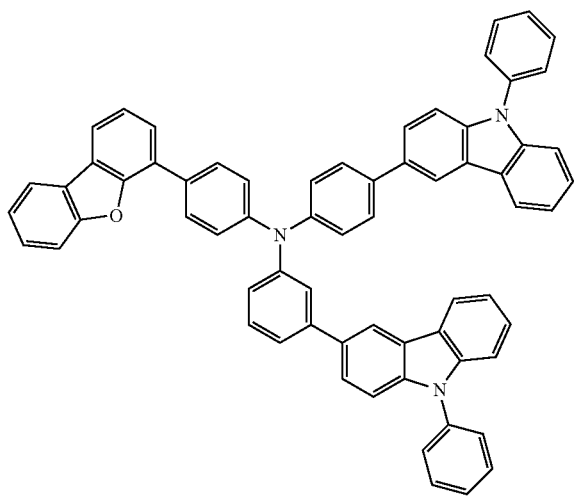
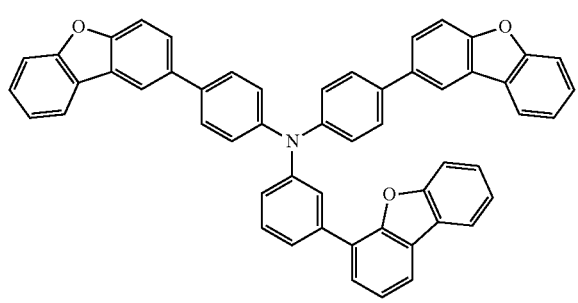
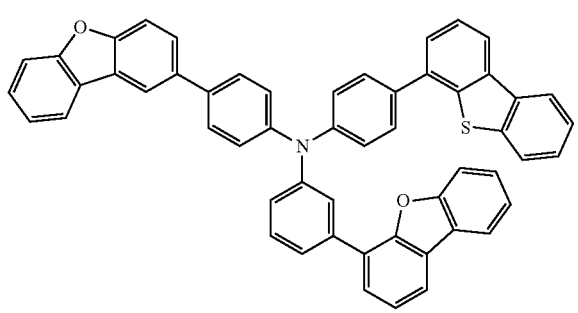

-continued
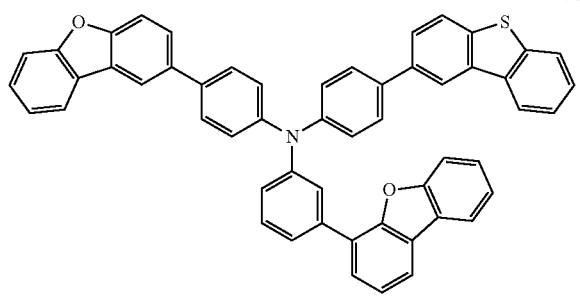
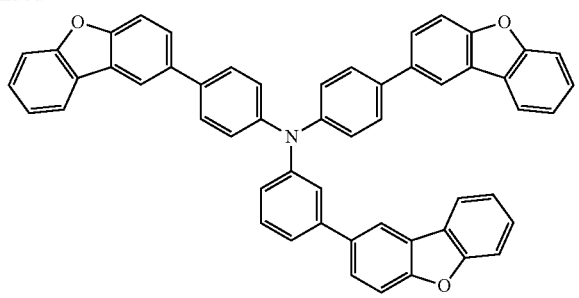
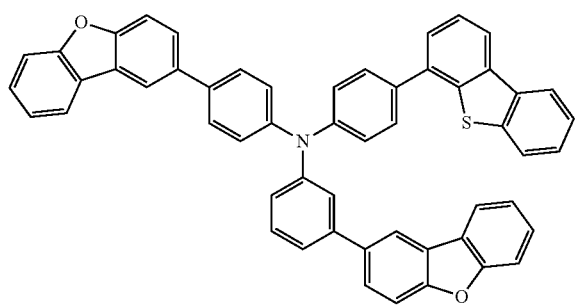
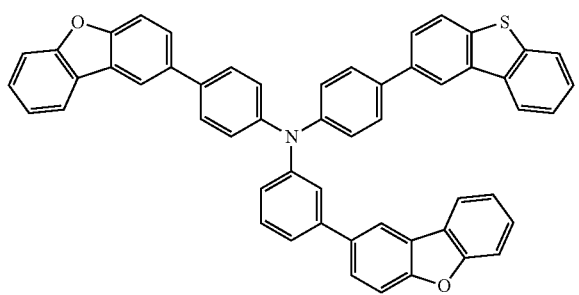
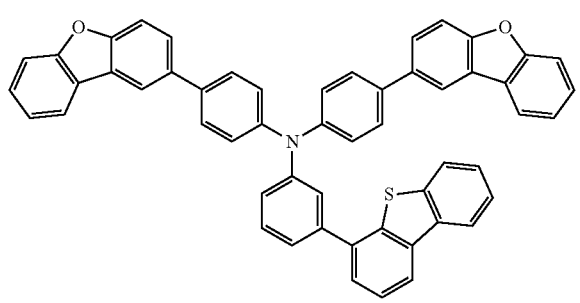
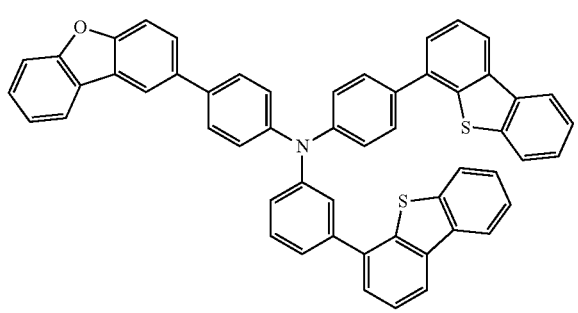
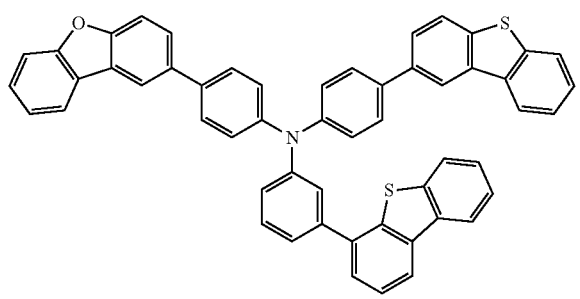
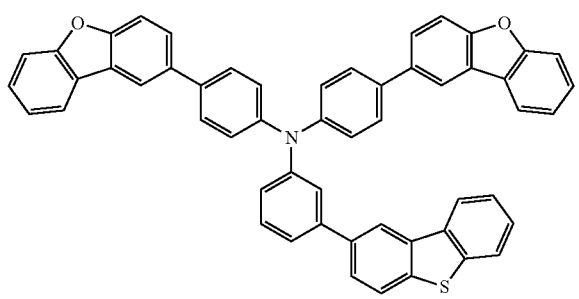
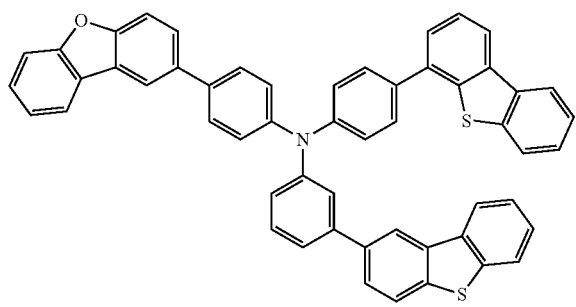
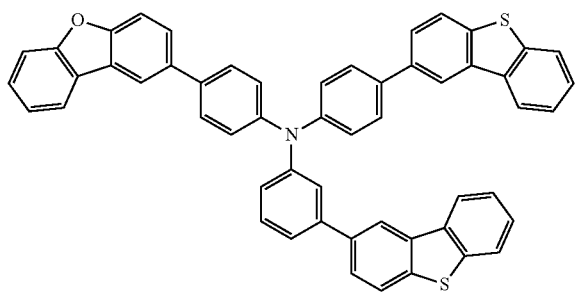

-continued
31
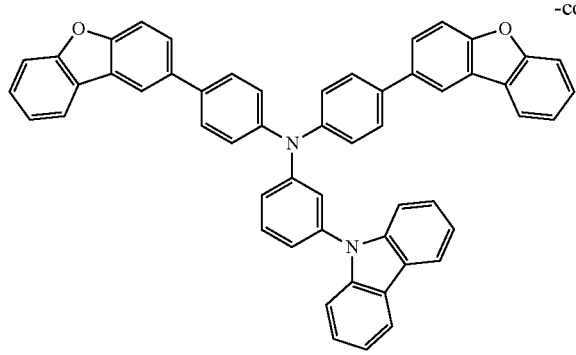
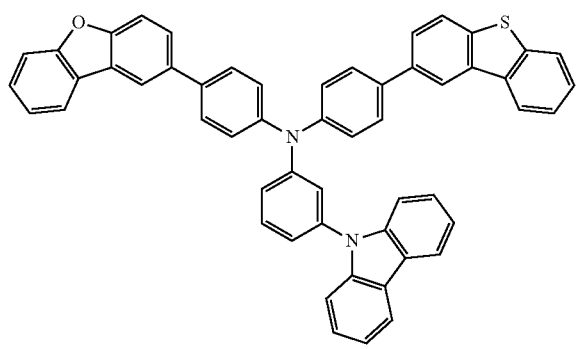
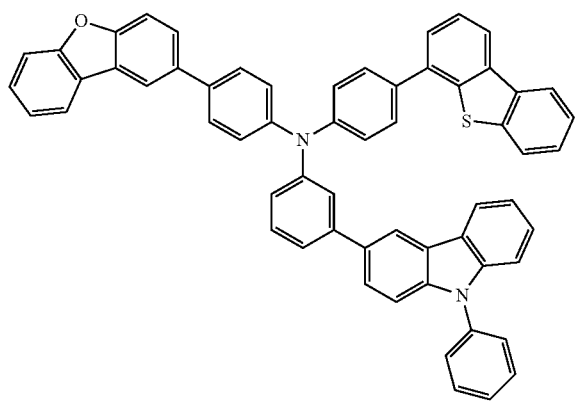
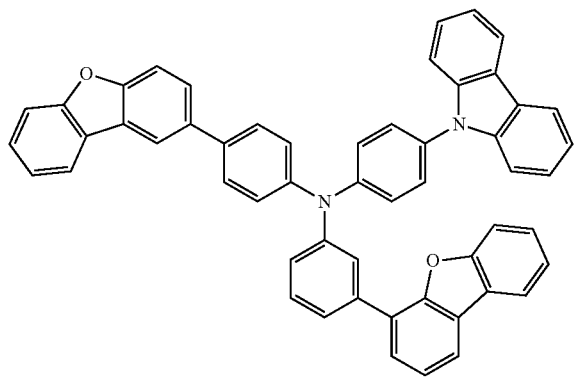
32
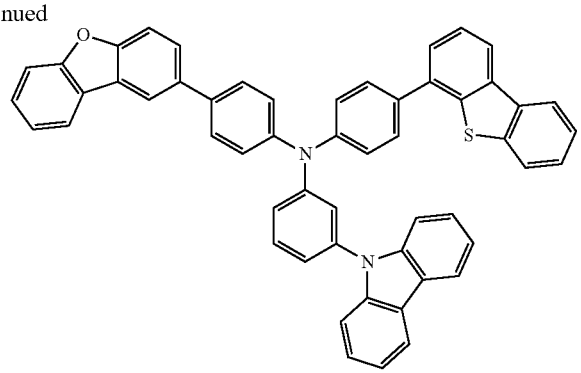
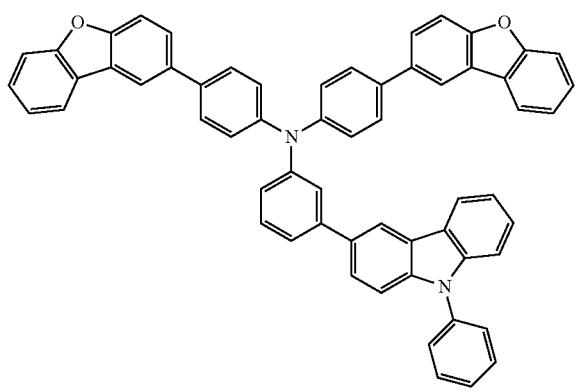
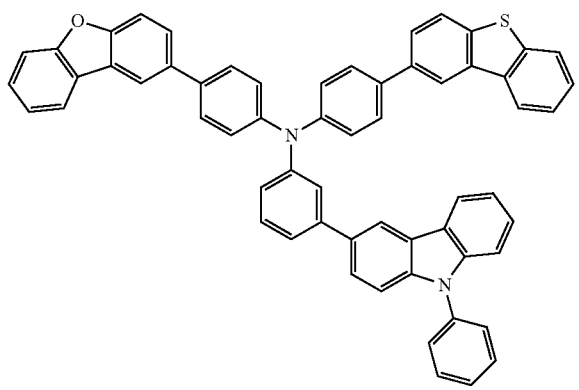
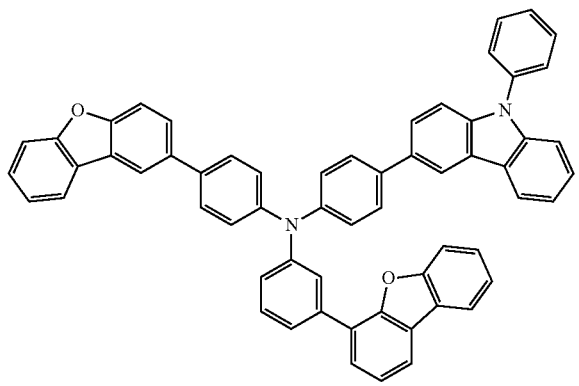

| 33 | 34 |
|---|---|
| 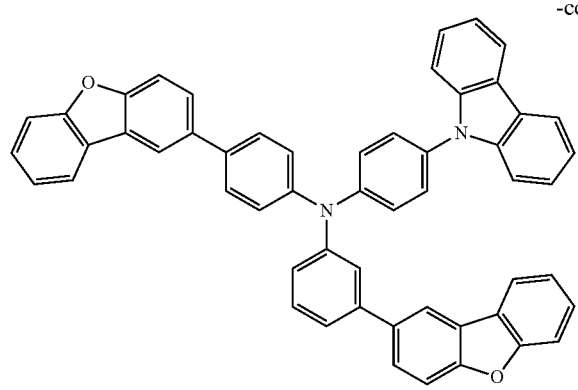 | 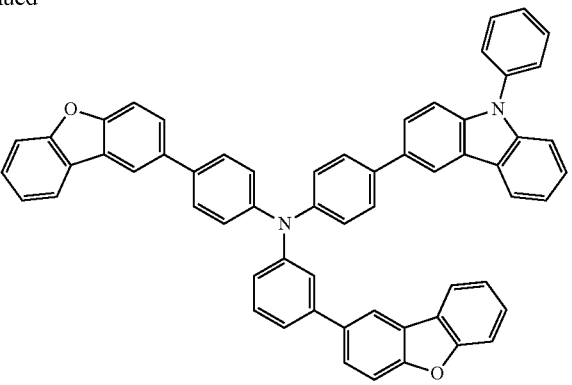 |
| 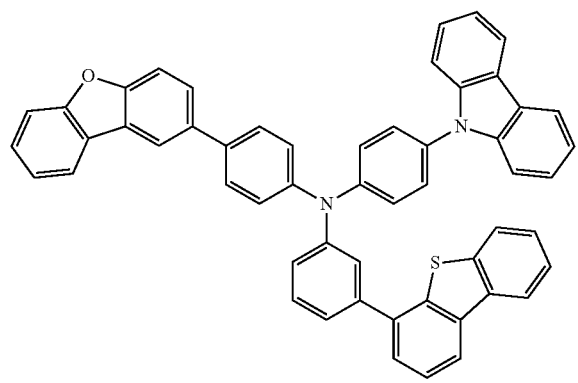 | 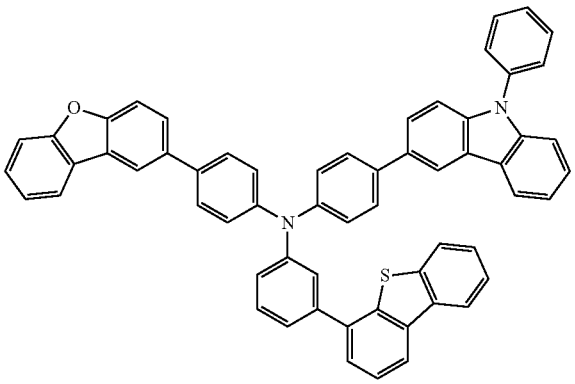 |
| 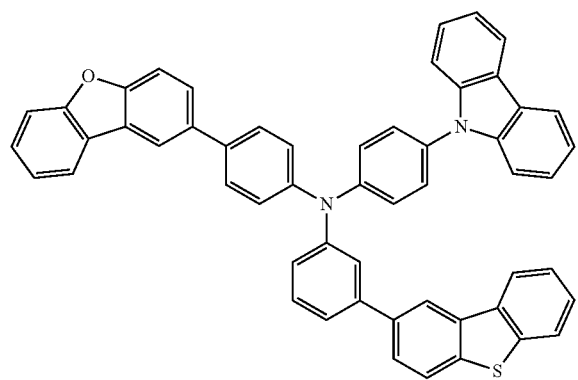 | 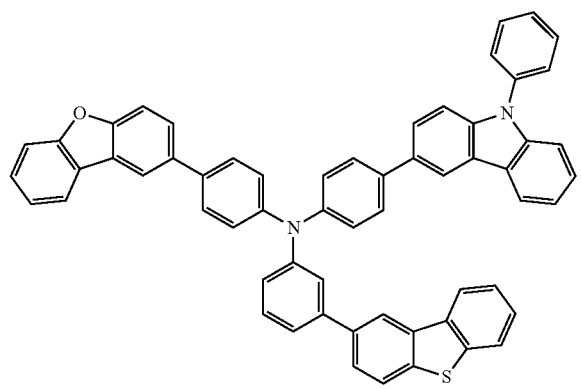 |
| 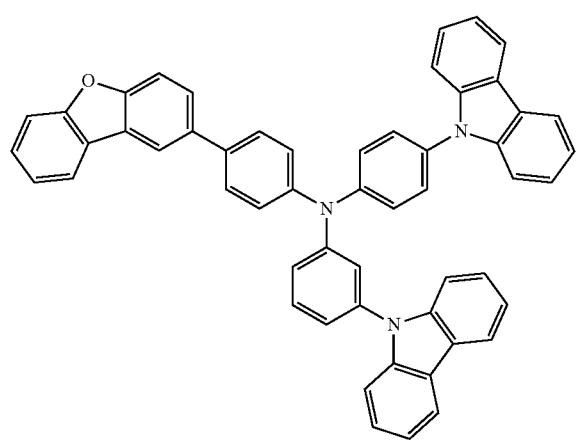 | 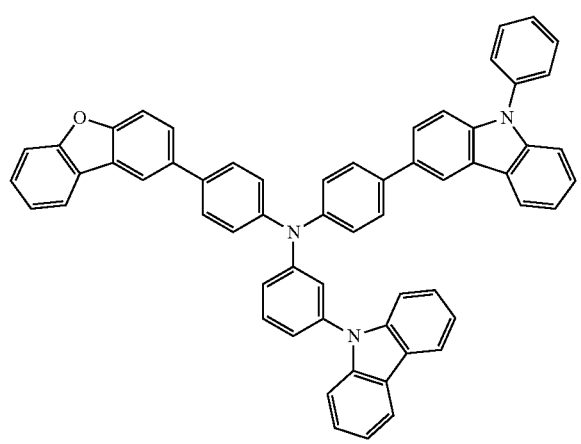 |

-continued
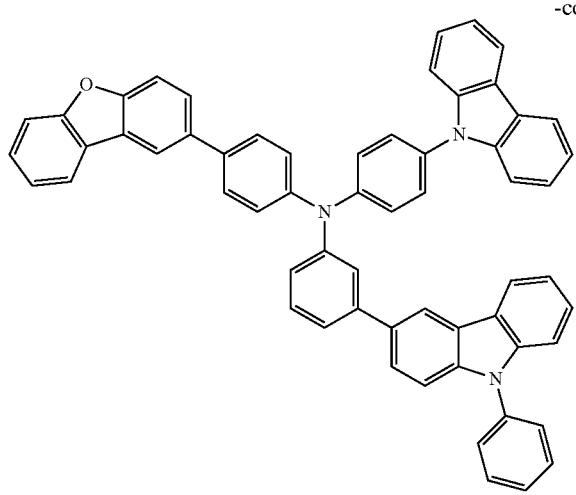
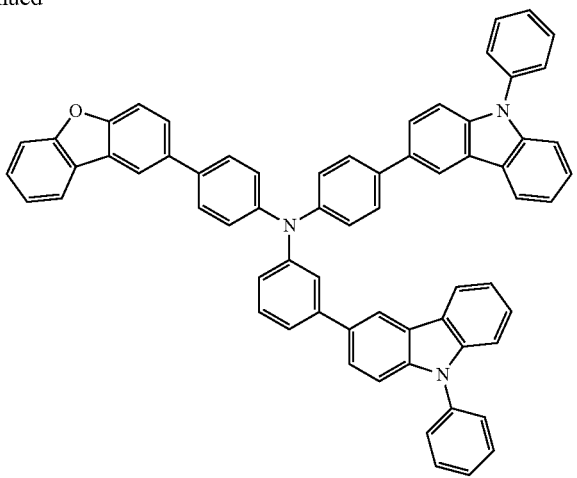
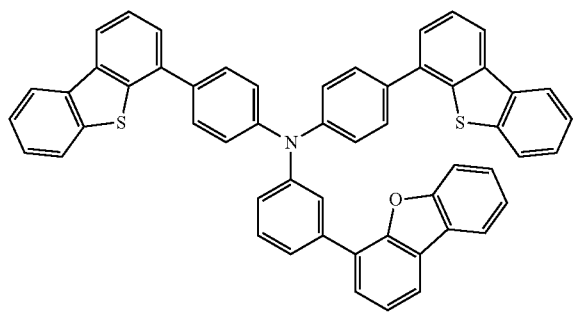
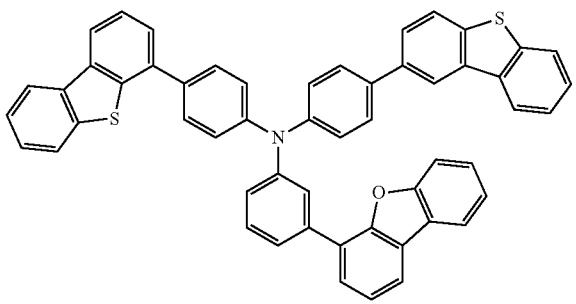
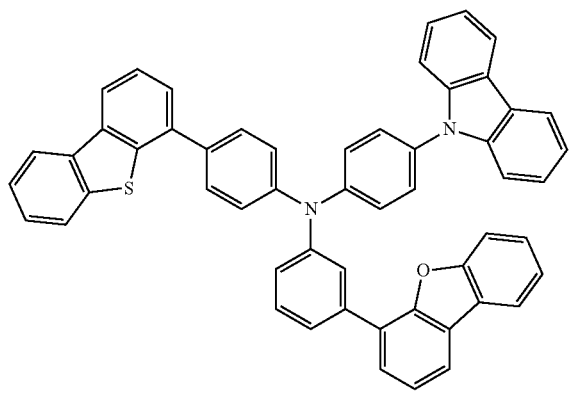
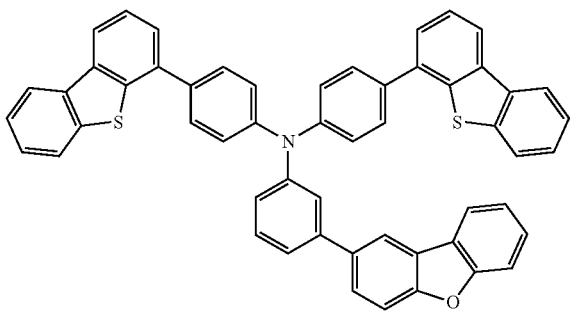
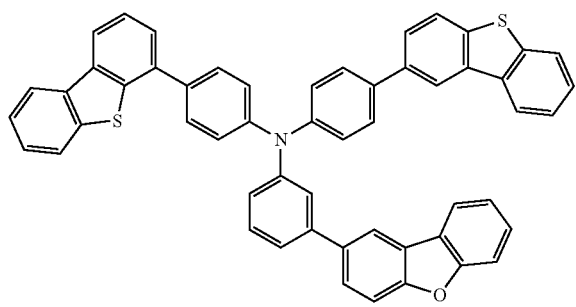
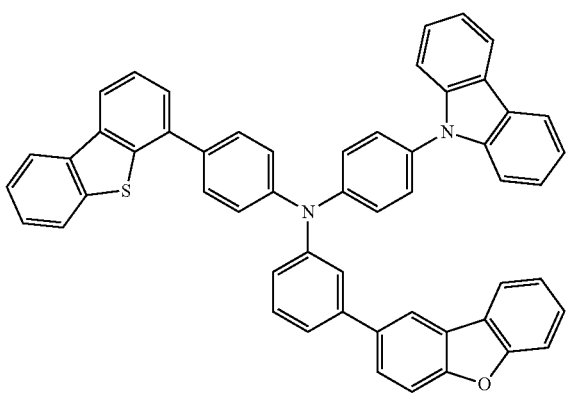

-continued
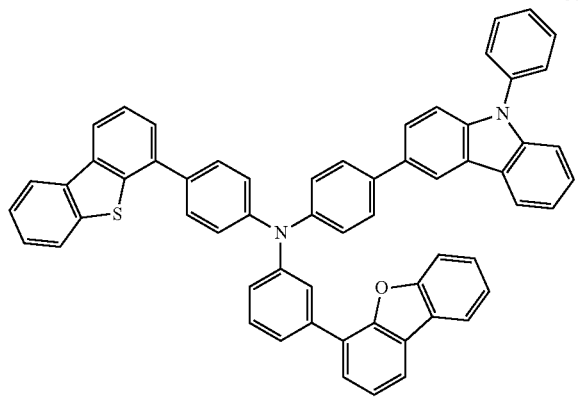
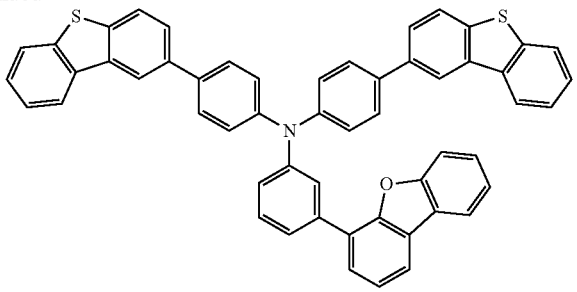
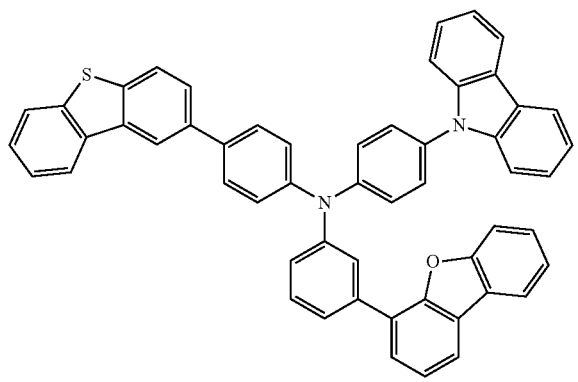
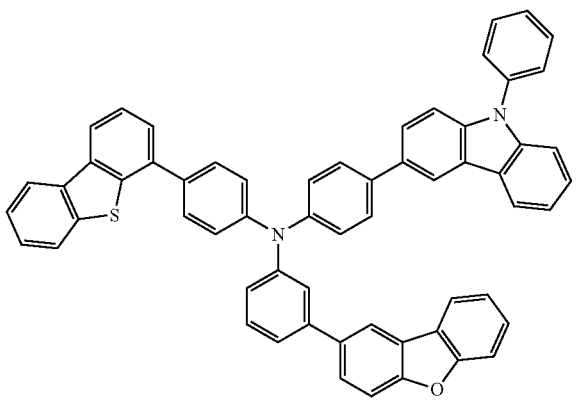
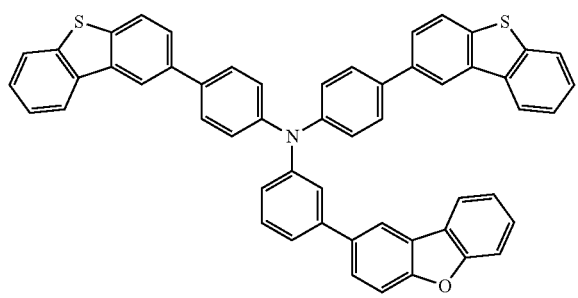
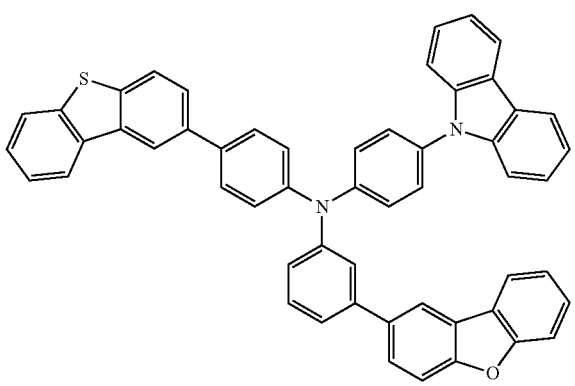
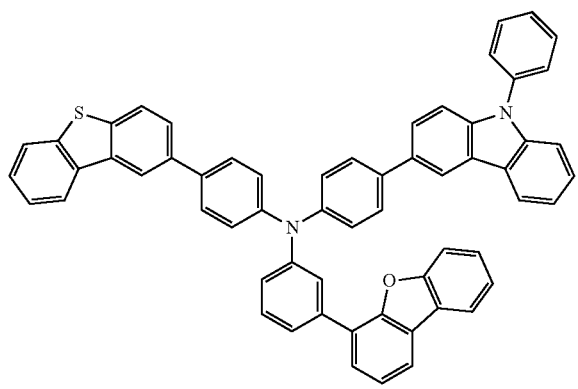
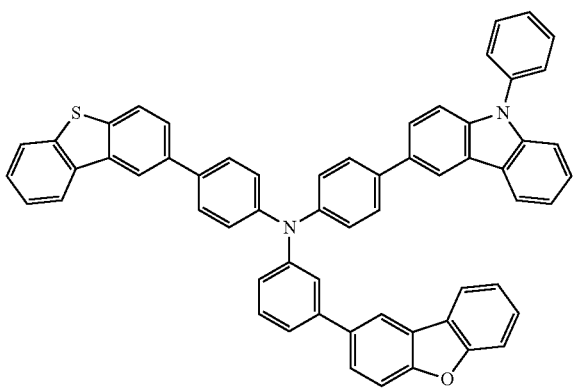

-continued
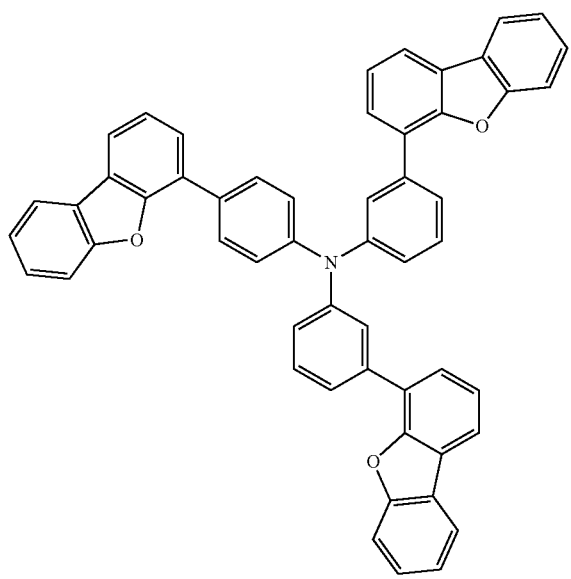
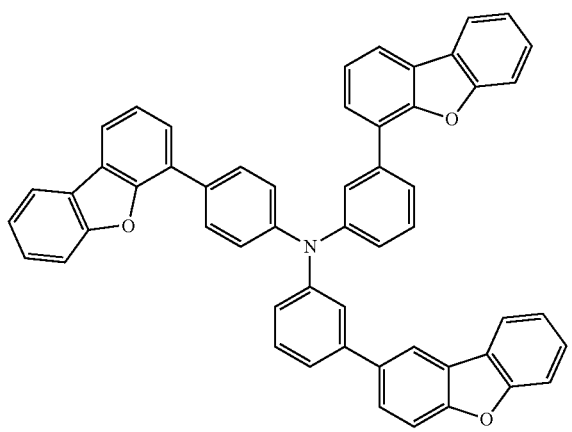
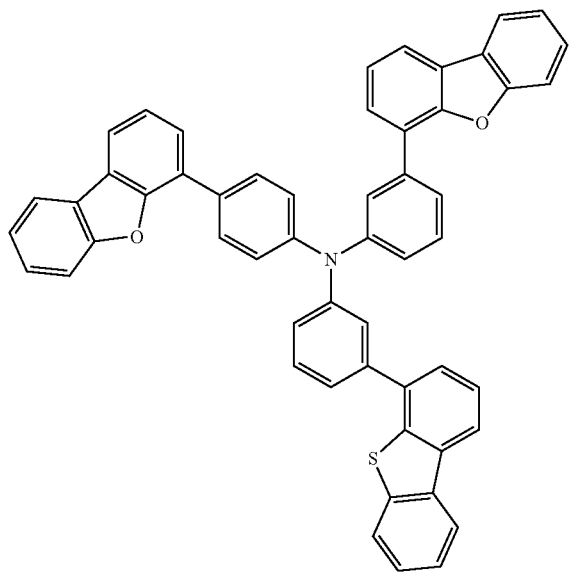
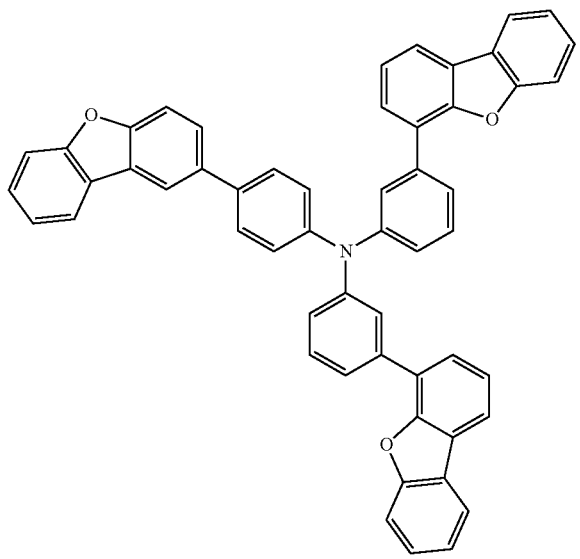
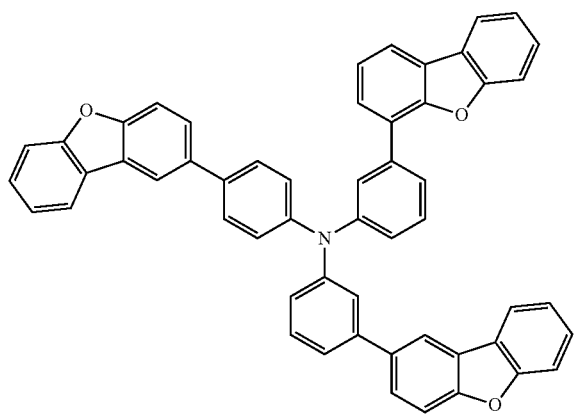
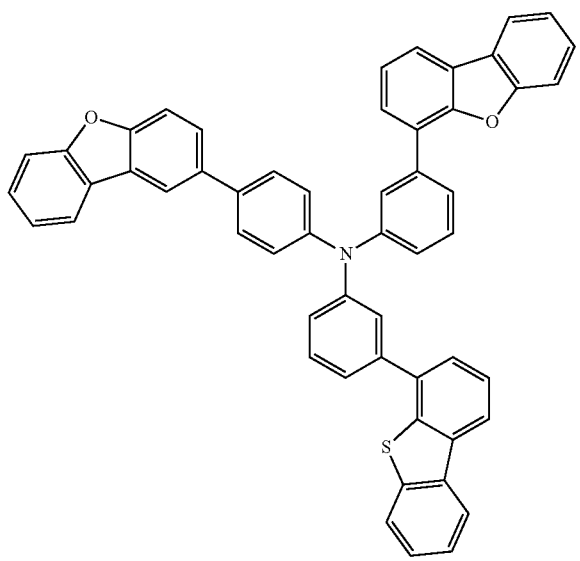

-continued
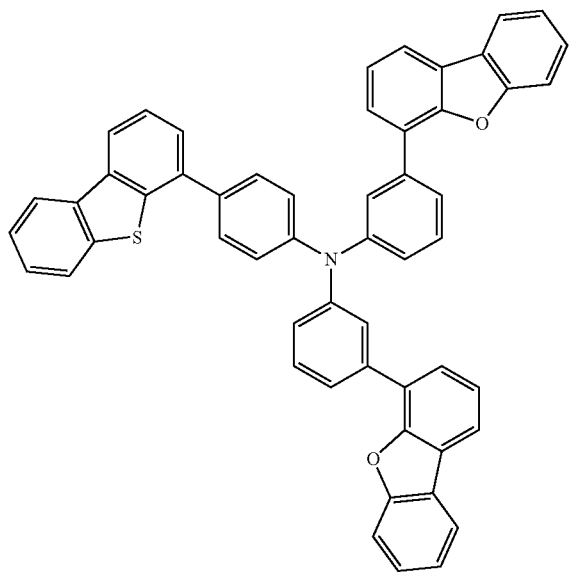
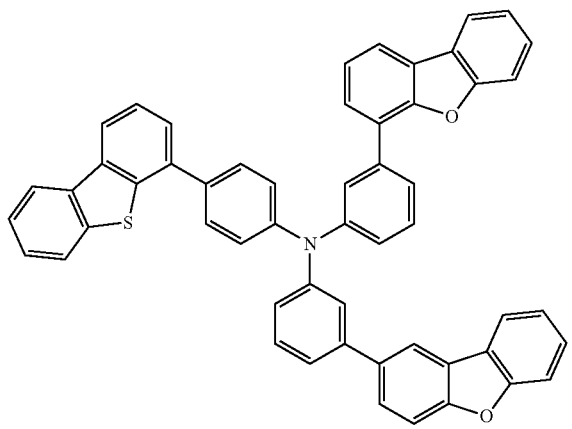
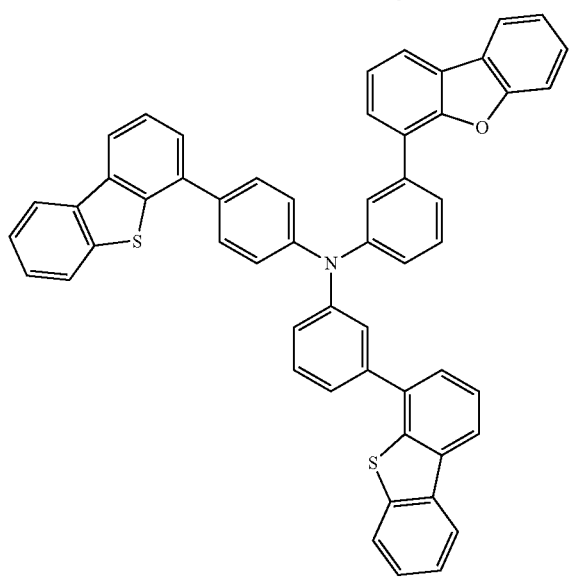
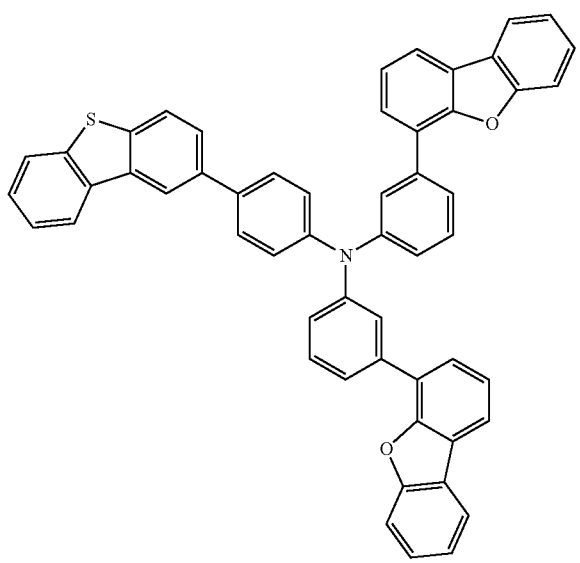
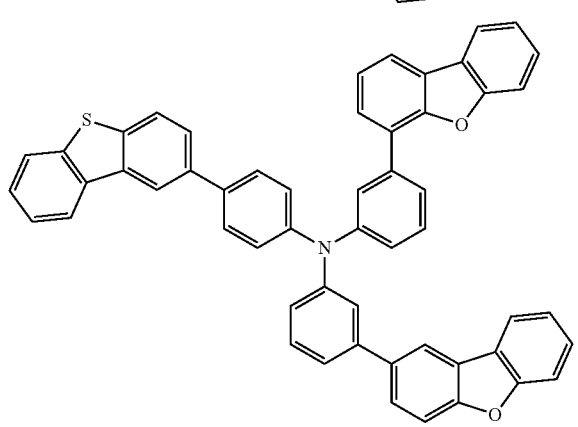
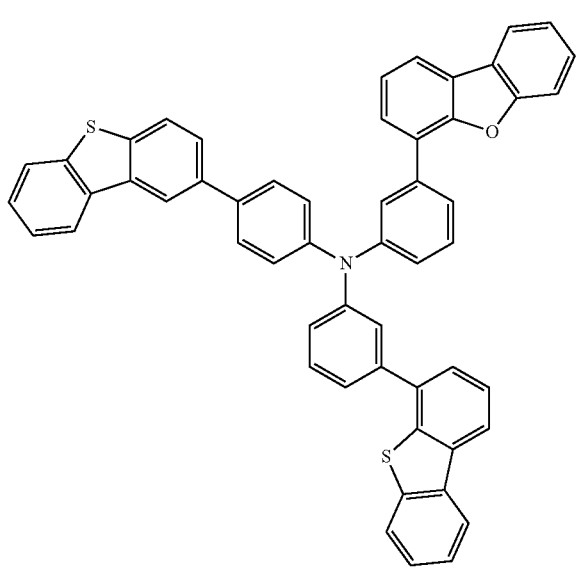

-continued
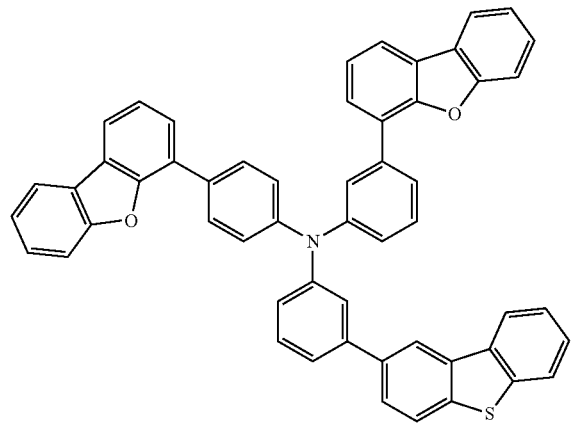
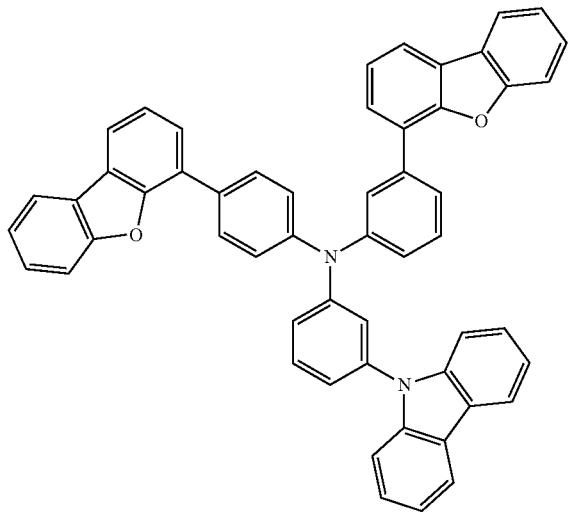
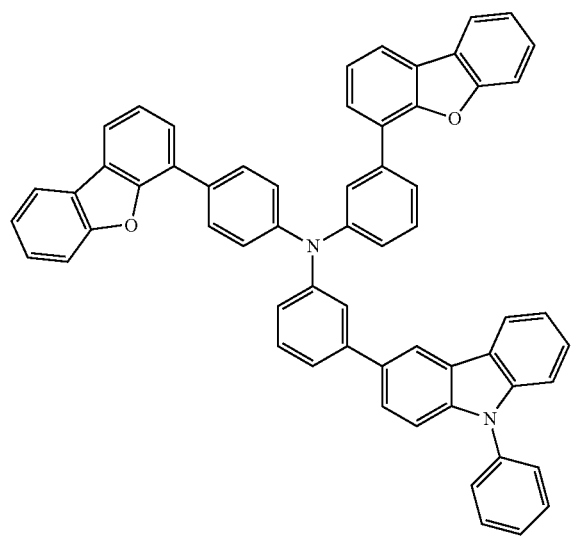
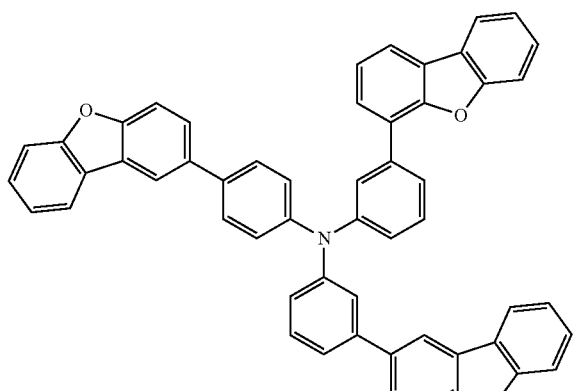
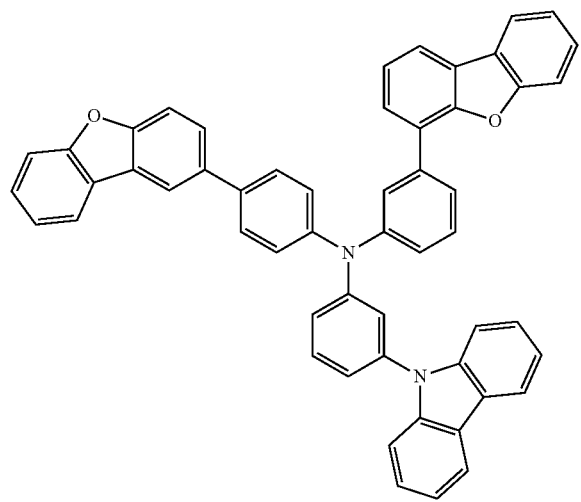
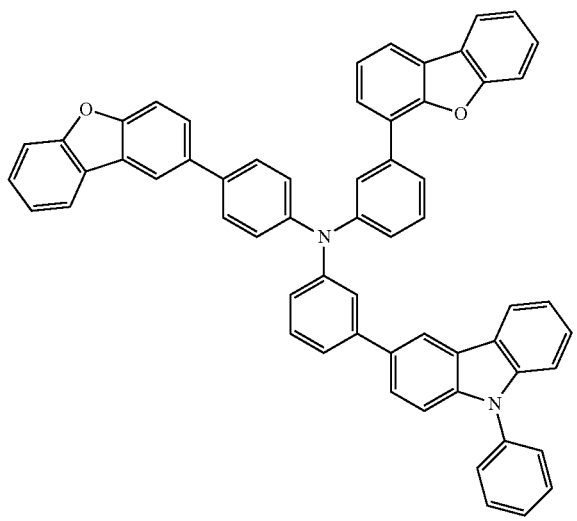

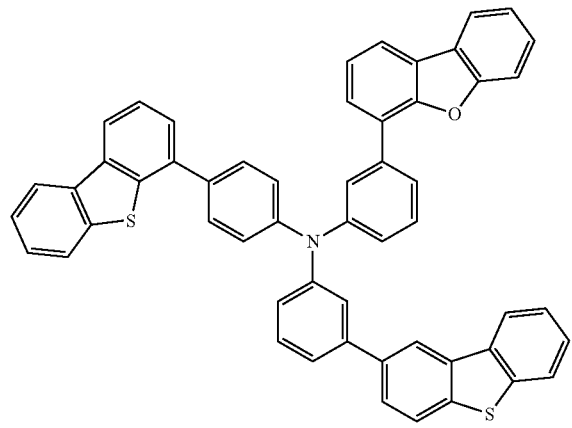
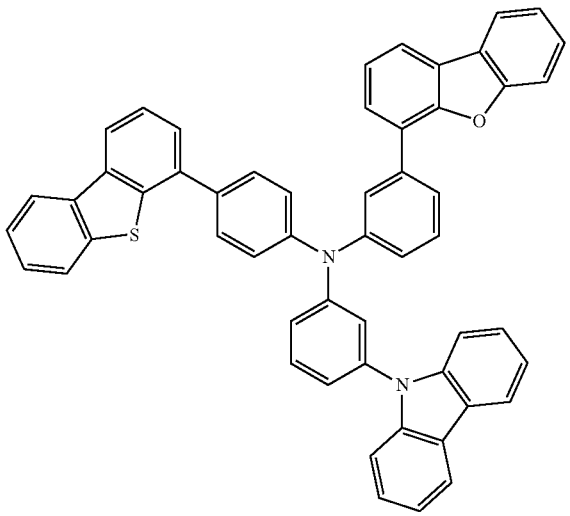
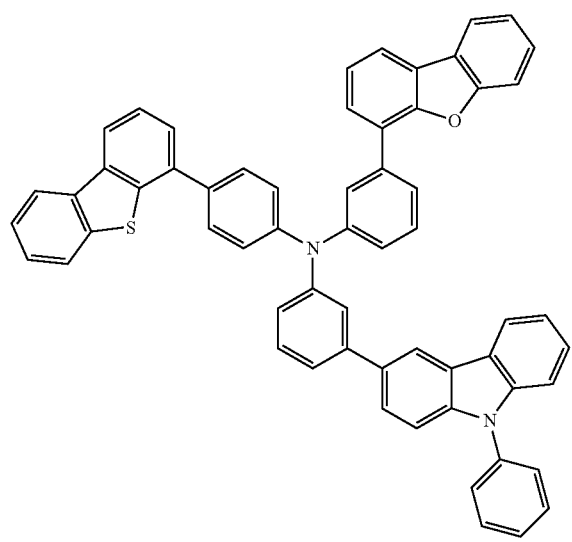
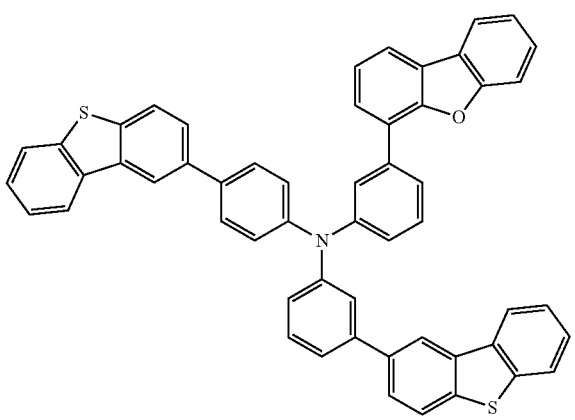
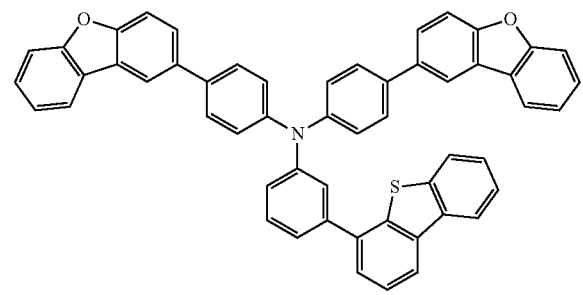

-continued
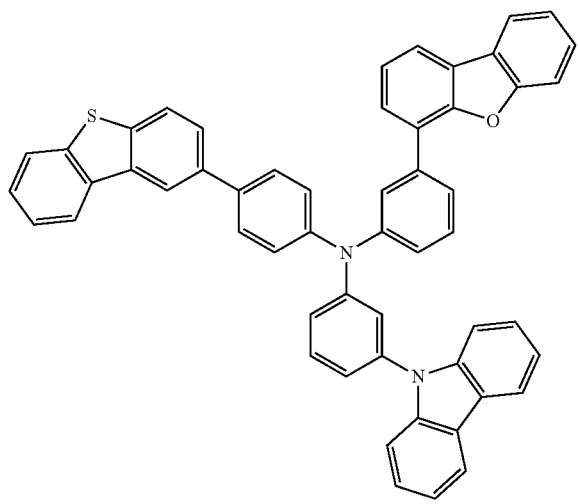
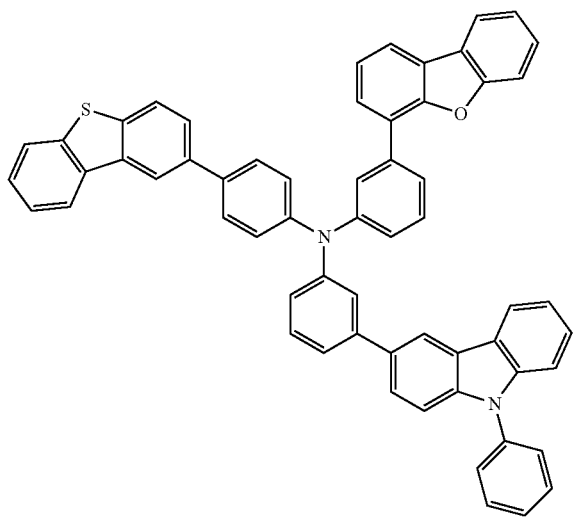
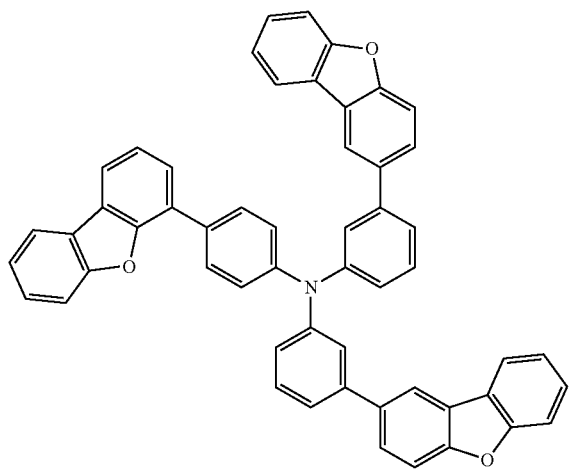
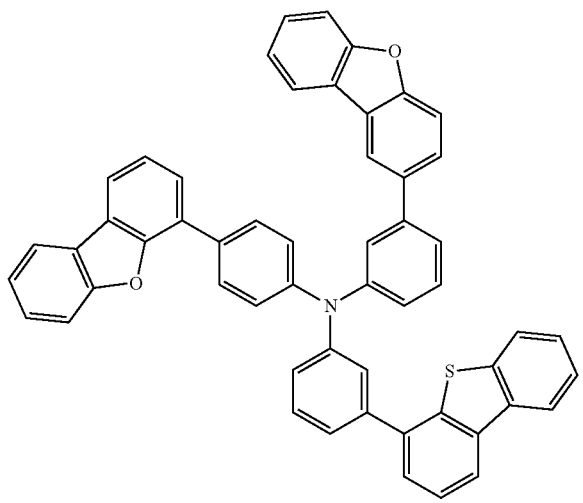
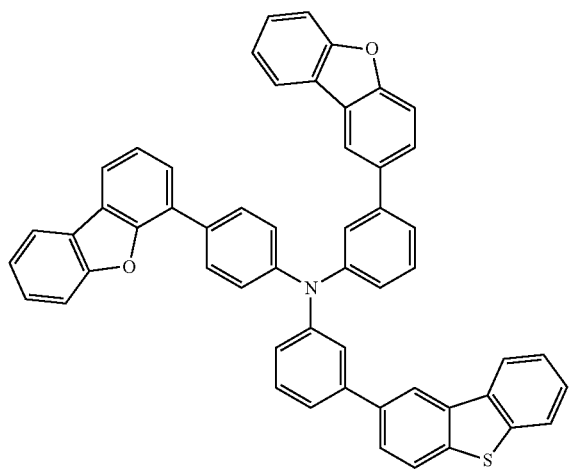
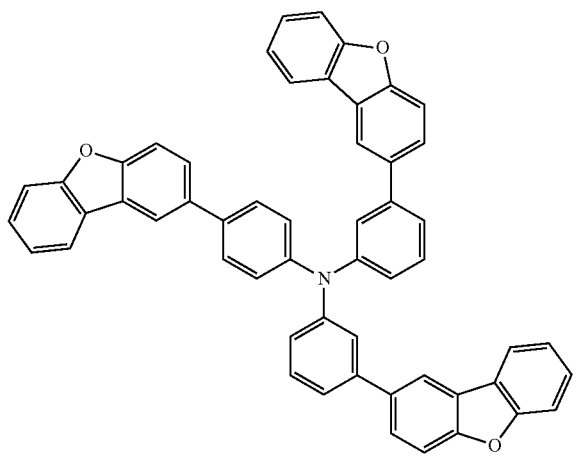

-continued
49
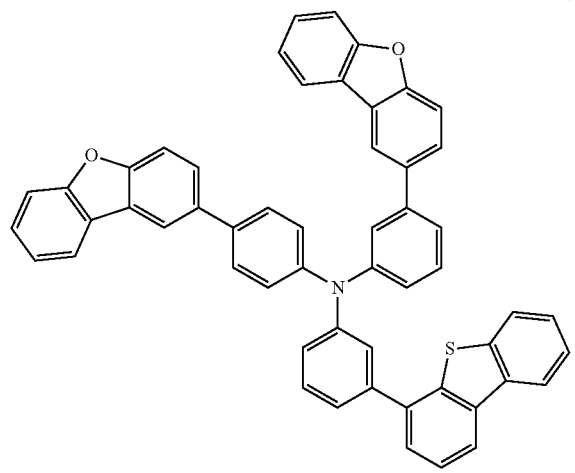
50
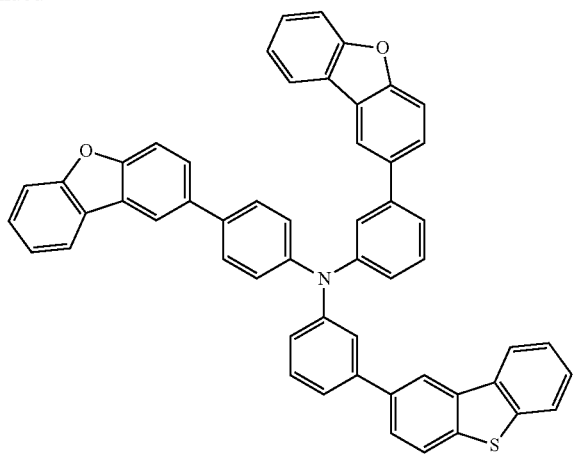
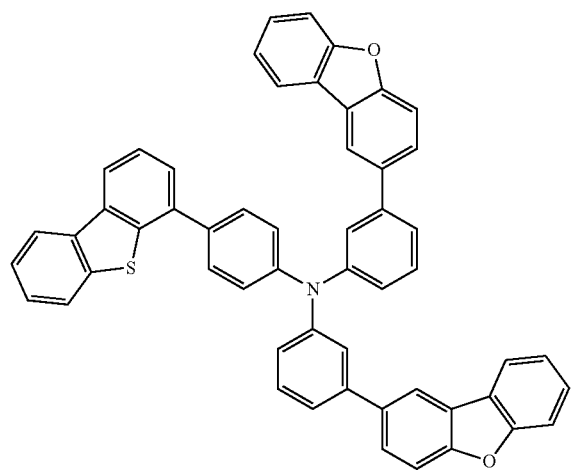
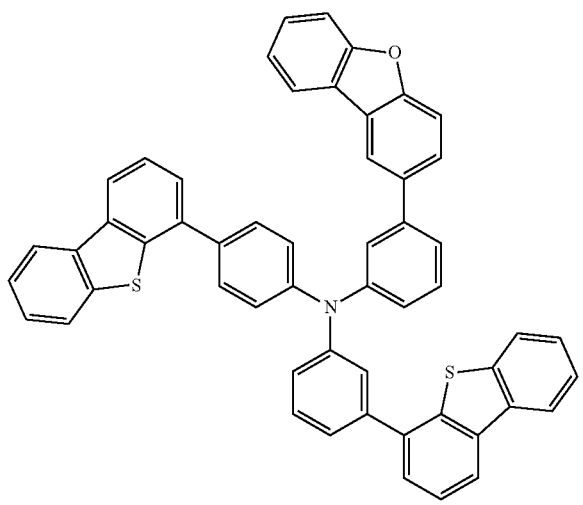
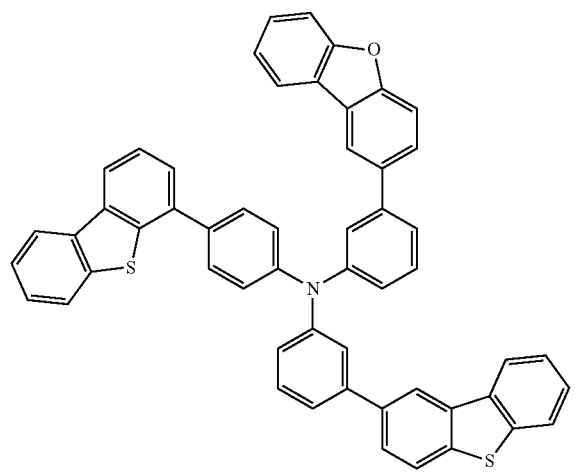
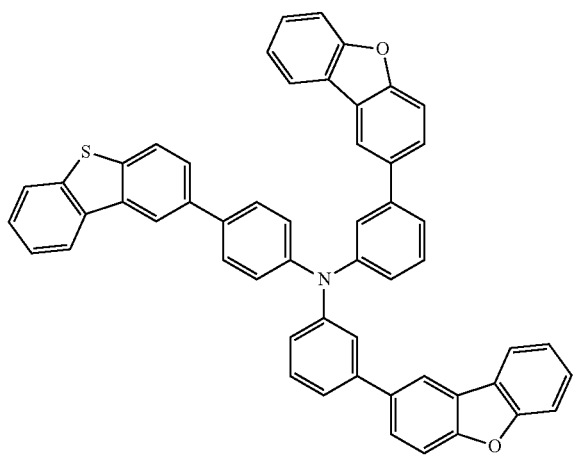

-continued
51
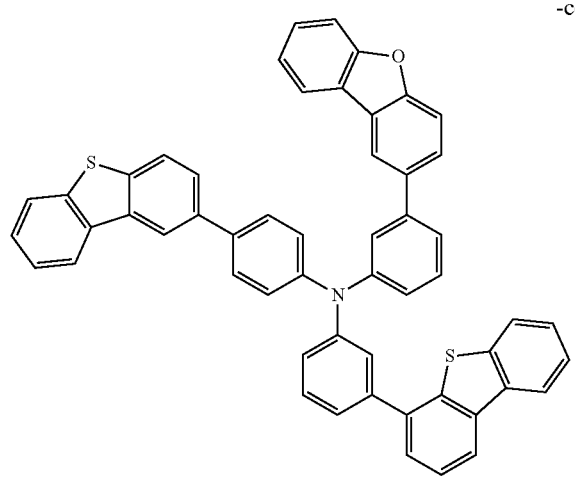
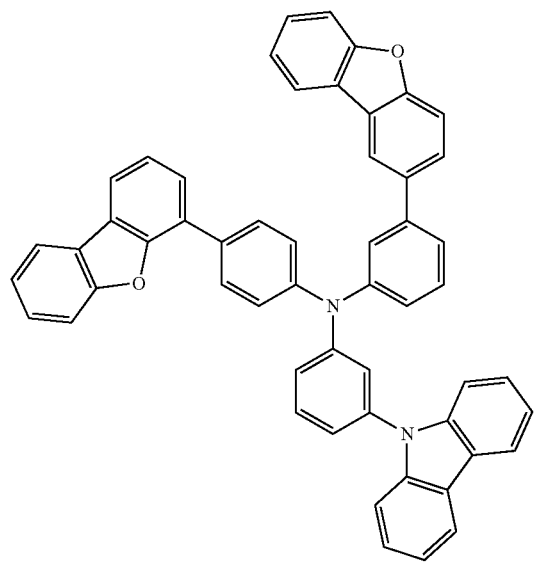
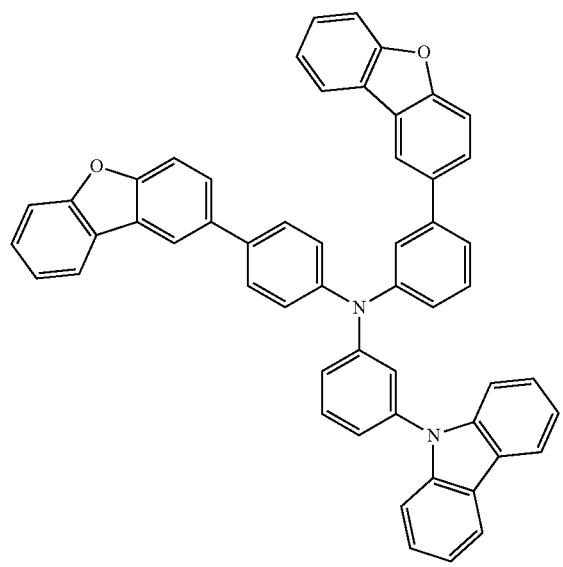
52
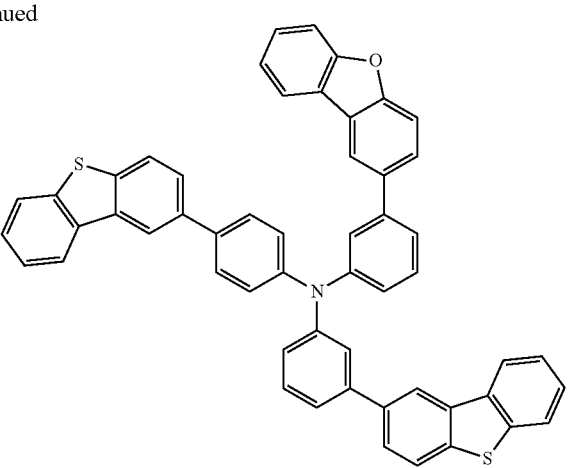
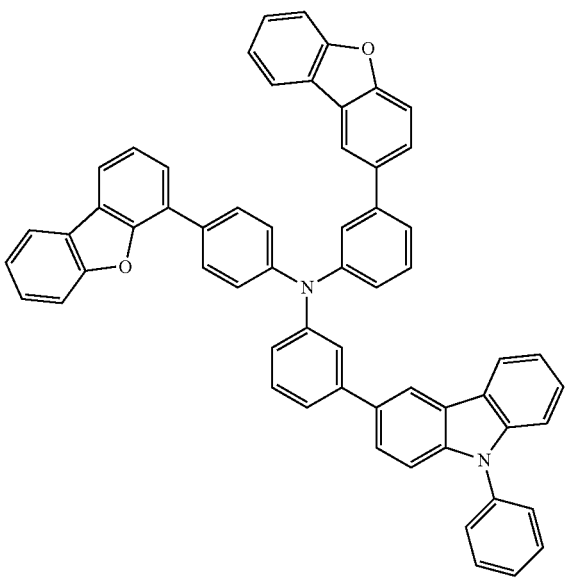
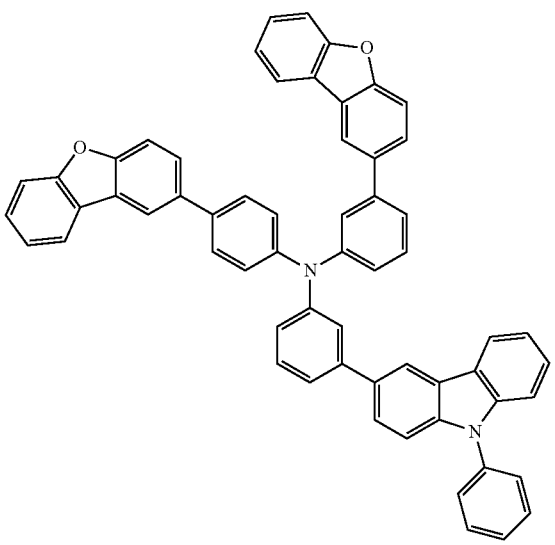

-continued
53
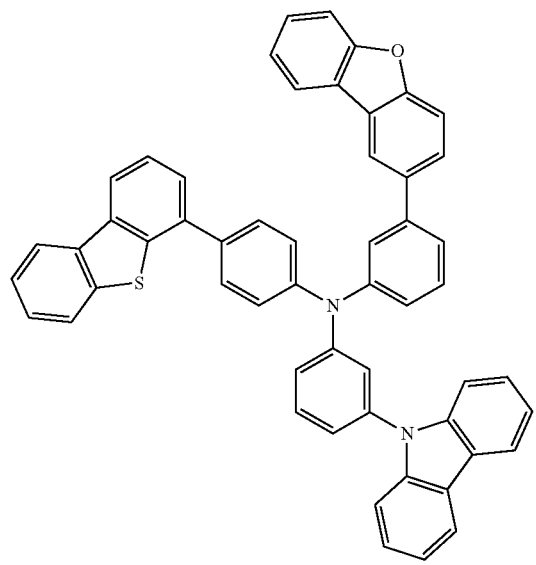
54
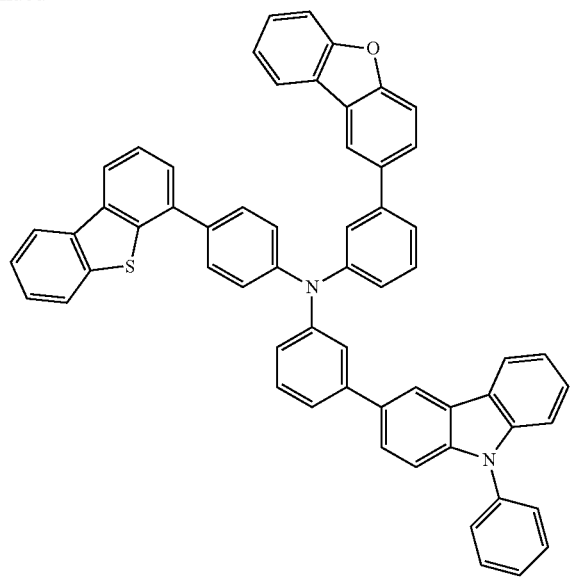
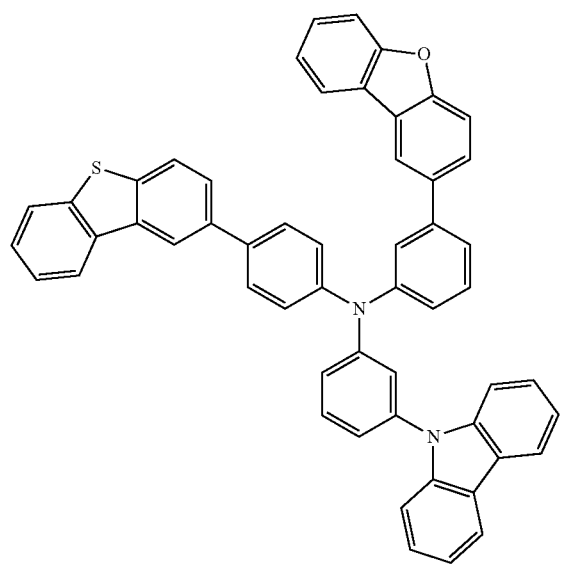
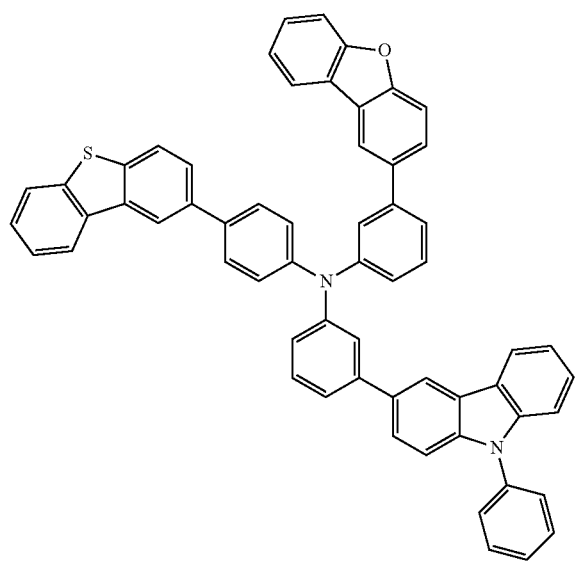
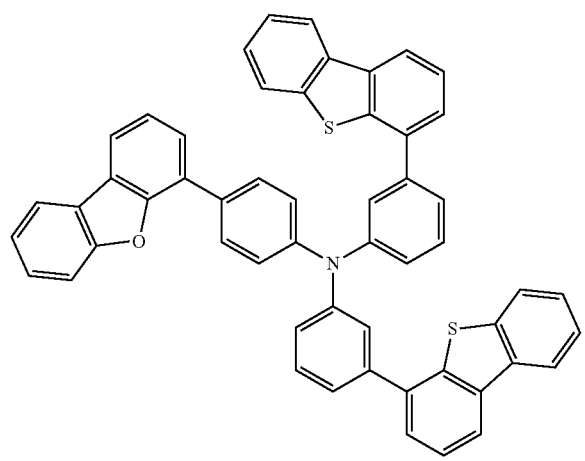
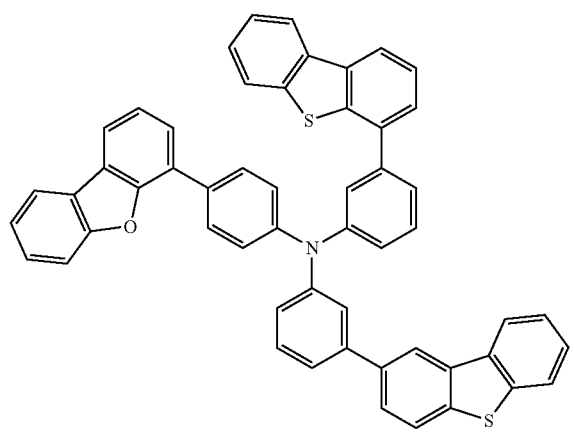

-continued
55
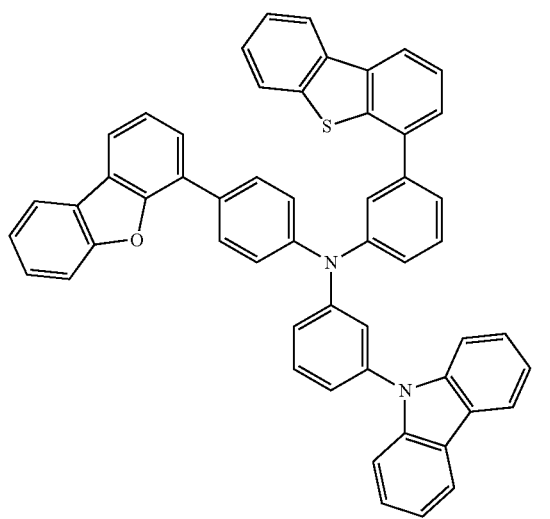
56
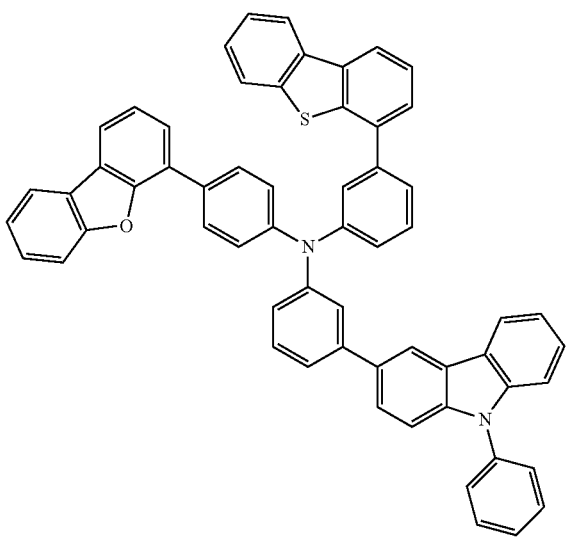
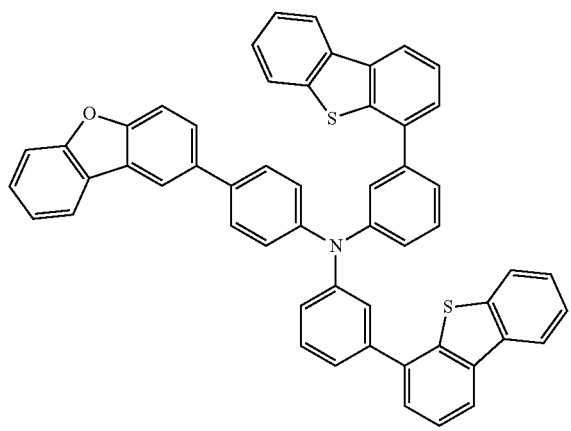
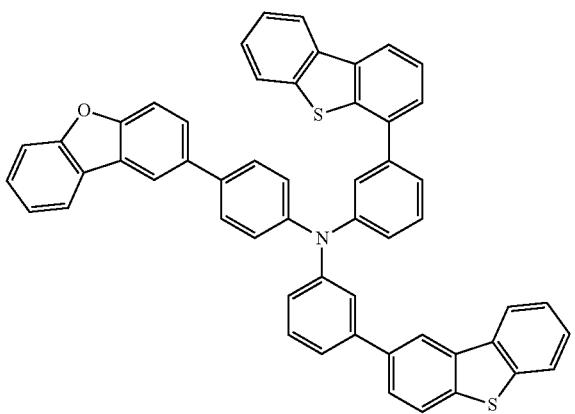
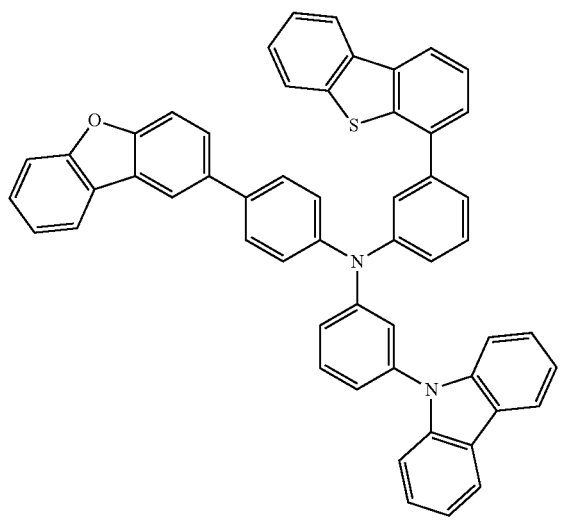
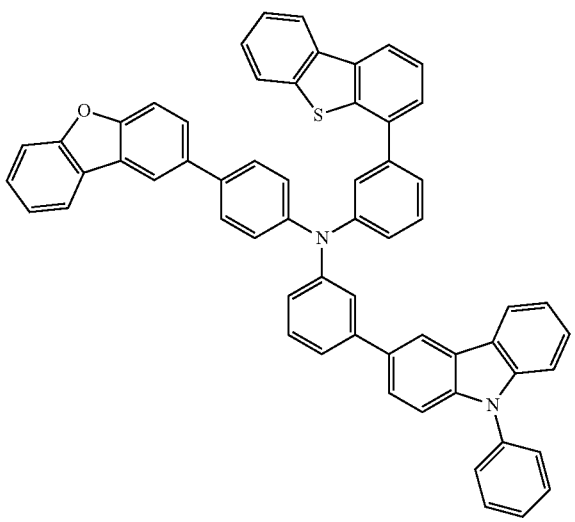

-continued
57
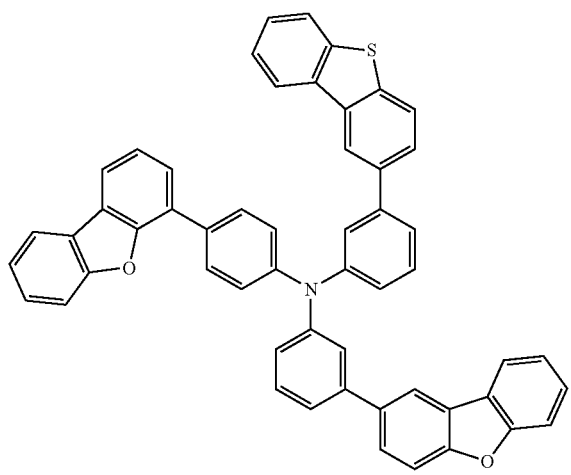
58
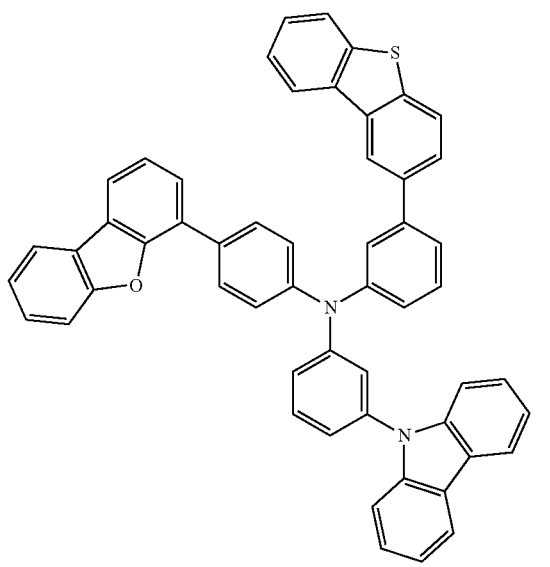
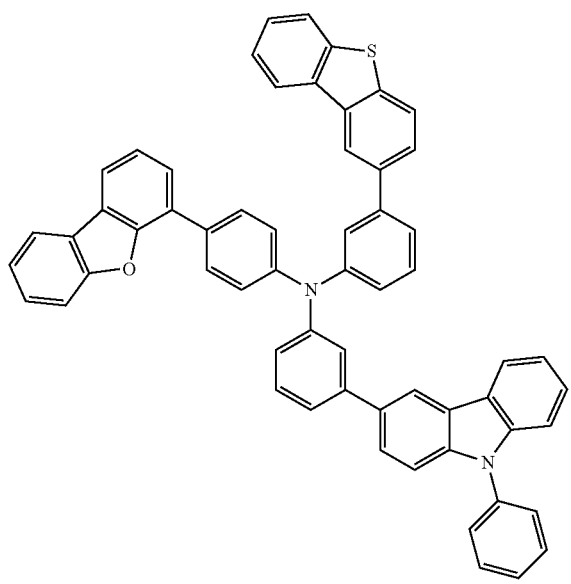
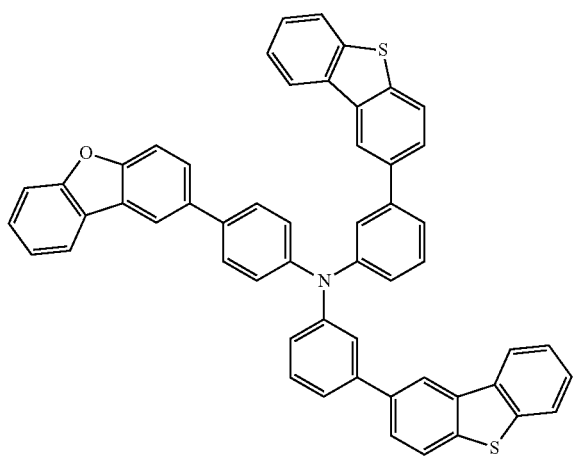
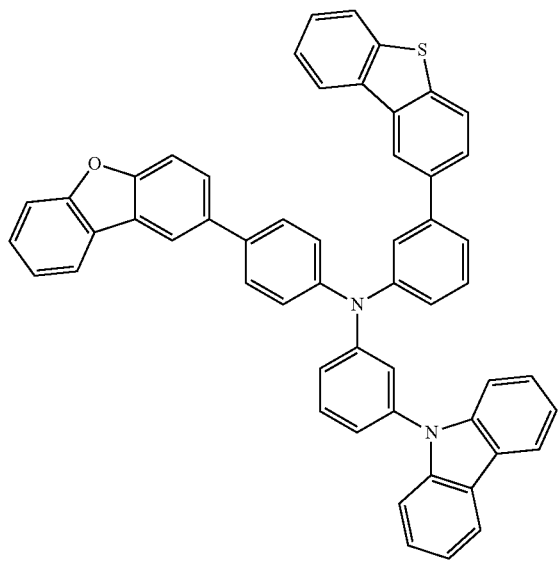
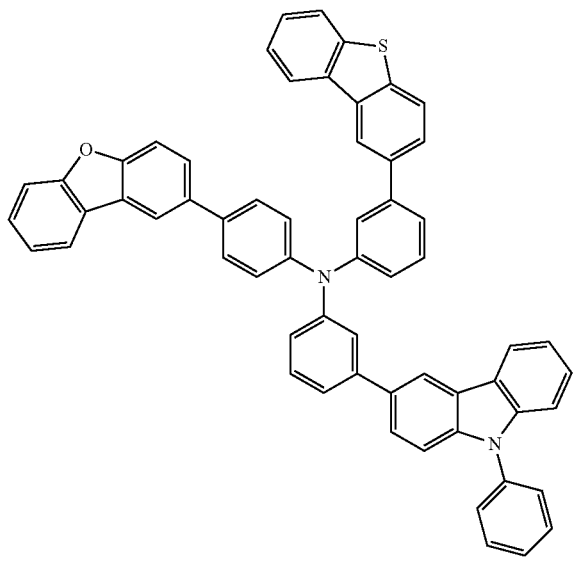

59 60
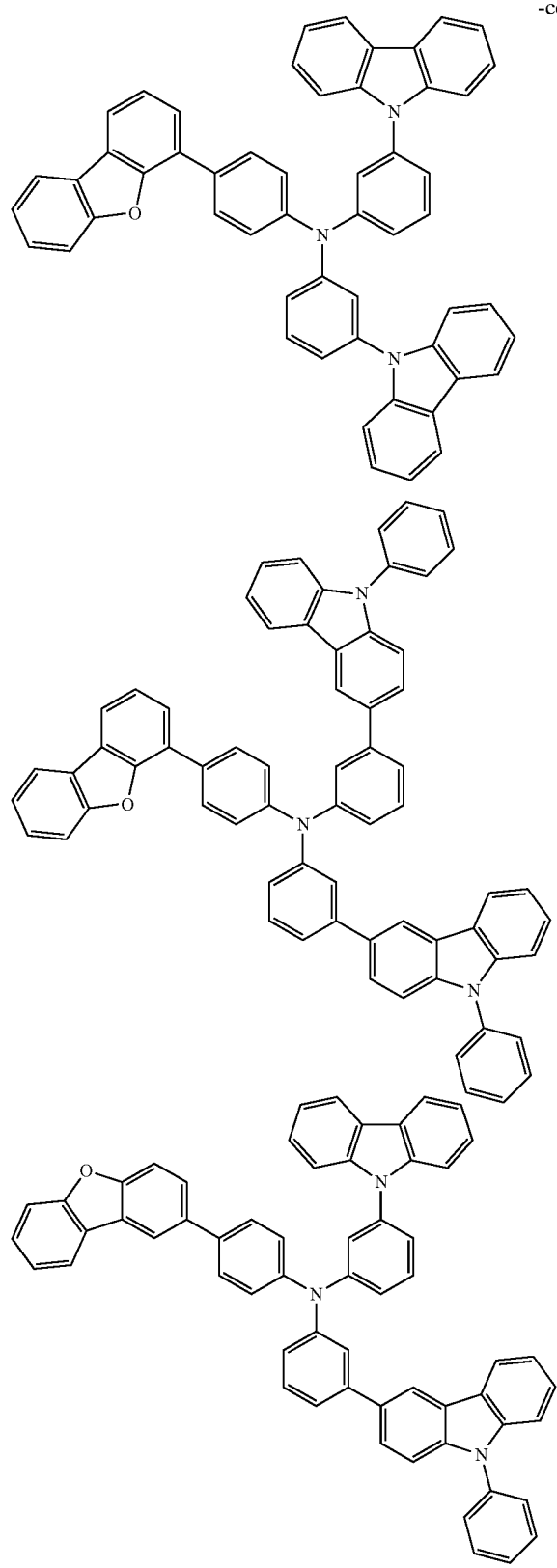
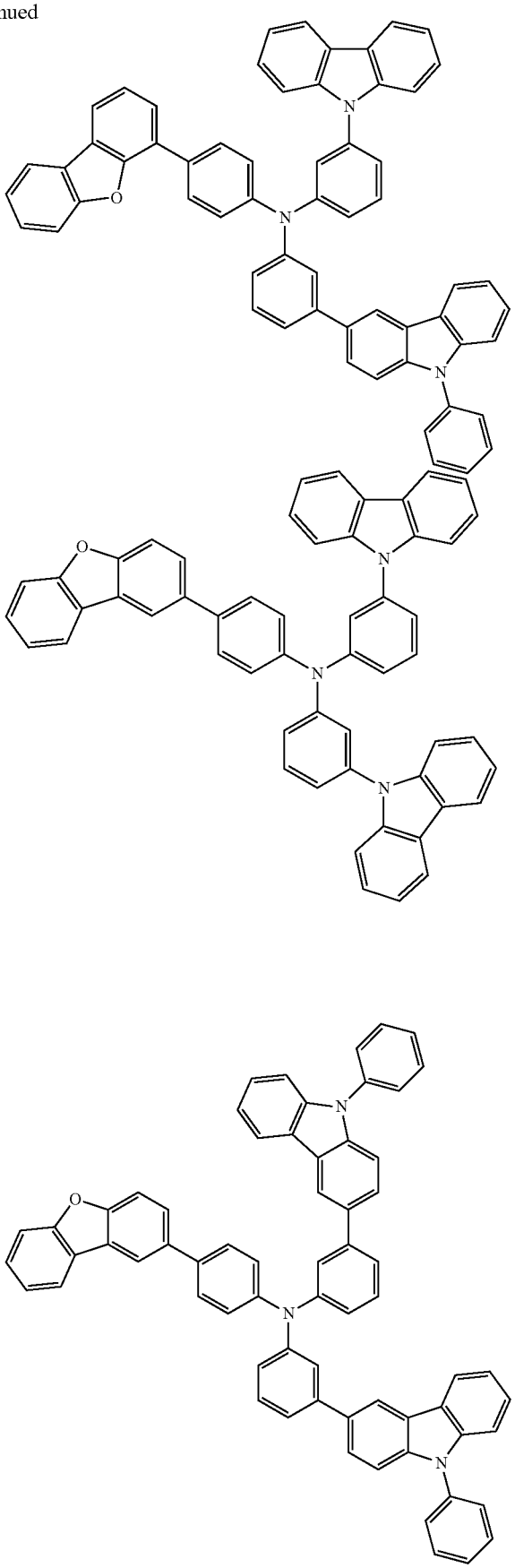
-continued

61
-continued
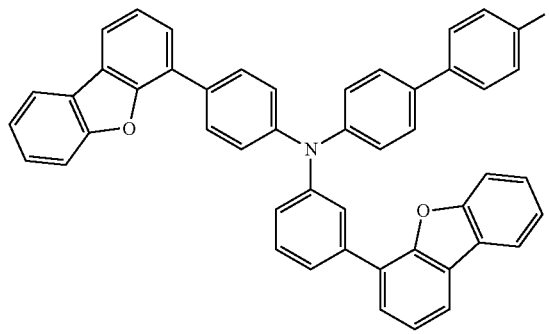
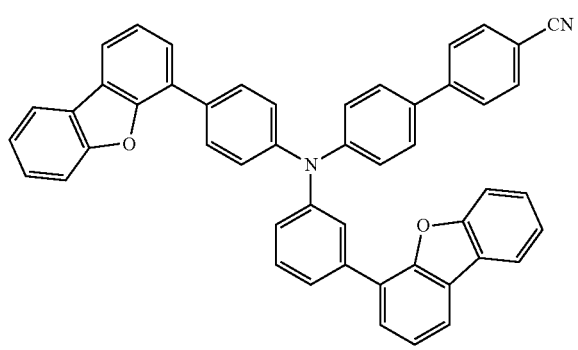
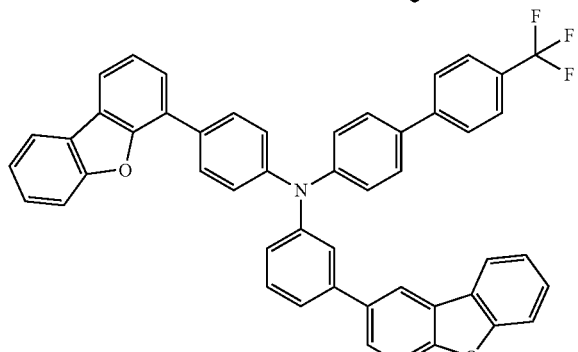
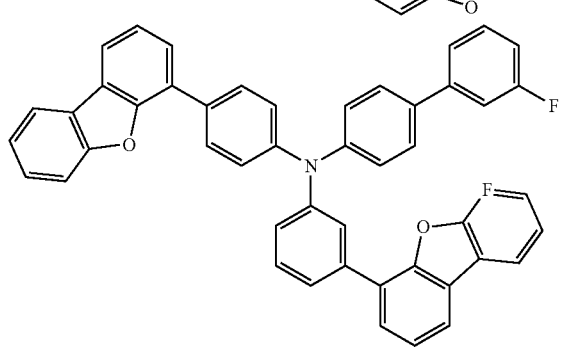
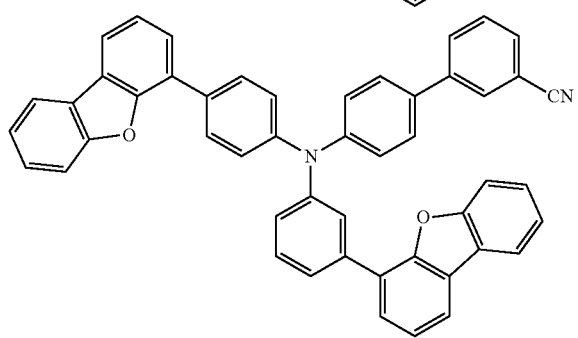
62
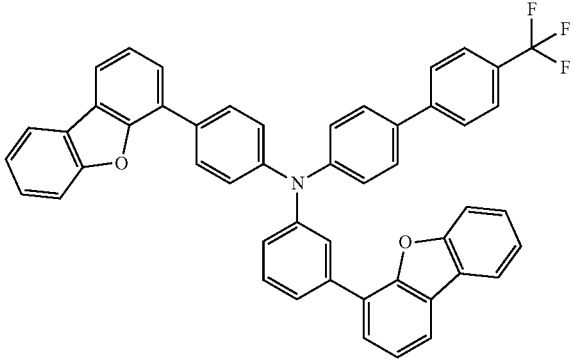
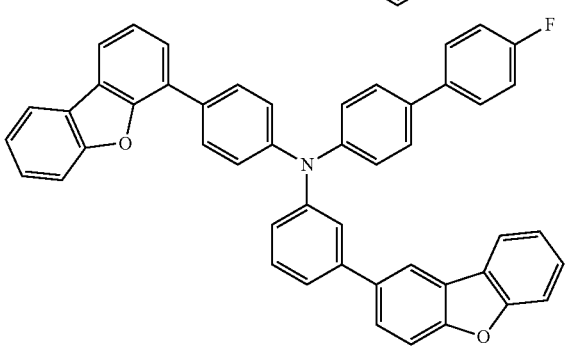
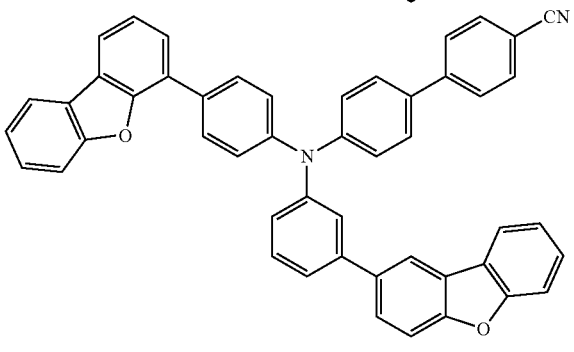
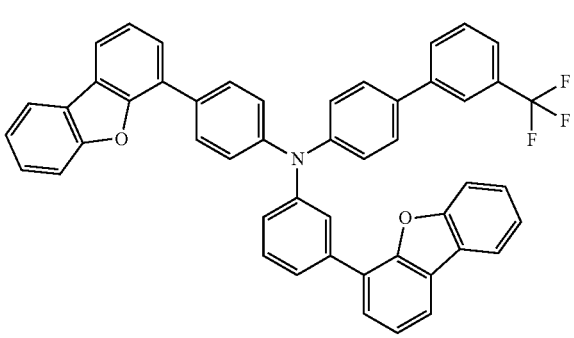
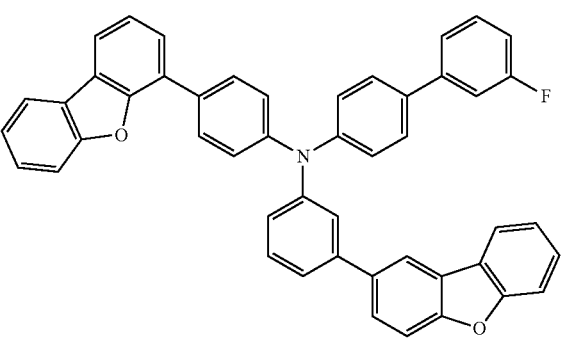

63     64
-continued
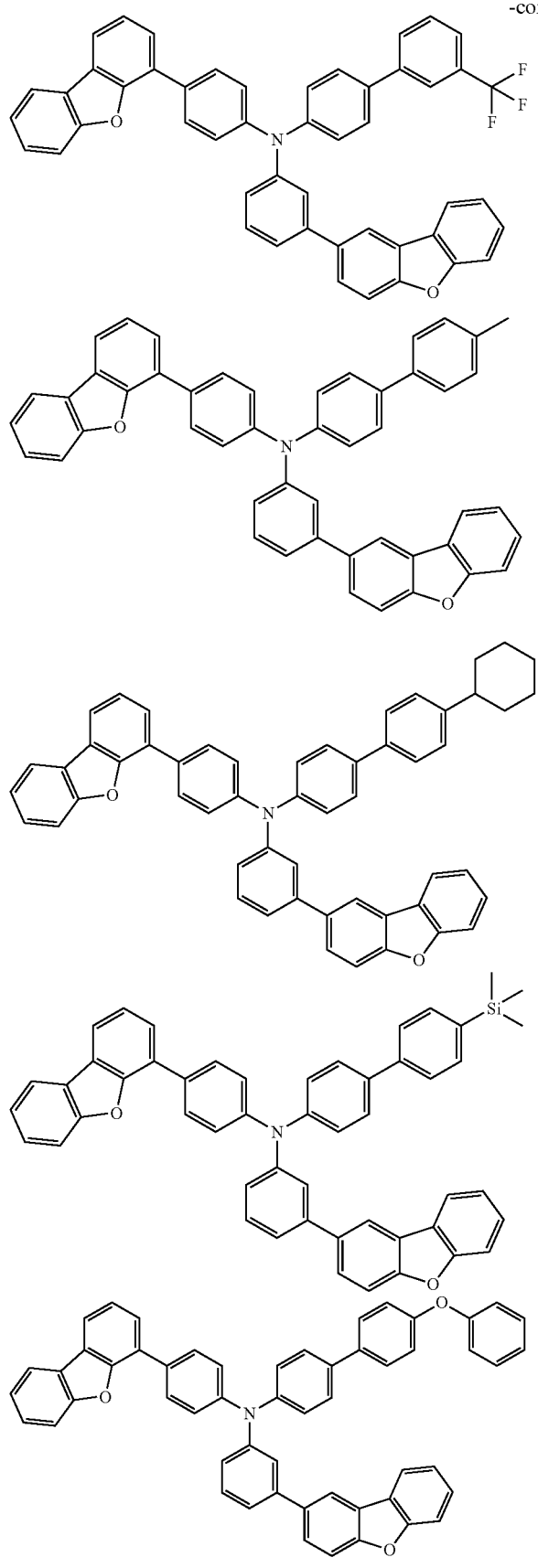

-continued
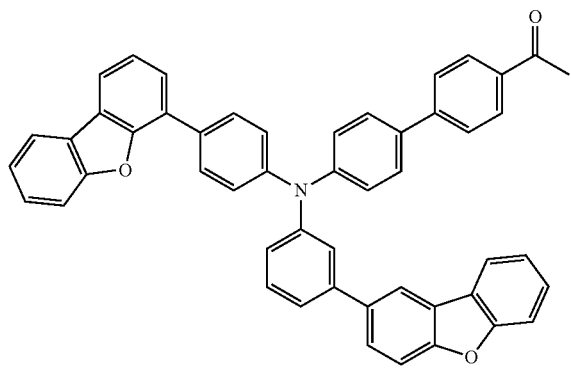
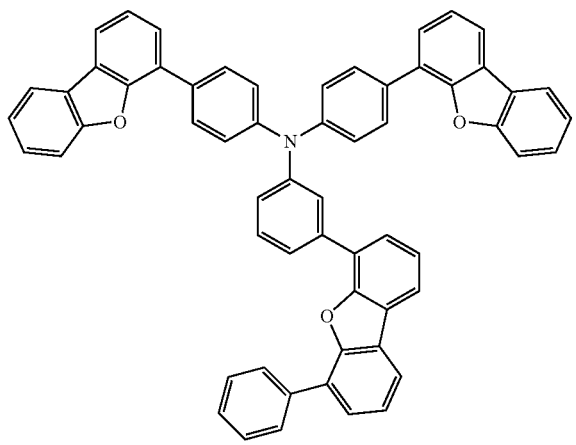
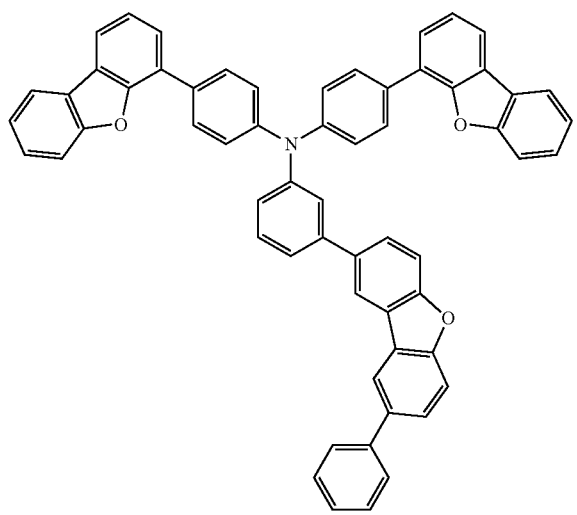
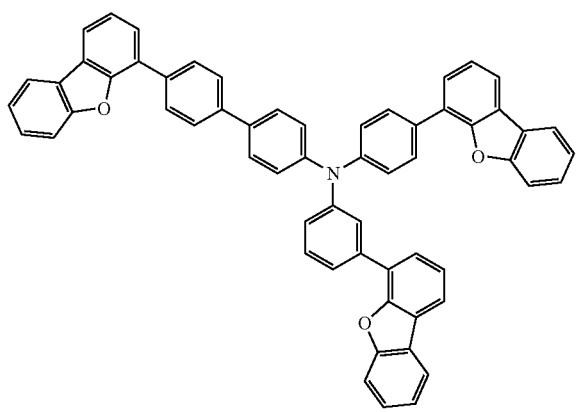
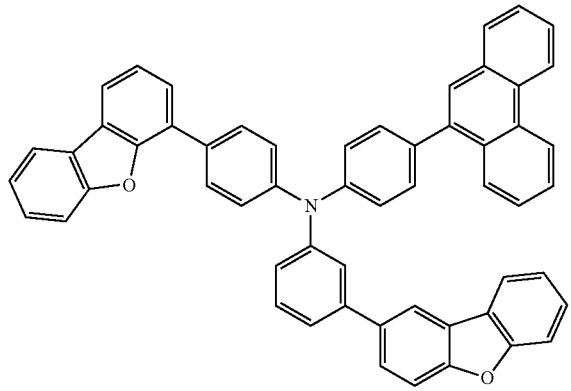
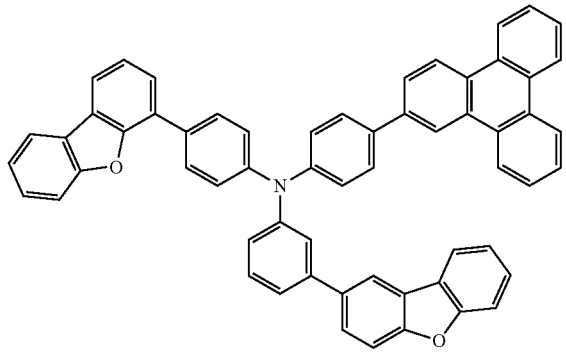

67
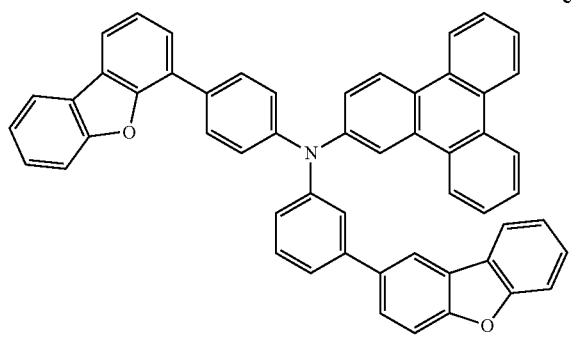
-continued
68
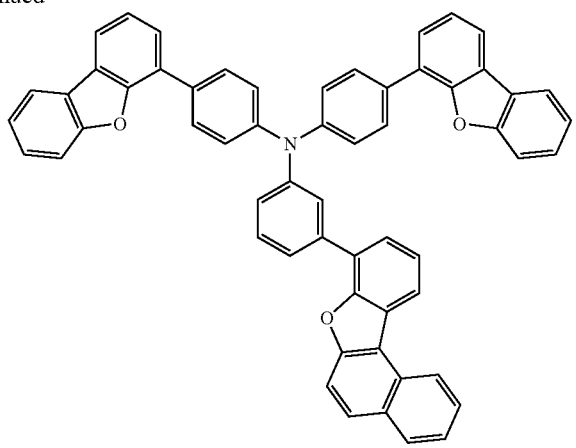
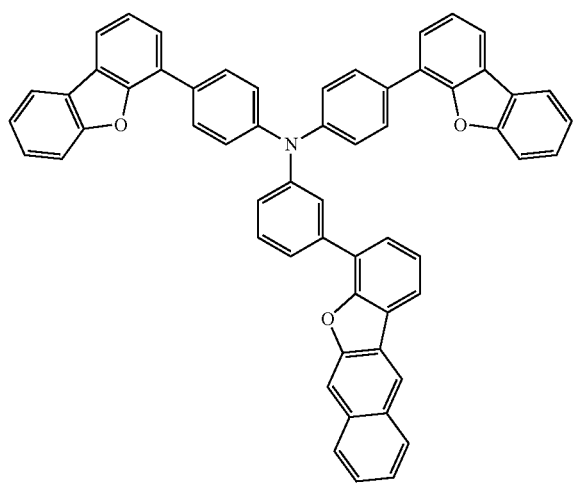
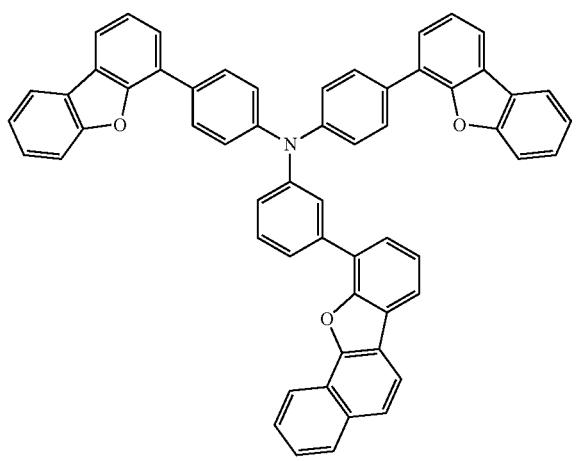
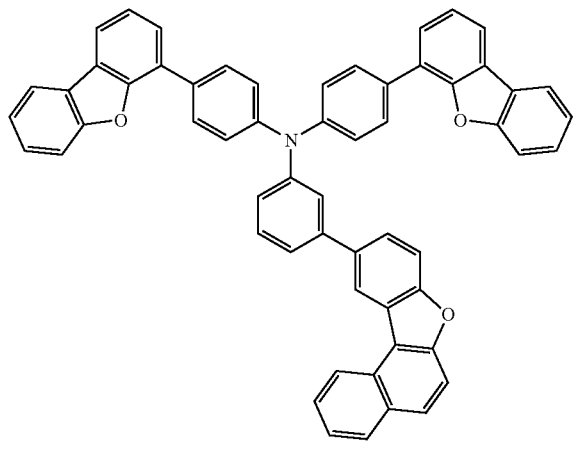
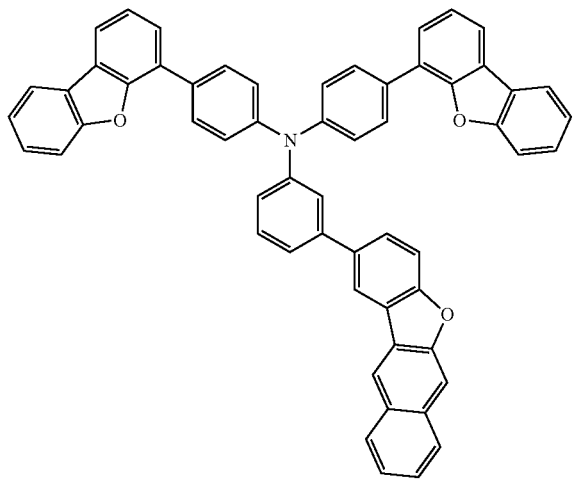

-continued
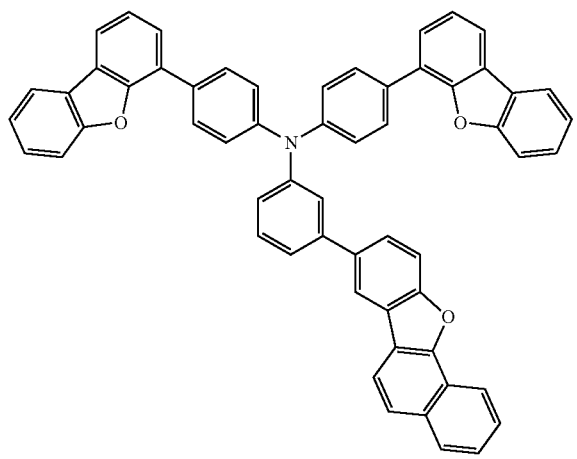
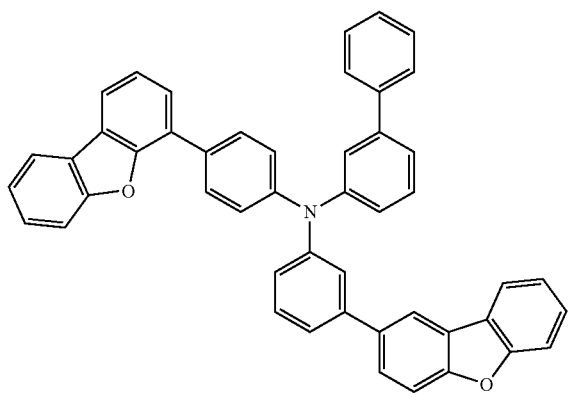
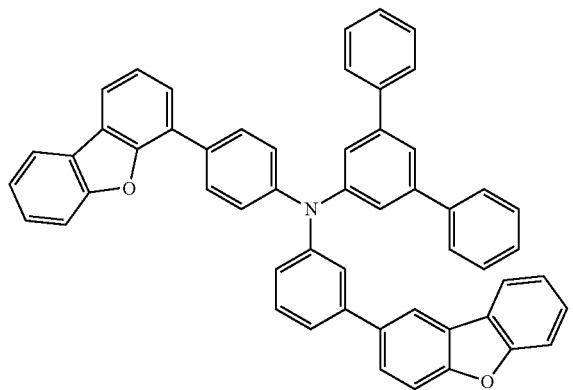
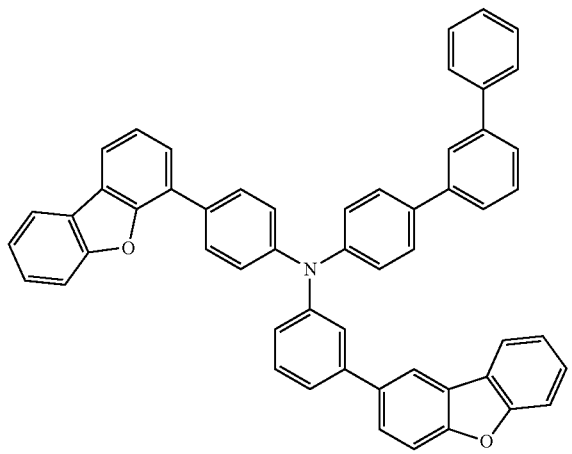
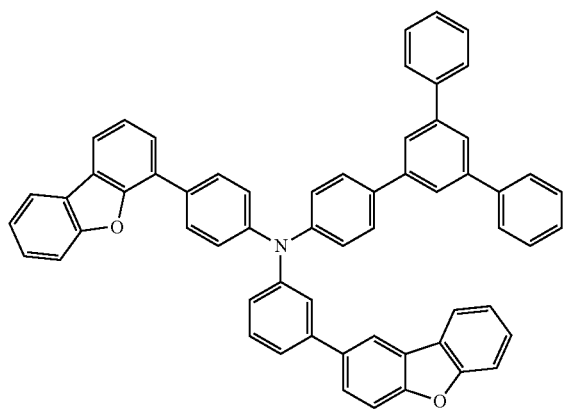
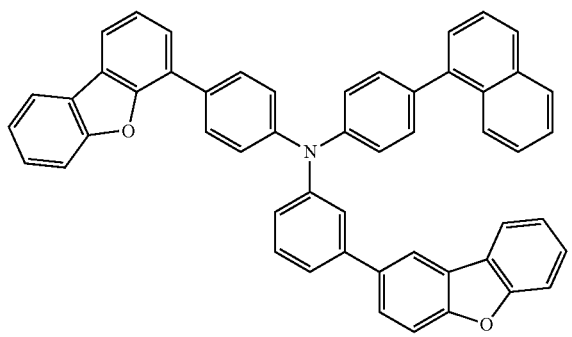

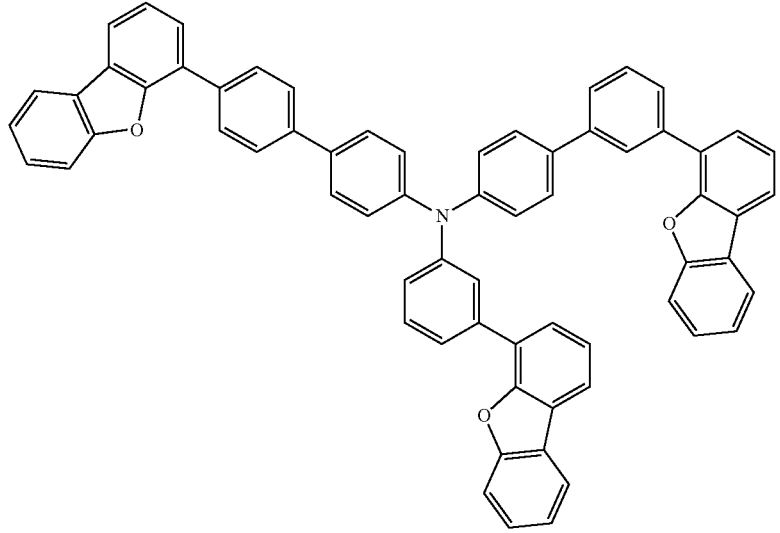

Organic EL Device

The organic EL device of the invention will be described below.

The organic EL device of the invention comprises a cathode, an anode, and an organic thin film layer comprising one or more layers between the cathode and the anode. The organic thin film layer comprises a light emitting layer and at least one layer of the organic thin film layer comprises the aromatic amine derivative of the invention. By using the aromatic amine derivative in at least one layer of the organic thin film layer, it can be expected that the emission efficiency is increased and the lifetime is prolonged.

Examples of the organic thin film layer in which the aromatic amine derivative is comprised include a hole transporting layer, a light emitting layer, a space layer, and a blocking layer, although not limited thereto. The aromatic amine derivative is comprised preferably in a hole transporting layer. The light emitting layer preferably comprises a fluorescent emitting material or a phosphorescent emitting material.

The organic EL device may be any of a single color emitting device of fluorescent or phosphorescent type, a white-emitting device of fluorescent-phosphorescent hybrid type, an emitting device of a simple type having a single emission unit, and an emitting device of a tandem type having two or more emission units. The "emission unit" referred to herein is the smallest unit for emitting light by the recombination of injected holes and injected electrons, which comprises one or more organic layers wherein at least one layer is a light emitting layer.

Representative device structures of the simple-type organic EL device are shown below.
(1) Anode/Emission Unit/Cathode The emission unit may be a laminate comprising two or more layers selected from a phosphorescent light emitting layer and a fluorescent light emitting layer. A space layer may be disposed between the light emitting layers to prevent the diffusion of excitons generated in the phosphorescent light emitting layer into the fluorescent light emitting layer. Representative layered structures of the emission unit are shown below.
(a) hole transporting layer/light emitting layer (/electron transporting layer);
(b) hole transporting layer/first phosphorescent emitting layer/second phosphorescent emitting layer (/electron transporting layer);
(c) hole transporting layer/phosphorescent emitting layer/space layer/fluorescent emitting layer (/electron transporting layer);
(d) hole transporting layer/first phosphorescent emitting layer/second phosphorescent emitting layer/space layer/fluorescent emitting layer (/electron transporting layer);
(e) hole transporting layer/first phosphorescent emitting layer/space layer/second phosphorescent emitting layer/space layer/fluorescent emitting layer (/electron transporting layer); and
(f) hole transporting layer/phosphorescent emitting layer/space layer/first fluorescent emitting layer/second fluorescent emitting layer (/electron transporting layer).

The emission colors of the phosphorescent light emitting layer and that of the fluorescent light emitting layer may be different. For example, the layered structure of the laminated light emitting layer (d) may be hole transporting layer/first phosphorescent light emitting layer (red emission)/second phosphorescent light emitting layer (green emission)/space layer/fluorescent light emitting layer (blue emission)/electron transporting layer.

An electron blocking layer may be disposed between the light emitting layer and the hole transporting layer or between the light emitting layer and the space layer, if necessary. Also, a hole blocking layer may be disposed between the light emitting layer and the electron transporting layer, if necessary. With such an electron blocking layer or a hole blocking layer, electrons and holes are confined in the light emitting layer to increase the degree of charge recombination in the light emitting layer, thereby improving the emission efficiency.

Representative device structure of the tandem-type organic EL device is shown below.
(2) Anode/First Emission Unit/Intermediate Layer/Second Emission Unit/Cathode The layered structure of the first emission unit and the second emission unit may be selected from those described above with respect to the emission unit.

Generally, the intermediate layer is also called an intermediate electrode, an intermediate conductive layer, a charge generation layer, an electron withdrawing layer, a connecting layer, or an intermediate insulating layer. The intermediate layer may be formed by known materials so as to supply electrons to the first emission unit and holes to the second emission unit.

A schematic structure of an example of the organic EL device is shown in FIG. 1 wherein the organic EL device 1 is constructed by a substrate 2, an anode 3, a cathode 4, and an emission unit 10 disposed between the anode 3 and the cathode 4. The emission unit 10 comprises a light emitting layer 5 which comprises at least one phosphorescent emitting layer containing a phosphorescent host material and a phosphorescent dopant. A hole transporting layer 6, etc. may be disposed between the light emitting layer 5 and the anode 3. An electron transporting layer 7, etc. may be disposed between the light emitting layer 5 and the cathode 4. An electron blocking layer may be disposed on the anode 3 side of the light emitting layer 5, and a hole blocking layer may be disposed on the cathode 4 side of the light emitting layer 5. With these blocking layers, electrons and holes are confined in the light emitting layer 5 to increase the degree of exciton generation in the light emitting layer 5.

In the present specification, the host is referred to as a fluorescent host when combinedly used with a fluorescent dopant and referred to as a phosphorescent host when combinedly used with a phosphorescent dopant. Therefore, the fluorescent host and the phosphorescent host are not distinguished from each other merely by the difference in their molecular structures. Namely, the phosphorescent host means a material for constituting a phosphorescent emitting layer containing a phosphorescent dopant and does not mean that the material is not usable as a material for constituting a fluorescent emitting layer. The same also applies to the fluorescent host.

Substrate

The organic EL device is formed preferably on a light-transmissive substrate. The light-transmissive substrate serves as a support for the organic EL device and preferably a flat substrate having a transmittance of 50% or more to 400 to 700 nm visible light. Examples of the substrate include a glass plate and a polymer plate. The glass plate may include a plate made of soda-lime glass, barium-strontium-containing glass, lead glass, aluminosilicate glass, borosilicate glass, barium borosilicate glass, or quartz. The polymer plate may include a plate made of polycarbonate, acryl, polyethylene terephthalate, polyether sulfide, or polysulfone.

Anode

The anode of the organic EL device injects holes to the hole transporting layer or the light emitting layer, and an anode having a work function of 4.5 eV or more is effective. Examples of material for anode include indium tin oxide alloy (ITO), tin oxide (NESA), indium zinc oxide alloy, gold, silver, platinum, and copper. The anode is formed by making the electrode material into a thin film by a method, such as a vapor deposition method and a sputtering method. When getting the light emitted from the light emitting layer through the anode, the transmittance of anode to visible light is preferably 10% or more. The sheet resistance of anode is preferably several hundreds $\Omega/\square$ or less. The film thickness of anode depends upon the kind of material and generally 10 nm to 1 µm, preferably 10 to 200 nm.

Cathode

The cathode injects electrons to the electron injecting layer, the electron transporting layer or the light emitting layer, and preferably formed from a material having a small work function. Examples of the material for cathode include, but not limited to, indium, aluminum, magnesium, magnesium-indium alloy, magnesium-aluminum alloy, aluminum-lithium alloy, aluminum-scandium-lithium alloy, and magnesium-silver alloy. Like the anode, the cathode is formed by making the material into a thin film by a method, such as the vapor deposition method and the sputtering method. The emitted light may be taken from the cathode, if appropriate.

Light Emitting Layer

The light emitting layer is an organic layer having a light emitting function and comprises a host material and a dopant material when a doping system is employed. The major function of the host material is to promote the recombination of electrons and holes and confine excitons in the light emitting layer. The dopant material causes the excitons generated by recombination to emit light efficiently.

In case of a phosphorescent device, the major function of the host material is to confine the excitons generated on the dopant in the light emitting layer.

To control the carrier balance in the light emitting layer, a double host (host and co-host) system may be used for the light emitting layer, for example, by combinedly using an electron transporting host and a hole transporting host.

The light emitting layer may be made into a double dopant layer, in which two or more kinds of dopant materials having high quantum yield are combinedly used and each dopant material emits light with its own color. For example, to obtain a yellow emission, a light emitting layer formed by co-depositing a host, a red-emitting dopant and a green-emitting dopant is used.

Electrons and holes can be accumulated in the interface between the light emitting layers by laminating two or more light emitting layers, thereby localizing the recombination region in the interface between the light emitting layers to improve the quantum efficiency.

The light emitting layer may be different in the hole injection ability and the electron injection ability, and also in the hole transporting ability and the electron transporting ability each being expressed by mobility.

The light emitting layer is formed, for example, by a known method, such as a vapor deposition method, a spin coating method, and LB method. Alternatively, the light emitting layer may be formed by making a solution of a binder, such as resin, and the material for the light emitting layer in a solvent into a thin film by a method such as spin coating.

The light emitting layer is preferably a molecular deposit film. The molecular deposit film is a thin film formed by depositing a vaporized material or a film formed by solidifying a material in the state of solution or liquid. The molecular deposit film can be distinguished from a thin film formed by LB method (molecular build-up film) by the differences in the assembly structures and higher order structures and the functional difference due to the structural differences.

Phosphorescent Emitting Layer

The phosphorescent dopant (phosphorescent emitting material) used in the light emitting layer is a compound which emits light by releasing the energy of excited triplet state and preferably a organometallic complex comprising at least one metal selected from Ir, Pt, Os, Au, Cu, Re, and Ru and a ligand, although not particularly limited thereto as long as emitting light by releasing the energy of excited triplet state. The ligand is preferably ortho-metallated. In view of obtaining a high phosphorescent quantum yield and further improving the external quantum efficiency of emission device, a metal complex comprising a metal selected from Ir, Os, and Pt is preferred, with a metal complex, such as an iridium complex, an osmium complex, and a platinum complex being more preferred, an iridium complex and a platinum complex being still more preferred, and an ortho-metallated iridium complex being particularly preferred.

The content of the phosphorescent dopant in the light emitting layer is not particularly limited and selected according to the use of the device, and preferably 0.1 to 70% by mass, and more preferably 1 to 30% by mass. If being 0.1% by mass or more, the amount of light emission is sufficient. If being 70% by mass or less, the concentration quenching can be avoided.

Preferred examples of the organometallic complex are shown below.

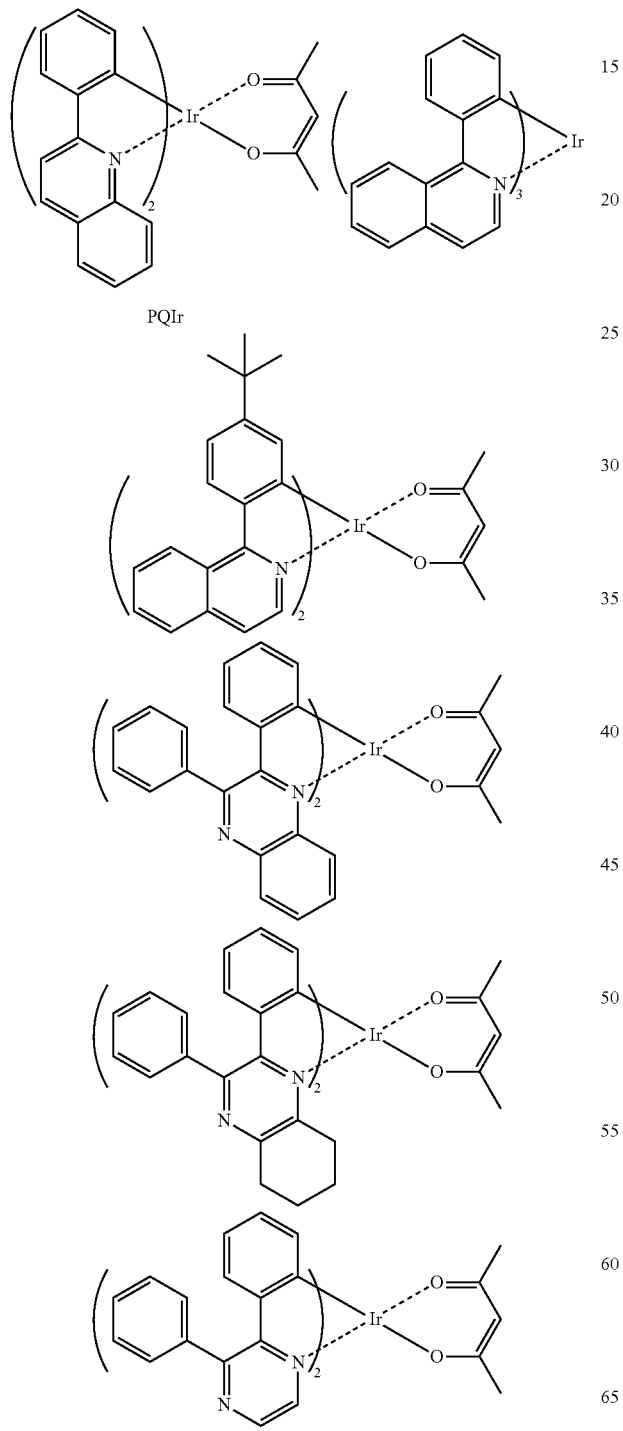

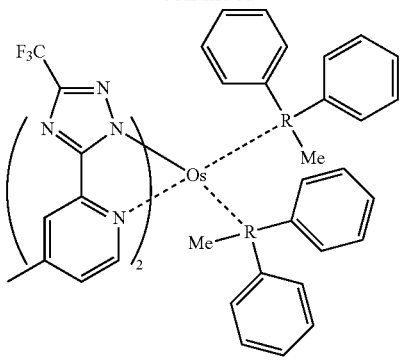

-continued

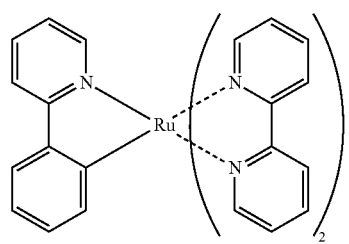

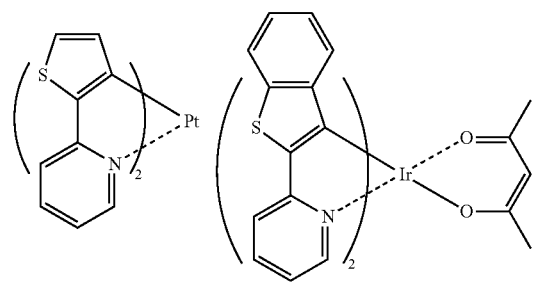

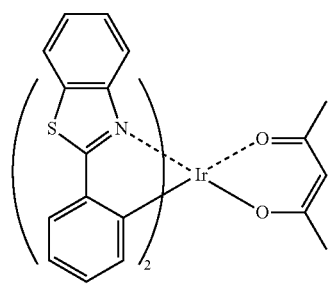

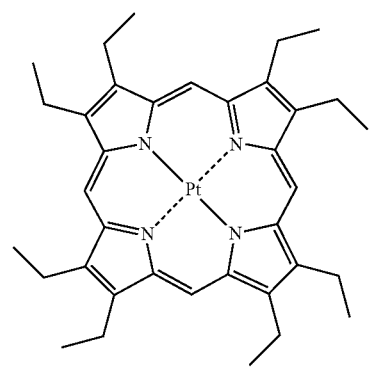

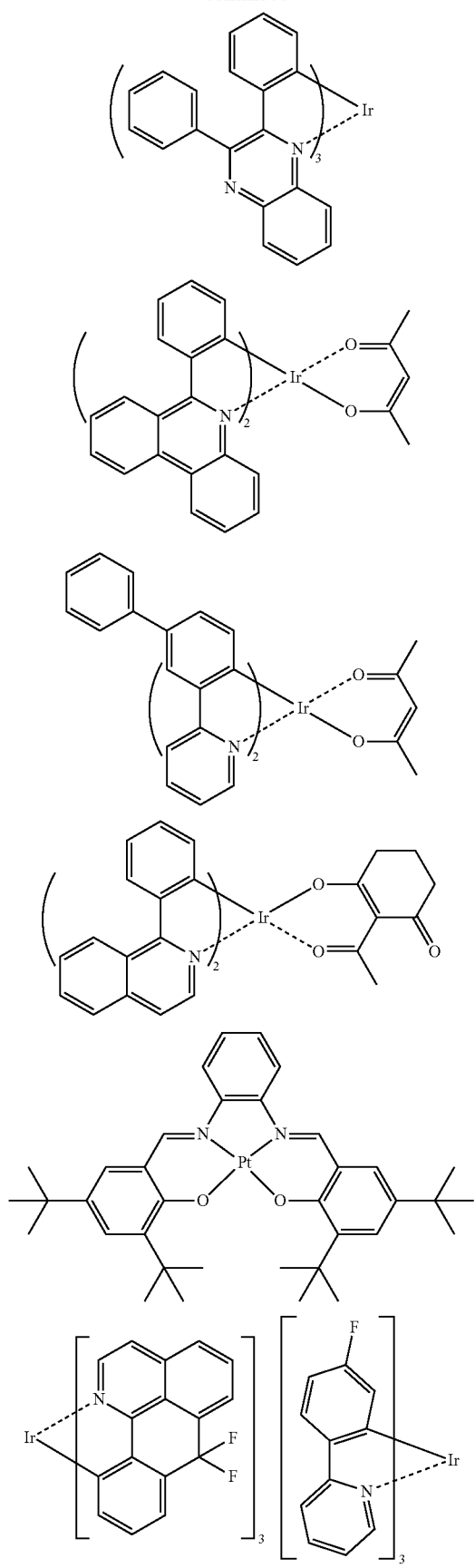
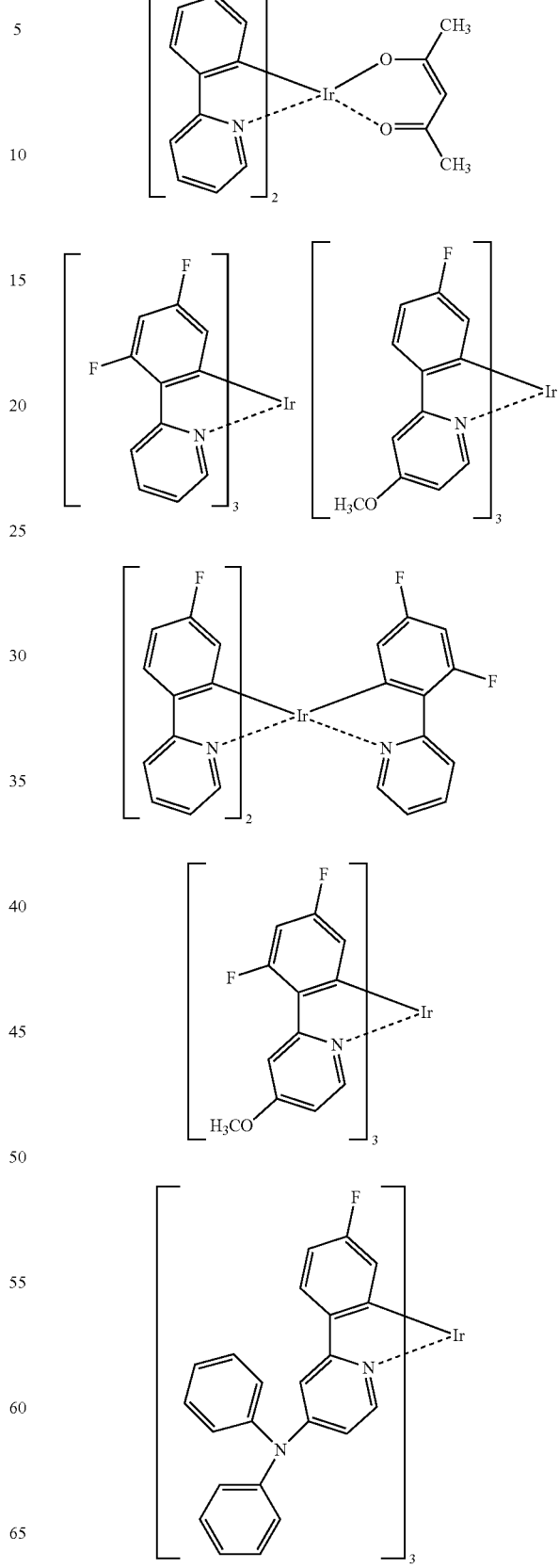

79
-continued
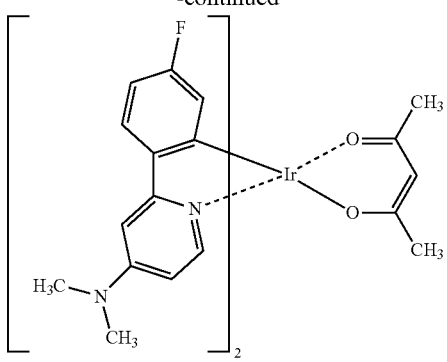
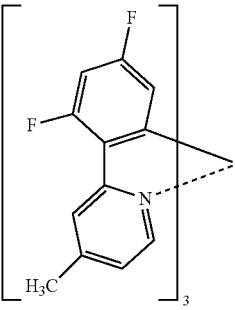
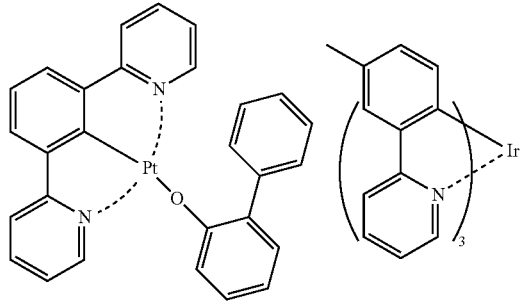
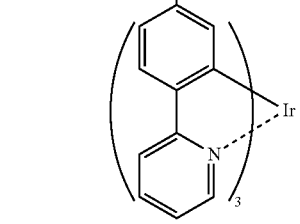
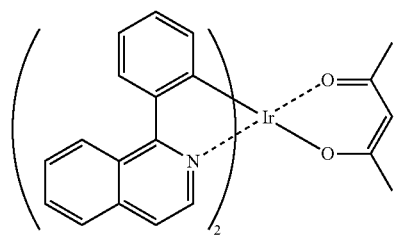
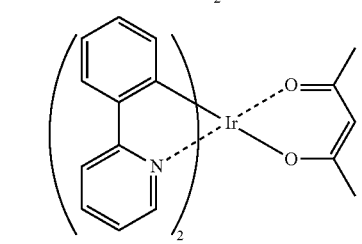
80
-continued
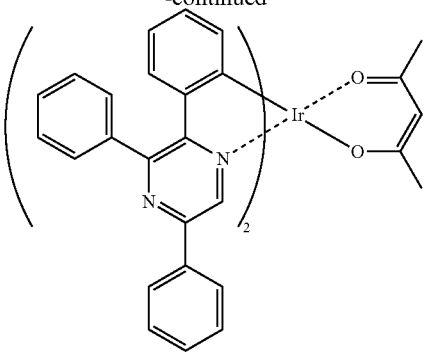
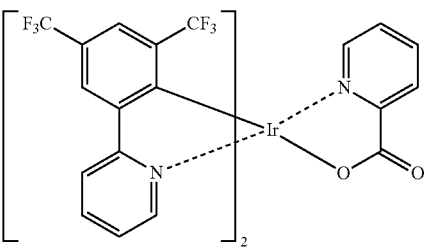
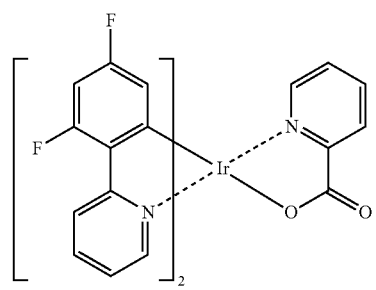
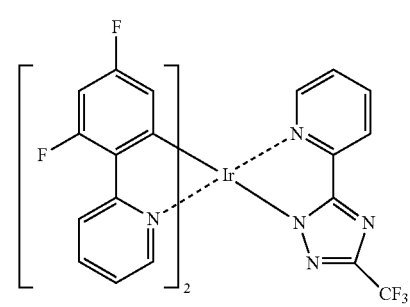
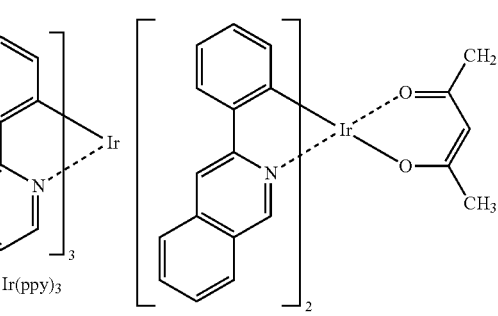
Ir(ppy)₃

81
-continued
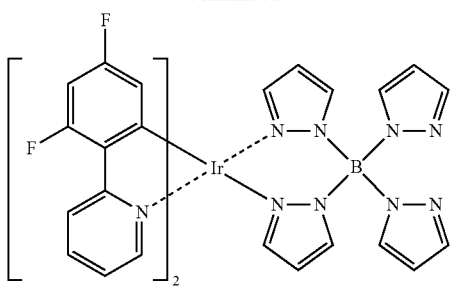
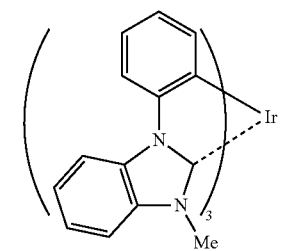
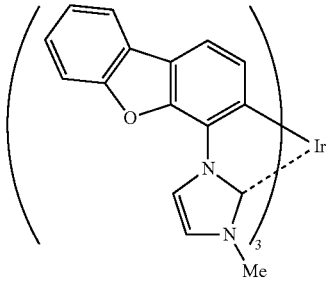
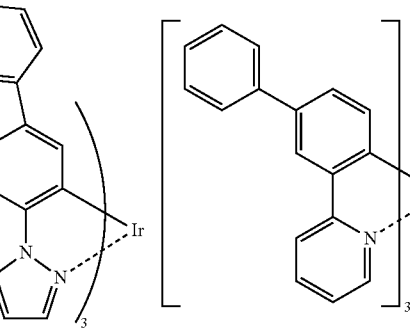
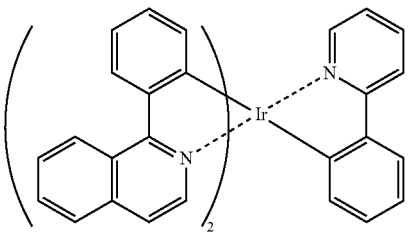
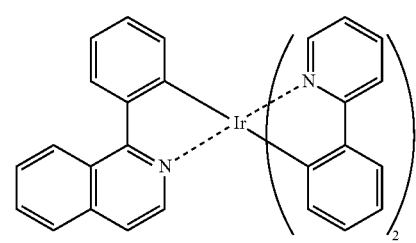
82
-continued
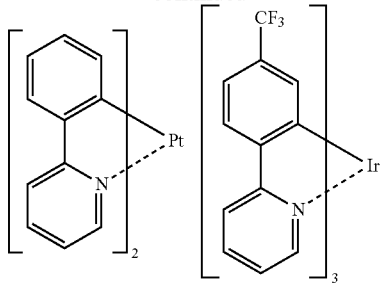
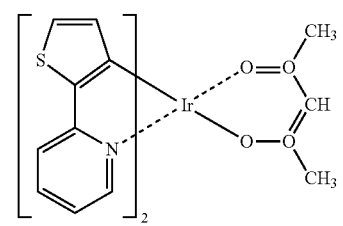
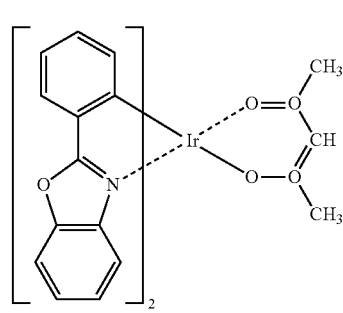
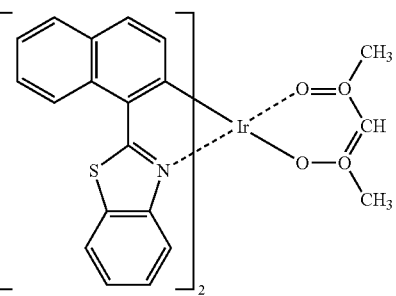
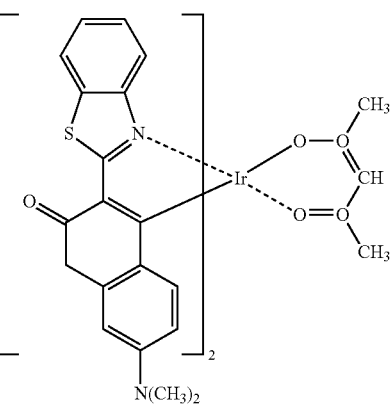

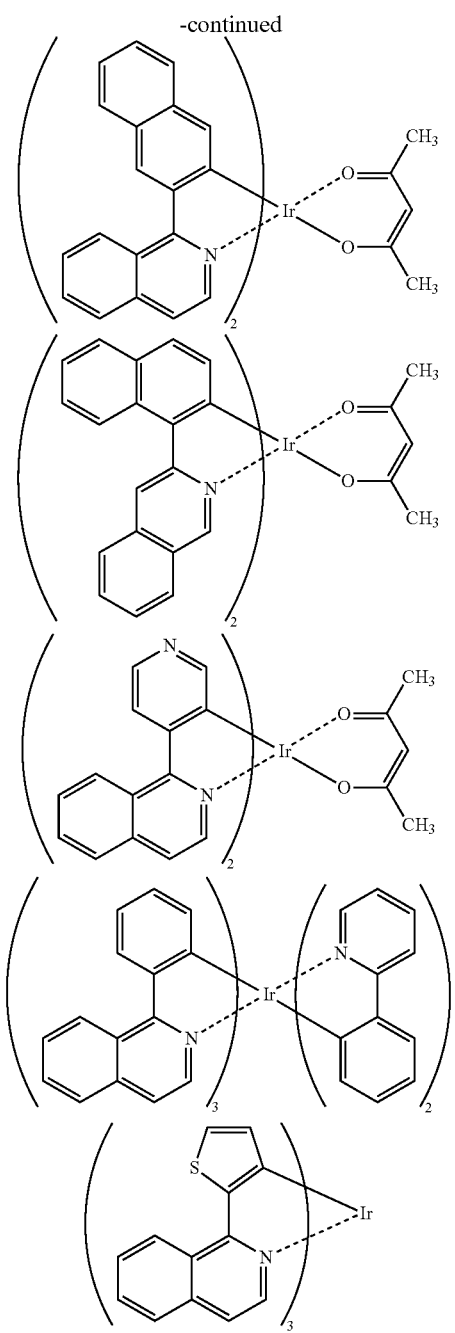

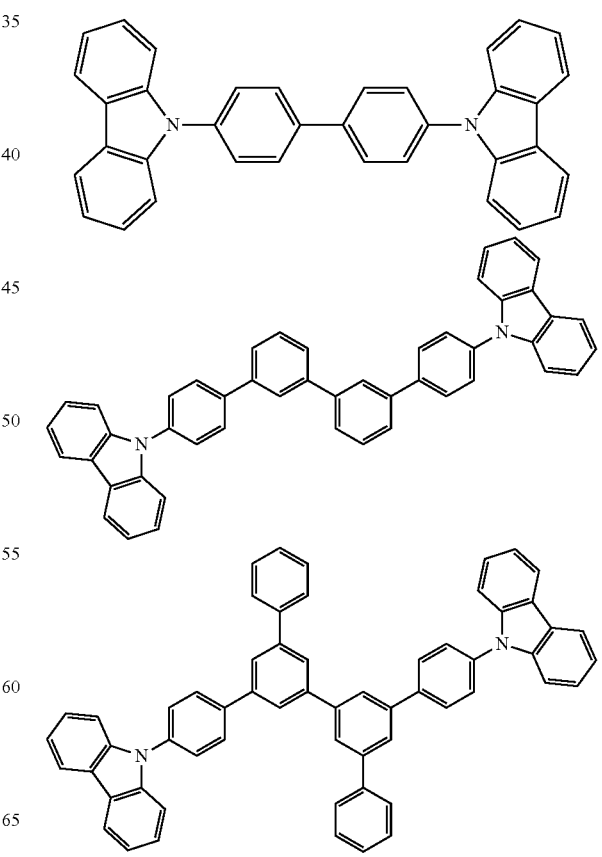

The phosphorescent host is a compound which confines the triplet energy of the phosphorescent dopant efficiently in the light emitting layer to cause the phosphorescent dopant to emit light efficiently. The aromatic amine derivative of the invention is useful as the phosphorescent dopant. In addition to the aromatic amine derivative of the invention, another compound may be used as the phosphorescent host according to the use of the device.

The aromatic amine derivative of the invention and another compound may be combinedly used in the same light emitting layer as the phosphorescent host material. If two or more light emitting layers are formed, the aromatic amine derivative of the invention can be used in one of the light emitting layers as the phosphorescent host material and a compound other than the aromatic amine derivative of the invention can be used in another light emitting layer as the phosphorescent host material. The aromatic amine derivative of the invention may be used in an organic layer other than the light emitting layer. In this case, a compound other than the aromatic amine derivative of the invention may be used as a phosphorescent host of the light emitting layer.

Examples of the preferred phosphorescent host other than the aromatic amine derivatives of the invention include a carbazole derivative, a triazole derivative, a oxazole derivative, an oxadiazole derivative, an imidazole derivative, a polyarylalkane derivative, a pyrazoline derivative, a pyrazolone derivative, a phenylenediamine derivative, an arylamine derivative, an amino-substituted chalcone derivative, a styrylanthracene derivative, a fluorenone derivative, a hydrazone derivative, a stilbene derivative, a silazane derivative, an aromatic tertiary amine compound, a styrylamine compound, an aromatic dimethylidene compound, a porphyrin compound, an anthraquinodimethane derivative, an anthrone derivative, a diphenylquinone derivative, a thiopyran dioxide derivative, a carbodiimide derivative, a fluorenylidenemethane derivative, a distyrylpyrazine derivative, a heterocyclic tetracarboxylic anhydride such as naphthalene and perylene, a phthalocyanine derivative, a metal complex of 8-quinolinol derivative, metal phthalocyanine, metal complexes having a ligand such as benzoxazole and benzothiazole, an electroconductive oligomer, such as a polysilane compound, a poly(N-vinylcarbazole) derivative, an aniline copolymer, a thiophene oligomer, and a polythiophene, and a polymer such as a polythiophene derivative, a polyphenylene derivative, a polyphenylenevinylene derivative, and a polyfluorene derivative. These phosphorescent hosts may be used alone or in combination of two or more. Examples thereof are shown below.

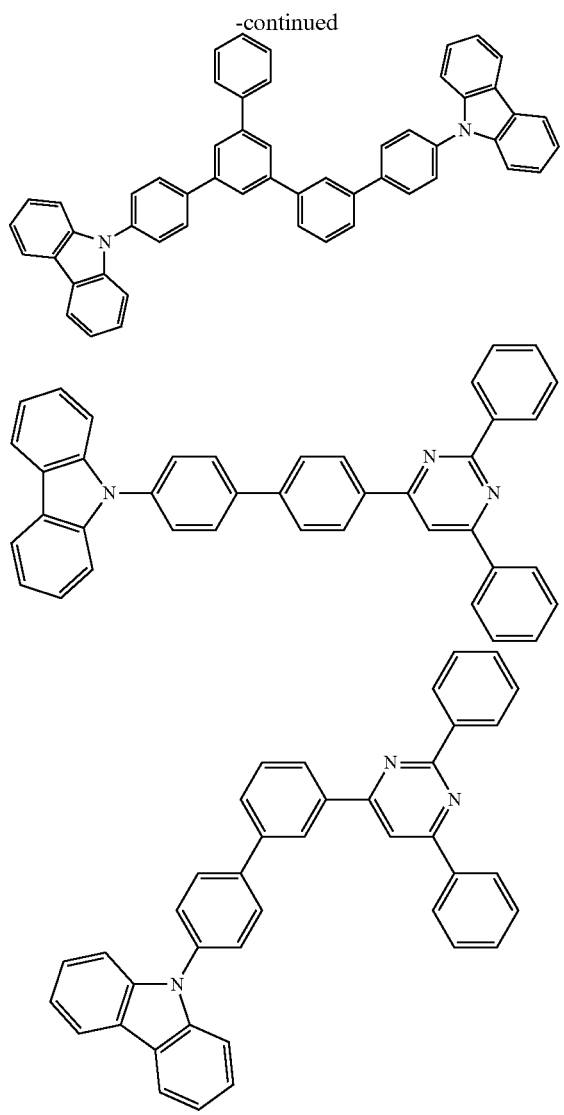

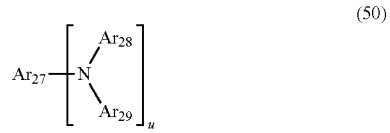

wherein each of $Ar_{27}$ to $Ar_{29}$ represents a substituted or unsubstituted aromatic group having 6 to 40 ring carbon atoms. The subscript u represents an integer of 1 to 4, preferably 1 to 2. At least one of $Ar_{27}$ to $Ar_{29}$ may represent a group containing styryl group. When one of $Ar_{27}$ and $Ar_{28}$ includes a styryl group, at least one of $Ar_{28}$ and $Ar_{29}$ is preferably substituted by a styryl group.

Examples of the aromatic group having 6 to 40 ring carbon atoms include phenyl group, naphthyl group, anthranyl group, phenanthryl group, pyrenyl group, coronyl group, biphenyl group, terphenyl group, pyrrolyl group, furanyl group, thiophenyl group, benzothiophenyl group, oxadiazolyl group, diphenylanthranyl group, indolyl group, carbazolyl group, pyridyl group, benzoquinolyl group, fluoranthenyl group, acenaphthofluoranthenyl group, stilbene group, perylenyl group, chrysenyl group, picenyl group, triphenylenyl group, rubicenyl group, benzoanthracenyl group, phenylanthracenyl group, bisanthracenyl group, and arylene groups represented by formulae (C) and (D). Preferred are naphthyl group, anthranyl group, chrysenyl group, pyrenyl group, and arylene groups represented by formula (D).

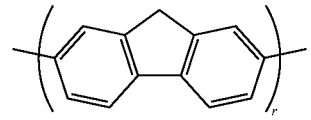

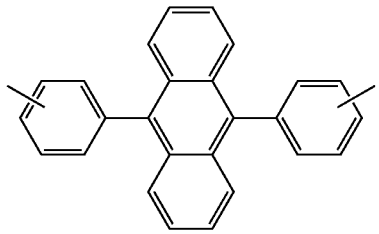

In formula (C), r represents an integer of 1 to 3.

The substituent for the aryl group and the arylene group is preferably an alkyl group having 1 to 6 carbon atoms (ethyl group, methyl group, isopropyl group, n-propyl group, s-butyl group, t-butyl group, pentyl group, hexyl group, cyclopentyl group, and cyclohexyl group, etc.), an alkoxy group having 1 to 6 carbon atoms (ethoxy group, methoxy group, isopropoxy group, n-propoxy group, s-butoxy group, t-butoxy group, pentoxy group, hexyloxy group, cyclopentoxy group, and cyclohexyloxy group, etc.), an aryl group having 5 to 40 carbon atoms, an amino group substituted by an aryl groups having 5 to 40 carbon atoms, an ester group containing an aryl group having 5 to 40 carbon atoms, an ester group containing an alkyl group having 1 to 6 carbon atoms, a cyano group, nitro group, and halogen atoms.

The light emitting material used in the light emitting layer is not particularly limited, and examples of the host material include polycyclic aromatic compounds such as an The thickness of the light emitting layer is preferably 5 to 50 nm, more preferably 7 to 50 nm, and still more preferably 10 to 50 nm. If being 5 nm or more, the light emitting layer is easily formed. If being 50 nm or less, the increase in driving voltage is avoided.

Fluorescent Emitting Layer

The fluorescent dopant is preferably a compound selected from, for example, an amine compound, an aromatic compound, a chelate complex such as a tris(8-quinolinolato)aluminum complex, a coumarin derivative, a tetraphenylbutadiene derivative, a bisstyrylarylene derivative, and an oxadiazole derivative in accordance with an intended luminescent color. An arylamine compound and an aryldiamine compound are particularly preferable. A styrylamine compound, a styryldiamine compound, an aromatic amine compound, and an aromatic diamine compound are more preferable, and a fused polycyclic amine derivative is still more preferable. These fluorescent dopants may be used alone or in combination of two or more.

The organic EL device of the present invention preferably comprises at least one of a styrylamine and an arylamine as the fluorescent dopant. A compound represented by the following formula (50) is preferably used as the styrylamine and the arylamine.

anthracene compound, a phenanthrene compound, a fluoranthene compound, a tetracene compound, a triphenylene compound, a chrysene compound, a pyrene compound, a coronene compound, a perylene compound, a phthaloperylene compound, a naphthaloperylene compound, a naphthacene compound, and a pentacene compound, oxadiazole, bisbenzoxazoline, bisstyryl, cyclopentadiene, a quinoline metal complex, a tris(8-hydroxyquinolinato)aluminum complex, a tris(4-methyl-8-quinolinato)aluminum complex, a tris(5-phenyl-8-quinolinato)aluminum complex, an aminoquinoline metal complex, a benzoquinoline metal complex, tri-(p-terphenyl-4-yl)amine, a 1-aryl-2,5-di(2-thienyl)pyrrole derivative, pyran, quinacridone, rubrene, a distyrylbenzene derivative, a distyrylarylene derivative, a porphyrin derivative, a stilbene derivative, a pyrazoline derivative, a coumarin dye, a pyran dye, a phthalocyanine dye, a naphthalocyanine dye, a croconium dye, a squalium dye, an oxobenzanthracene dye, a fluorescein dye, a rhodamine dye, a pyrylium dye, a perylene dye, a stilbene dye, a polythiophene dye, a rare-earth complex-based fluorescent substance, a rare-earth-based phosphorescent complex (such as an Ir complex), and conductive polymers such as polyvinylcarbazole, polysilane, and polyethylenedioxidethiophene (PEDOT). Those compounds may be used alone or in combination of two or more.

The compounds represented by formulae (51) to (57) are preferably used as the host material.

Anthracene Derivative Represented by Formula (51):

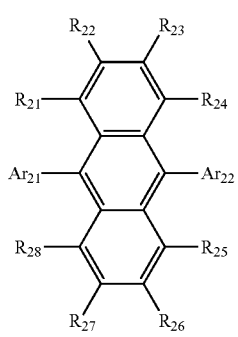

(51)

wherein:

$Ar_{21}$ and $Ar_{22}$ are each independently a substituted or unsubstituted aromatic group having 6 to 60 carbon atoms; and $R_{21}$ to $R_{28}$ are each independently a hydrogen atom, a substituted or unsubstituted aromatic ring group having 6 to 50 carbon atoms, a substituted or unsubstituted aromatic heterocyclic group having 5 to 50 atoms, a substituted or unsubstituted alkyl group having 1 to 50 carbon atoms, a substituted or unsubstituted cycloalkyl group, a substituted or unsubstituted alkoxy group having 1 to 50 carbon atoms, a substituted or unsubstituted aralkyl group having 6 to 50 carbon atoms, a substituted or unsubstituted aryloxy group having 5 to 50 atoms, a substituted or unsubstituted arylthio group having 5 to 50 atoms, a substituted or unsubstituted alkoxycarbonyl group having 1 to 50 carbon atoms, a substituted or unsubstituted silyl group, carboxyl group, halogen atom, a cyano group, nitro group, or hydroxyl group.

Pyrene Derivative Represented by Formula (52):

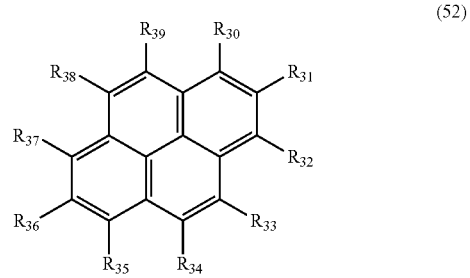

(52)

wherein $R_{30}$ to $R_{39}$ each independently represents a hydrogen atom, a substituted or unsubstituted aromatic group having 6 to 50 carbon atoms, a substituted or unsubstituted aromatic heterocyclic group having 5 to 50 atoms, a substituted or unsubstituted alkyl group having 1 to 50 carbon atoms, a substituted or unsubstituted cycloalkyl group, a substituted or unsubstituted alkoxy group having 1 to 50 carbon atoms, a substituted or unsubstituted aralkyl group having 6 to 50 carbon atoms, a substituted or unsubstituted aryloxy group having 5 to 50 atoms, a substituted or unsubstituted arylthio group having 5 to 50 atoms, a substituted or unsubstituted alkoxycarbonyl group having 1 to 50 carbon atoms, a substituted or unsubstituted silyl group, carboxyl group, halogen atom, a cyano group, nitro group, or hydroxy group.

Anthracene Derivative Represented by Formula (53):

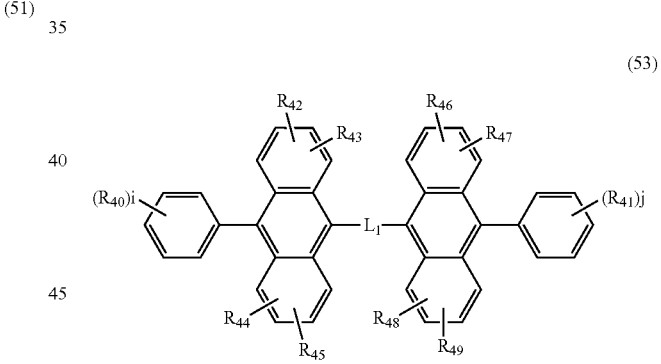

(53)

wherein:

$R_{40}$ to $R_{49}$ each independently represents a hydrogen atom, an alkyl group, a cycloalkyl group, an aryl group which may be substituted, an alkoxyl group, an aryloxy group, an alkylamino group, an alkenyl group, an arylamino group, or a heterocyclic group which may be substituted;

i and j each represents an integer of 1 to 5, and when i or j represents 2 or more, the groups $R_{40}$ or the groups $R_{41}$ are the same or different and the groups $R_{40}$ or the groups $R_{41}$ may be bonded to each other to form a ring, and $R_{42}$ and $R_{43}$, $R_{44}$ and $R_{45}$, $R_{46}$ and $R_{47}$, or $R_{48}$ and $R_{49}$ may be bonded to each other to form a ring; and $L_1$ represents a single bond, —O—, —S—, —N(R)— (wherein R represents an alkyl group or an aryl group which may be substituted), an alkylene group, or an arylene group.

Anthracene Derivative Represented by Formula (54):

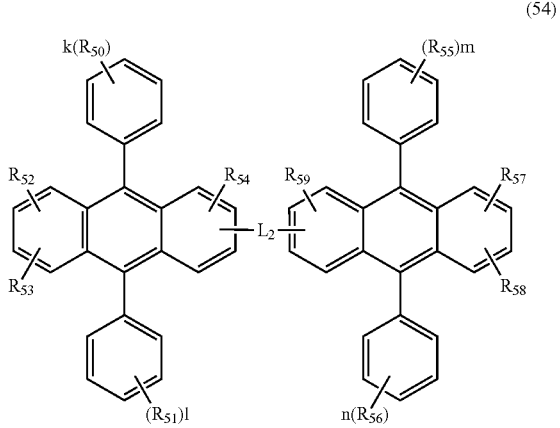

(54)

wherein:

$R_{50}$ to $R_{59}$ each independently represents a hydrogen atom, an alkyl group, a cycloalkyl group, an aryl group, an alkoxyl group, an aryloxy group, an alkylamino group, an arylamino group, or a heterocyclic group which may be substituted;

k, l, m, and n each represents an integer of 1 to 5, and when any one of k, l, m, and n represents 2 or more, each of the groups $R_{50}$, the groups $R_{51}$, the groups $R_{55}$, or the groups $R_{56}$ may be the same or different and each of the groups $R_{52}$, the groups $R_{53}$, the groups $R_{54}$, or the groups $R_{55}$ may be bonded to each other to form a ring, and $R_{52}$ and $R_{53}$ or $R_{57}$ and $R_{58}$ may be bonded to each other to form a ring; and $L_2$ represents a single bond, —O—, —S—, —N(R)— (wherein R represents an alkyl group or an aryl group which may be substituted), an alkylene group, or an arylene group.

Spirofluorene Derivative Represented by Formula (55):

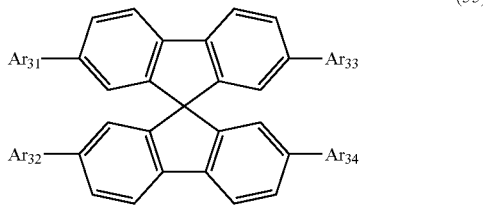

(55)

wherein $Ar_{31}$ to $Ar_{34}$ each independently represents a substituted or unsubstituted biphenylyl group or a substituted or unsubstituted naphthyl group Compound Represented by Formula (56):

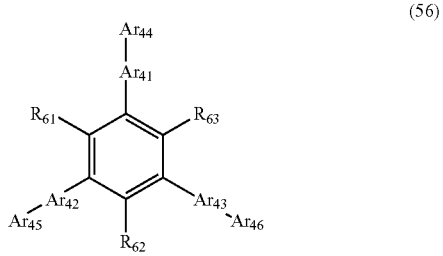

(56)

wherein:

$Ar_{41}$ to $Ar_{43}$ each independently represents a substituted or unsubstituted arylene group having 6 to 60 carbon atoms, and $Ar_{44}$ to $Ar_{46}$ each independently represents a hydrogen atom or a substituted or unsubstituted aryl group having 6 to 60 carbon atoms; and $R_{61}$ to $R_{63}$ each independently represents a hydrogen atom, an alkyl group having 1 to 6 carbon atoms, a cycloalkyl group having 3 to 6 carbon atoms, an alkoxyl group having 1 to 6 carbon atoms, an aryloxy group having 5 to 18 carbon atoms, an aralkyloxy group having 7 to 18 carbon atoms, an arylamino group having 5 to 16 carbon atoms, nitro group, a cyano group, an ester group having 1 to 6 carbon atoms, or halogen atom.

Fluorene Compound Represented by Formula (57):

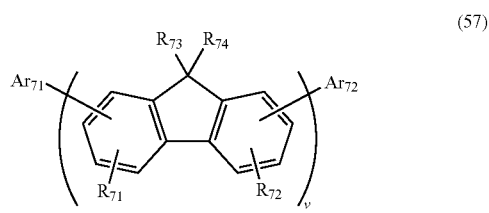

(57)

wherein:

$R_{71}$ and $R_{72}$ each represents a hydrogen atom, a substituted or unsubstituted alkyl group, a substituted or unsubstituted aralkyl group, a substituted or unsubstituted aryl group, a substituted or unsubstituted heterocyclic group, a substituted amino group, a cyano group, or a halogen atom, $R_{71}$ groups or $R_{72}$ groups bonded to different fluorene groups are the same or different, and $R_{71}$ and $R_{72}$ bonded to the same fluorene group are the same or different;

$R_{73}$ and $R_{74}$ each represents a hydrogen atom, a substituted or unsubstituted alkyl group, a substituted or unsubstituted aralkyl group, a substituted or unsubstituted aryl group, or a substituted or unsubstituted heterocyclic group, the groups $R_{73}$ or the groups $R_{74}$ bonded to different fluorene groups are the same or different, and $R_{73}$ and $R_{74}$ bonded to the same fluorene group are the same or different; and $Ar_{71}$ and $Ar_{72}$ are the same or different and each represents a substituted or unsubstituted fused polycyclic aromatic group having three or more benzene rings in total or a substituted or unsubstituted fused polycyclic heterocyclic group bonded to a fluorene group via carbon atom wherein a total of the benzene ring and the heterocyclic ring is 3 or more; and v represents an integer of 1 to 10.

Of the above host materials, preferred is the anthracene derivative, more preferred is the monoanthracene derivative, and particularly preferred is the asymmetric anthracene.

Electron-Donating Dopant

The organic EL device preferably comprises an electron-donating dopant in the interfacial region between the cathode and the light emitting unit. With such a construction, the organic EL device has an improved luminance and an elongated lifetime. The electron-donating dopant is a metal having a work function of 3.8 eV or less or a compound containing such metal. Examples thereof include at least one compound selected from alkali metal, alkali metal complex, alkali metal compound, alkaline earth metal, alkaline earth metal complex, alkaline earth metal compound, rare earth metal, rare earth metal complex, and rare earth metal compound.

Examples of the alkali metal include Na (work function: 2.36 eV), K (work function: 2.28 eV), Rb (work function: 2.16 eV), and Cs (work function: 1.95 eV), with those having a work function of 2.9 eV or less being particularly preferred.

Of the above, preferred are K, Rb, and Cs, more preferred are Rb and Cs, and most preferred is Cs. Examples of the alkaline earth metal include Ca (work function: 2.9 eV), Sr (work function: 2.0 to 2.5 eV), and Ba (work function: 2.52 eV), with those having a work function of 2.9 eV or less being particularly preferred. Examples of the rare earth metal include Sc, Y, Ce, Tb, and Yb, with those having a work function of 2.9 eV or less being particularly preferred.

Examples of the alkali metal compound include alkali oxide, such as $Li_2O$, $Cs_2O$, $K_2O$, and alkali halide, such as LiF, NaF, CsF, and KF, with LiF, $Li_2O$, and NaF being preferred. Examples of the alkaline earth metal compound include BaO, SrO, CaO, and mixture thereof, such as $Ba_xSr_{1-x}O$ (0<x<1) and $Ba_xCa_{1-x}O$ (0<x<1), with BaO, SrO, and CaO being preferred. Examples of the rare earth metal compound include $YbF_3$, $ScF_3$, $ScO_3$, $Y_2O_3$, $Ce_2O_3$, $GdF_3$, and $TbF_3$, with $YbF_3$, $ScF_3$, and $TbF_3$ being preferred.

Examples of the alkali metal complex, alkaline earth metal complex, and rare earth metal complex are not particularly limited as long as containing at least one metal ion selected from alkali metal ions, alkaline earth metal ions, rare earth metal ions, respectively. The ligand is preferably, but not limited to, quinolinol, benzoquinolinol, acridinol, phenanthridinol, hydroxyphenyloxazole, hydroxyphenylthiazole, hydroxydiaryloxadiazole, hydroxydiarylthiadiazole, hydroxyphenylpyridine, hydroxyphenylbenzimidazole, hydroxybenzotriazole, hydroxyfulborane, bipyridyl, phenanthroline, phthalocyanine, porphyrin, cyclopentadiene, β-diketones, azomethines, and derivative thereof.

The electron-donating dopant is added to the interfacial region preferably into a form of layer or island. The electron-donating dopant is added preferably by co-depositing the electron-donating dopant with the organic compound (light emitting material, electron injecting material) for forming the interfacial region by a resistance heating deposition method, thereby dispersing the electron-donating dopant into the organic material. The disperse concentration expressed by the molar ratio of the organic material and the electron-donating dopant is 100:1 to 1:100 and preferably 5:1 to 1:5.

When the electron-donating dopant is formed into a form of layer, a light emitting material or an electron injecting material is made into a layer which serves as an organic layer in the interface, and then, the electron-donating dopant alone is deposited by a resistance heating deposition method into a layer having a thickness preferably 0.1 to 15 nm. When the electron-donating dopant is formed into a form of island, a light emitting material or an electron injecting material is made into a form of island which serves as an organic layer in the interface, and then, the electron-donating dopant alone is deposited by a resistance heating deposition method into a form of island having a thickness preferably 0.05 to 1 nm.

The molar ratio of the main component and the electron-donating dopant in the organic electroluminescence device of the invention is preferably 5:1 to 1:5 and more preferably 2:1 to 1:2.

Electron Transporting Layer

The electron transporting layer is an organic layer disposed between the light emitting layer and the cathode and transports electrons from the cathode to the light emitting layer. If two or more electron transporting layers are provided, the organic layer closer to the cathode may be called an electron injecting layer in some cases. The electron injecting layer injects electrons from the cathode to the organic layer unit efficiently.

An aromatic heterocyclic compound having one or more heteroatoms in a molecule thereof is preferably used as an electron transporting material used in the electron transporting layer, and a nitrogen-containing ring derivative is particularly preferred. In addition, the nitrogen-containing ring derivative is preferably an aromatic ring compound having a nitrogen-containing, 6- or 5-membered ring, or a fused aromatic ring compound having a nitrogen-containing, 6- or 5-membered ring.

The nitrogen-containing ring derivative is preferably, for example, a metal chelate complex of a nitrogen-containing ring represented by formula (A):

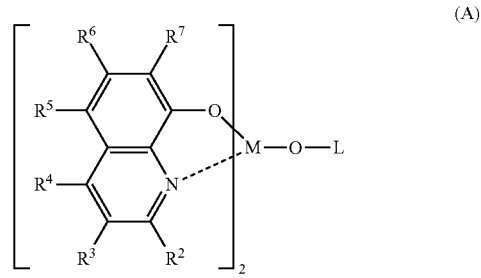

wherein each of $R^2$ to $R^7$ independently represents a hydrogen atom, a halogen atom, a hydroxyl group, an amino group, a hydrocarbon group having 1 to 40 carbon atoms, an alkoxy group having 1 to 40 carbon atoms, an aryloxy group having 6 to 50 carbon atoms, an alkoxycarbonyl group, or an aromatic heterocyclic group having 5 to 50 ring carbon atoms, each being optionally substituted.

The halogen atom may include fluorine, chlorine, bromine, and iodine.

The substituted amino group may include an alkylamino group, an arylamino group, and an aralkylamino group.

The alkylamino group and the aralkylamino group are represented by $-NQ^1Q^2$. Each of $Q^1$ and $Q^2$ independently represents an alkyl group having 1 to 20 carbon atoms or an aralkyl group having 1 to 20 carbon atoms. One of $Q^1$ and $Q^2$ may be a hydrogen atom.

The arylamino group is represented by $-NAr^1Ar^2$, wherein each of $Ar^1$ and $Ar^2$ independently represents a non-fused aromatic hydrocarbon groups or a fused aromatic hydrocarbon groups, each having 6 to 50 carbon atoms. One of $Ar^1$ and $Ar^2$ may be a hydrogen atom.

Examples of the hydrocarbon group having 1 to 40 carbon atoms include an alkyl group, an alkenyl group, a cycloalkyl group, an aryl group, and an aralkyl group.

The alkoxycarbonyl group is represented by $-COOY'$, wherein Y' is an alkyl group having 1 to 20 carbon atoms.

M is aluminum (Al), gallium (Ga), or indium (In), with In being preferred.

L is a group represented by formula (A') or (A"):

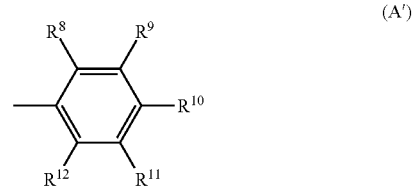

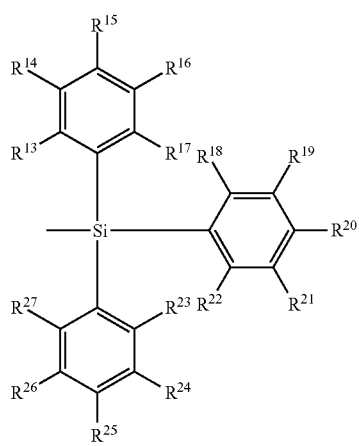

wherein each of $R^8$ to $R^{12}$ in formula (A') independently represents a hydrogen atom or a substituted or unsubstituted hydrocarbon group having 1 to 40 carbon atoms. The adjacent two groups may form a ring structure. Each of $R^{13}$ to $R^{27}$ in formula (A") independently represents a hydrogen atom or a substituted or unsubstituted hydrocarbon group having 1 to 40 carbon atoms. The adjacent two groups may form a ring structure.

Examples of the hydrocarbon group having 1 to 40 carbon atoms for $R^8$ to $R^{12}$ and $R^{13}$ to $R^{27}$ in formulae (A') and (A") are the same as those described above with respect to $R^2$ to $R^7$ of formula (A). Examples of the divalent group formed by the adjacent two groups of $R^8$ to $R^{12}$ and $R^{13}$ to $R^{27}$ which completes the ring structure include tetramethylene group, pentamethylene group, hexamethylene group, diphenylmethane-2,2'-diyl group, diphenylethane-3,3'-diyl group, and diphenylpropane-4,4'-diyl group.

The electron transporting compound for the electron transporting layer is preferably a metal complex including 8-hydroxyquinoline or its derivative, an oxadiazole derivative, and a nitrogen-containing heterocyclic derivative. Examples of the metal complex including 8-hydroxyquinoline or its derivative include a metal chelate oxinoid including a chelated oxine (generally, 8-quinolinol or 8-hydroxyquinoline), for example, tris(8-quinolinol)aluminum. Examples of the oxadiazole derivative are shown below:

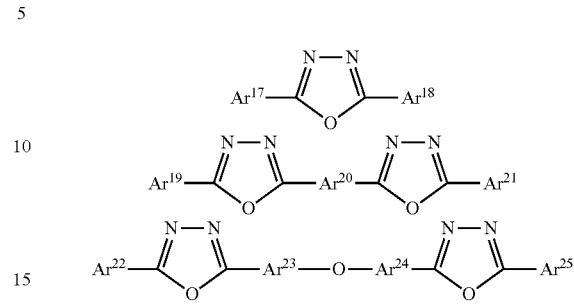

(A")

wherein each of $Ar^{17}$, $Ar^{18}$, $Ar^{19}$, $Ar^{21}$, $Ar^{22}$, and $Ar^{25}$ is a substituted or unsubstituted aromatic hydrocarbon group or a substituted or unsubstituted fused aromatic hydrocarbon group each having 6 to 50 carbon atoms, and $Ar^{17}$ and $Ar^{18}$, $Ar^{19}$ and $Ar^{21}$, and $Ar^{22}$ and $Ar^{25}$ may be the same or different. Examples of the aromatic hydrocarbon group and the fused aromatic hydrocarbon group include phenyl group, naphthyl group, a biphenyl group, anthranyl group, perylenyl group, and pyrenyl group. The optional substituent may be an alkyl group having 1 to 10 carbon atoms, an alkoxyl group having 1 to 10 carbon atoms or a cyano group.

Each of $Ar^{20}$, $Ar^{23}$, and $Ar^{24}$ is a substituted or unsubstituted bivalent aromatic hydrocarbon group or a substituted or unsubstituted bivalent fused aromatic hydrocarbon group each having 6 to 50 carbon atoms, and $Ar^{23}$ and $Ar^{24}$ may be the same or different. Examples of the bivalent aromatic hydrocarbon group or the bivalent fused aromatic hydrocarbon group include phenylene group, naphthylene group, biphenylene group, anthranylene group, perylenylene group, and pyrenylene group. The optional substituent may be an alkyl group having 1 to 10 carbon atoms, an alkoxyl group having 1 to 10 carbon atoms or a cyano group.

Electron transporting compounds which have a good thin film-forming property are preferably used. Examples of the electron transporting compound are shown below.

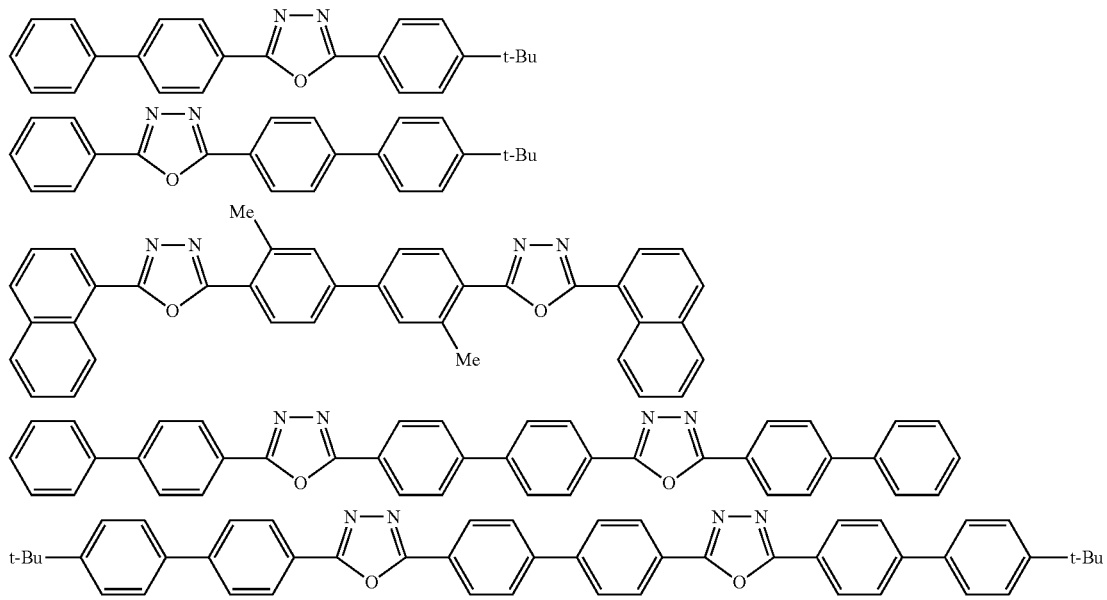

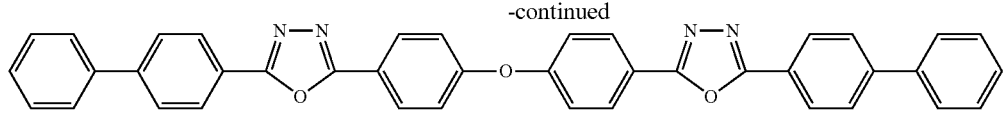

Examples of the nitrogen-containing heterocyclic derivative for use as the electron transporting compound include a nitrogen-containing heterocyclic derivative having the following formulae but exclusive of metal complex, for example, a compound having a 5- or 6-membered ring which has the skeleton represented by formula (B) or having the structure represented by formula (C):

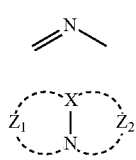 (B)

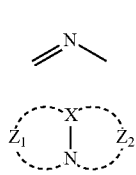 (C)

wherein X is a carbon atom or a nitrogen atom and each of $Z_1$ and $Z_2$ independently represents a group of atoms for completing the nitrogen-containing heteroring.

The nitrogen-containing heterocyclic derivative is more preferably an organic compound which has a nitrogen-containing aromatic polycyclic ring comprising a 5-membered ring or a 6-membered ring. If two or more nitrogen atoms are included, the nitrogen-containing aromatic polycyclic compound preferably has a skeleton of a combination of (B) and (C) or a combination of (B) and (D):

 (D)

The nitrogen-containing group of the nitrogen-containing aromatic polycyclic compound is selected, for example, from the nitrogen-containing heterocyclic groups shown below:

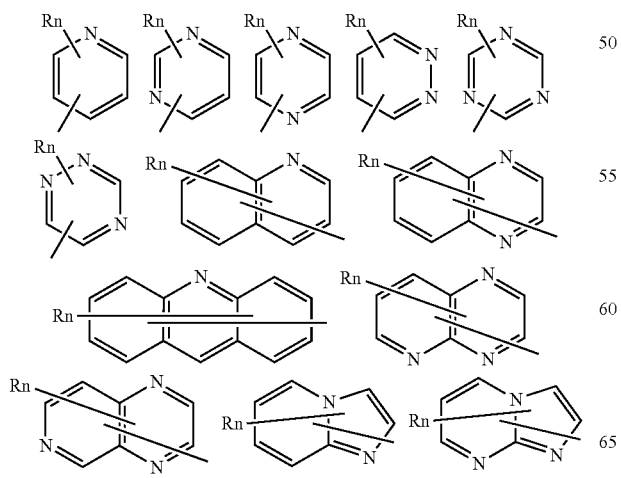

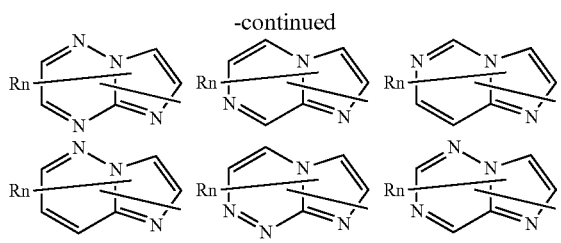

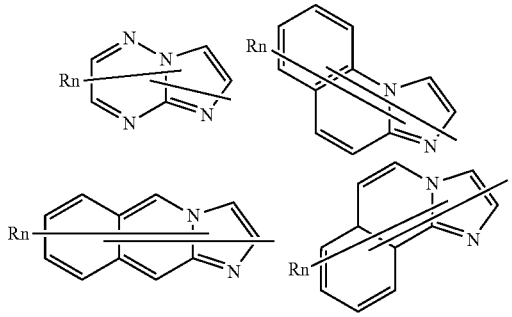

wherein R is an aromatic hydrocarbon group or a fused aromatic hydrocarbon group each having 6 to 40 carbon atoms, an aromatic heterocyclic group or a fused aromatic heterocyclic group each having 3 to 40 carbon atoms, an alkyl group having 1 to 20 carbon atoms, or an alkoxy group having 1 to 20 carbon atoms; and n is an integer of 0 to 5. If n is an integer of 2 or more, the groups R may be the same or different.

More preferred is a nitrogen-containing heterocyclic derivative represented by formula:

$$HAr-L^1-Ar^1-Ar^2$$

wherein HAr is a substitute or unsubstituted nitrogen-containing heterocyclic group having 3 to 40 carbon atoms; $L^1$ is a single bond, a substituted or unsubstituted aromatic hydrocarbon group or fused aromatic hydrocarbon group each having 6 to 40 carbon atoms, or a substituted or unsubstituted aromatic heterocyclic group or fused aromatic heterocyclic group each having 3 to 40 carbon atoms; $Ar^1$ is a substitute or unsubstituted divalent aromatic hydrocarbon group having 6 to 40 carbon atoms; and $Ar^2$ is a substitute or unsubstituted aromatic hydrocarbon group or fused aromatic hydrocarbon group each having 6 to 40 carbon atoms or a substituted or unsubstituted aromatic heterocyclic group or fused aromatic heterocyclic group each having 3 to 40 carbon atoms.

HAr is selected, for example, from the following groups:

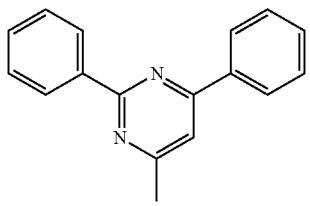

-continued
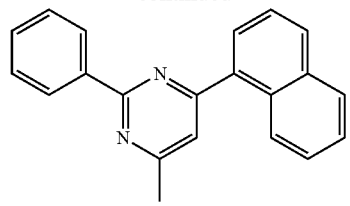
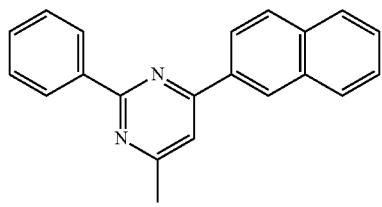
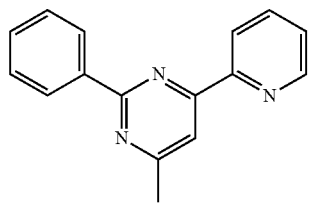
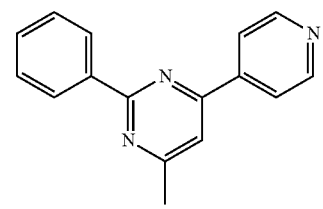
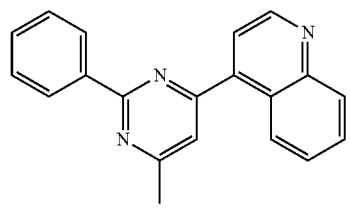
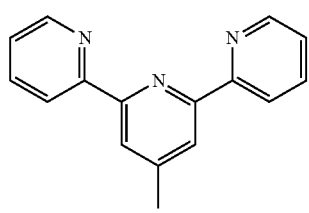 [SMILES: Cc1cc(-c2ccccc2)nc(-c2ccccn2)c1]
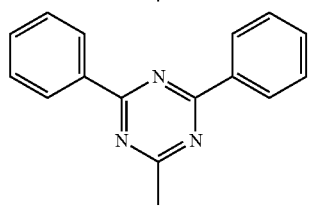
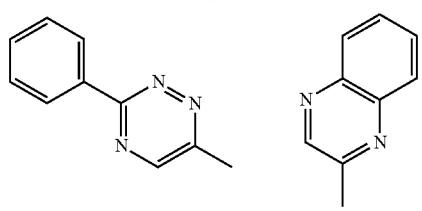
$L^1$ is selected, for example, from the following groups:
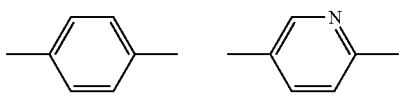

Ar$^1$ is selected, for example, from the following arylanthranyl group:

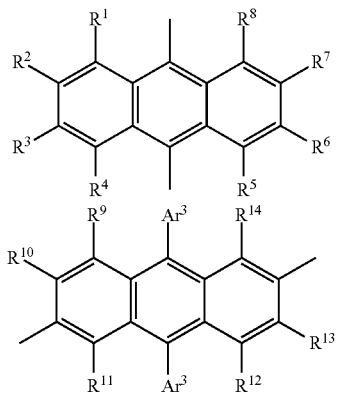

wherein R$^1$ to R$^{14}$ are each independently a hydrogen atom, a halogen atom, an alkyl group having 1 to 20 carbon atoms, an alkoxy group having 1 to 20 carbon atoms, an aryloxy group having 6 to 40 carbon atoms, a substituted or unsubstituted aromatic hydrocarbon group or fused aromatic hydrocarbon group each having 6 to 40 carbon atoms, or a substituted or unsubstituted aromatic heterocyclic group or fused aromatic heterocyclic group each having 3 to 40 carbon atoms; and Ar$^3$ is a substituted or unsubstituted aromatic hydrocarbon group or fused aromatic hydrocarbon group each having 6 to 40 carbon atoms or a substituted or unsubstituted aromatic heterocyclic group or fused aromatic heterocyclic group each having 3 to 40 carbon atoms. R$^1$ to R$^8$ may be all hydrogen atoms.

Ar$^2$ is selected, for example, from the following groups:

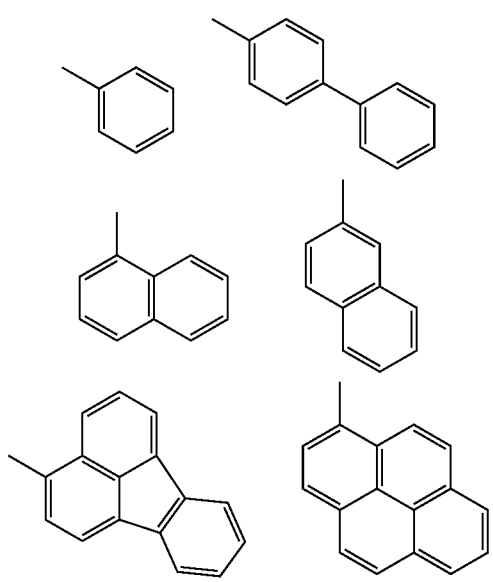

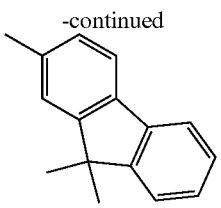

-continued

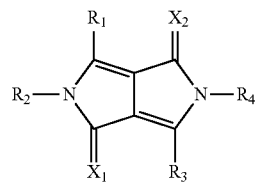

In addition, the following compound is preferably used as the nitrogen-containing aromatic polycyclic compound for use as the electron transporting compound:

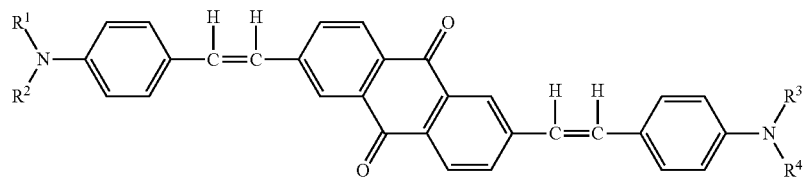

wherein R$_1$ to R$_4$ each independently represents a hydrogen atom, a substituted or unsubstituted aliphatic group having 1 to 20 carbon atoms, a substituted or unsubstituted alicyclic group having 3 to 20 carbon atoms, a substituted or unsubstituted aromatic ring group having 6 to 50 carbon atoms, or a substituted or unsubstituted heterocyclic group having 3 to 50 carbon atoms; and X$_1$ and X$_2$ each independently represents an oxygen atom, a sulfur atom, or dicyanomethylene group.

Further, the following compound is also suitable as the electron transporting compound:

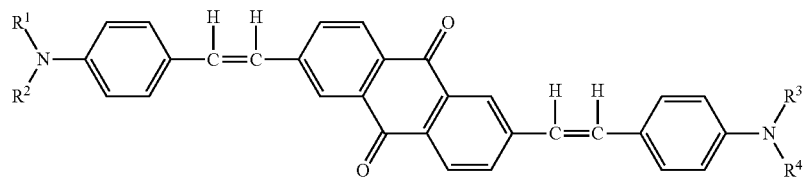

wherein R$^1$, R$^2$, R$^3$, and R$^4$ may be the same or different and each represents an aromatic hydrocarbon group or a fused aromatic hydrocarbon group each represented by the following formula:

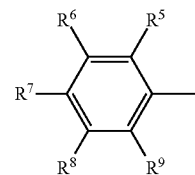

wherein R$^5$, R$^6$, R$^7$, R$^8$, and R$^9$ may be the same or different and each represents a hydrogen atom, a saturated or unsaturated alkoxyl group having 1 to 20 carbon atoms, a saturated or unsaturated alkyl group having 1 to 20 carbon atoms, an amino group, or an alkylamino group having 1 to 20 carbon atoms. At least one of R$^5$, R$^6$, R$^7$, R$^8$, and R$^9$ represents a group other than a hydrogen atom.

Further, a polymer having the nitrogen-containing heterocyclic group or the nitrogen-containing heterocyclic derivative is also usable as the electron transporting compound.

The electron transporting layer in the organic EL device of the invention preferably comprises at least one compound selected from the nitrogen-containing heterocyclic derivatives represented by formulae (60) to (62):

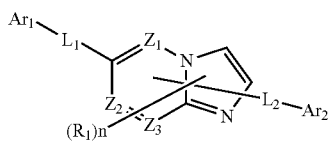

(60)

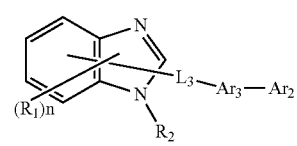

(61)

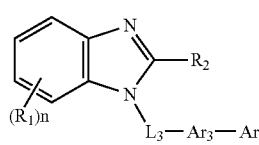

(62)

wherein $Z^1$, $Z^2$, and $Z^3$ each independently represents a nitrogen atom or a carbon atom;

$R^1$ and $R^2$ each independently represents a substituted or unsubstituted aryl group having 6 to 50 ring carbon atoms, a substituted or unsubstituted heteroaryl group having 5 to 50 ring atoms, a substituted or unsubstituted alkyl group having 1 to 20 carbon atoms, a substituted or unsubstituted haloalkyl group having 1 to 20 carbon atoms, or a substituted or unsubstituted alkoxyl group having 1 to 20 carbon atoms;

n is an integer of 0 to 5, when n is an integer of 2 or more, the groups $R^1$ may be the same or different, and the adjacent two groups $R^1$ may bond to each other to form a substituted or unsubstituted hydrocarbon ring;

$Ar^1$ represents a substituted or unsubstituted aryl group having 6 to 50 ring carbon atoms or a substituted or unsubstituted heteroaryl group having 5 to 50 ring atoms;

$Ar^2$ represents a hydrogen atom, a substituted or unsubstituted alkyl group having 1 to 20 carbon atoms, a substituted or unsubstituted haloalkyl group having 1 to 20 carbon atoms, a substituted or unsubstituted alkoxyl group having 1 to 20 carbon atoms, a substituted or unsubstituted aryl group having 6 to 50 ring carbon atoms, or a substituted or unsubstituted heteroaryl group having 5 to 50 ring atoms;

provided that one of $Ar^1$ and $Ar^2$ is a substituted or unsubstituted fused aromatic hydrocarbon ring group having 10 to 50 ring carbon atoms or a substituted or unsubstituted fused aromatic heterocyclic group having 9 to 50 ring atoms;

$Ar^3$ represents a substituted or unsubstituted arylene group having 6 to 50 ring carbon atoms or a substituted or unsubstituted heteroarylene group having 5 to 50 ring atoms; and $L^1$, $L^2$, and $L^3$ each independently represents a single bond, a substituted or unsubstituted arylene group having 6 to 50 ring carbon atoms or a substituted or unsubstituted divalent fused aromatic heterocyclic group having 9 to 50 ring atoms.

Examples of the aryl group having 6 to 50 ring carbon atoms include phenyl group, naphthyl group, anthryl group, phenanthryl group, naphthacenyl group, chrysenyl group, pyrenyl group, a biphenyl group, terphenyl group, tolyl group, fluoranthenyl group, and fluorenyl group.

Examples of the heteroaryl group having 5 to 50 ring atoms include pyrrolyl group, furyl group, thienyl group, silolyl group, pyridyl group, quinolyl group, isoquinolyl group, benzofuryl group, imidazolyl group, pyrimidyl group, carbazolyl group, selenophenyl group, oxadiazolyl group, triazolyl group, pyrazinyl group, pyridazinyl group, triazinyl group, quinoxalinyl group, acridinyl group, imidazo[1,2-a]pyridinyl group, and imidazo[1,2-a]pyrimidinyl.

Examples of the alkyl group having 1 to 20 carbon atoms include methyl group, ethyl group, propyl group, butyl group, pentyl group, and hexyl group.

Examples of the haloalkyl group having 1 to 20 carbon atoms include the groups obtained by replacing one or more hydrogen atoms of the alkyl group mentioned above with at least one halogen atom selected from fluorine, chlorine, iodine, and bromine.

Examples of the alkyl moiety of the alkoxyl group having 1 to 20 carbon atoms include the alkyl group mentioned above.

Examples of the arylene groups having 6 to 50 ring carbon atoms include the groups obtained by removing one hydrogen atom from the aryl group mentioned above.

Examples of the divalent fused aromatic heterocyclic group having 9 to 50 ring atoms include the groups obtained by removing one hydrogen atom from the fused aromatic heterocyclic group mentioned above as the heteroaryl group.

The thickness of the electron transporting layer is preferably 1 to 100 nm, but not particularly limited thereto.

Preferred examples of the material for an electron injecting layer optionally formed adjacent to the electron transporting layer include, in addition to the nitrogen-containing ring derivative, an inorganic compound, such as an insulating material and a semiconductor. The electron injecting layer containing the insulating material or the semiconductor effectively prevents the leak of electric current to enhance the electron injecting properties.

The insulating material is preferably at least one metal compound selected from the group consisting of alkali metal chalcogenides, alkaline earth metal chalcogenides, alkali metal halides and alkaline earth metal halides. The alkali metal chalcogenide, etc. mentioned above are preferred because the electron injecting properties of the electron injecting layer are further enhanced. Examples of preferred alkali metal chalcogenide include $Li_2O$, $K_2O$, $Na_2S$, $Na_2Se$ and $Na_2O$, and examples of preferred alkaline earth metal chalcogenide include CaO, BaO, SrO, BeO, BaS and CaSe. Examples of preferred alkali metal halide include LiF, NaF, KF, LiCl, KCl and NaCl. Examples of the alkaline earth metal halide include fluorides, such as $CaF_2$, $BaF_2$, $SrF_2$, $MgF_2$ and $BeF_2$, and halides other than fluorides.

Examples of the semiconductor include oxides, nitrides or oxynitrides of at least one element selected from the group consisting of Ba, Ca, Sr, Yb, Al, Ga, In, Li, Na, Cd, Mg, Si, Ta, Sb and Zn. The semiconductor may be used alone or in combination of two or more. The inorganic compound included in the electron injecting layer preferably forms a microcrystalline or amorphous insulating thin film. If the electron injecting layer is formed from such an insulating thin film, the pixel defects, such as dark spots, can be decreased because a more uniform thin film is formed. Examples of such inorganic compound include the alkali metal chalcogenide, the alkaline earth metal chalcogenide, the alkali metal halide and the alkaline earth metal halide.

When using the insulating material or the semiconductor, the thickness of its layer is preferably about 0.1 to 15 nm. The electron injecting layer in the invention may contain the electron-donating dopant mentioned above.

Hole Transporting Layer

The hole injecting/transporting layer is an organic layer formed between the light emitting layer and the anode and has a function of transporting holes from the anode to the light emitting layer. When the hole transporting layer is formed by two or more layers, the layer closer to the anode may be defined as the hole injecting layer in some cases. The hole injecting layer has a function of efficiently injecting holes from the anode to the organic layer unit.

Another preferred material for the hole transporting layer may include an aromatic amine compound, for example, an aromatic amine derivative represented by formula (I):

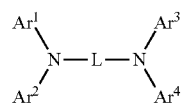
(I)

wherein each of $Ar^1$ to $Ar^4$ represents a substituted or unsubstituted aromatic hydrocarbon group or fused aromatic hydrocarbon group each having 6 to 50 ring carbon atoms, a substituted or unsubstituted aromatic heteroaryl group or fused aromatic heteroaryl group each having 5 to 50 ring atoms, or a group wherein the aromatic hydrocarbon group or fused aromatic hydrocarbon group is bonded to the aromatic heteroaryl group or fused aromatic heteroaryl group.

L represents a substituted or unsubstituted aromatic hydrocarbon group or fused aromatic hydrocarbon group each having 6 to 50 ring carbon atoms or a substituted or unsubstituted aromatic heteroaryl group or fused aromatic heteroaryl group each having 5 to 50 ring atoms.

Examples of the compound represented by formula (I) are shown below.

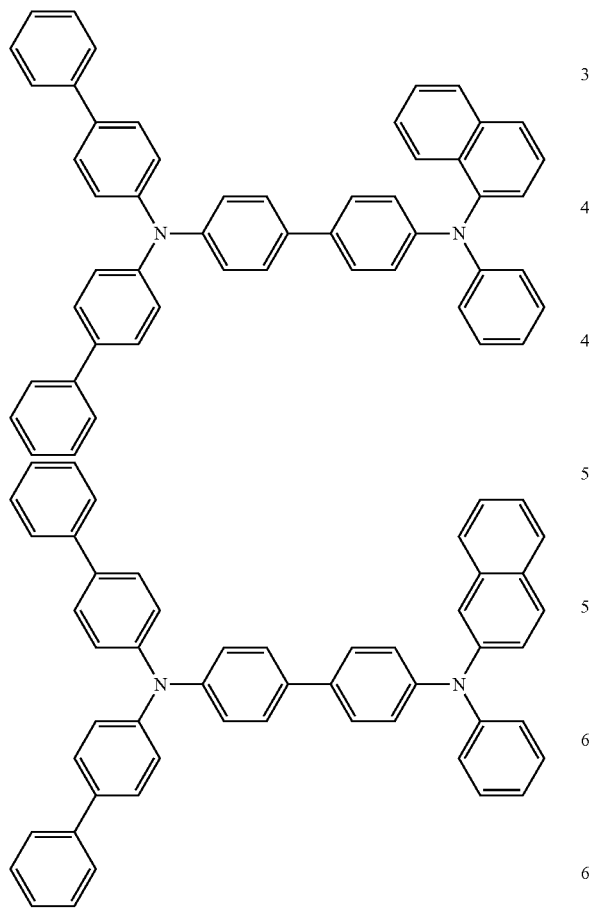

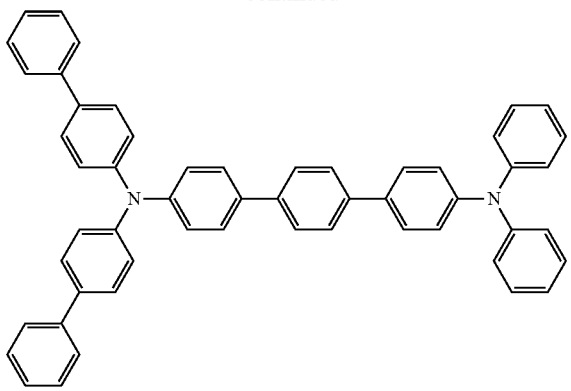

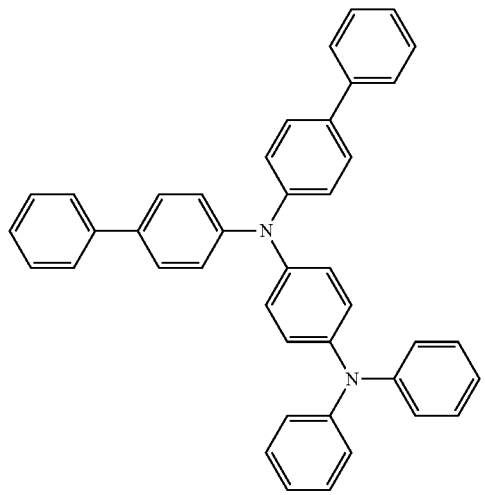

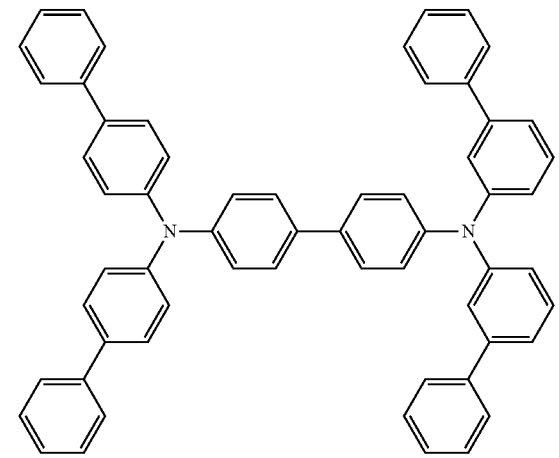

105
-continued
106
-continued
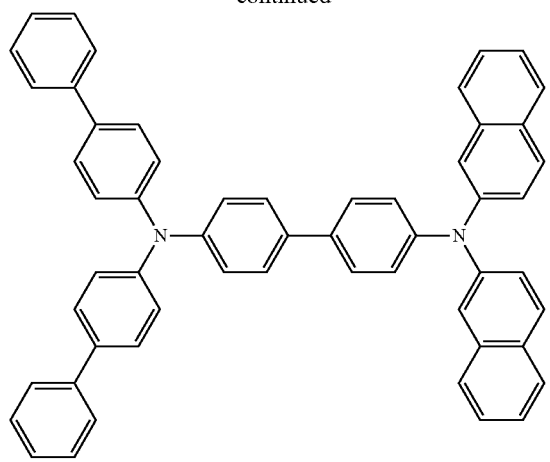
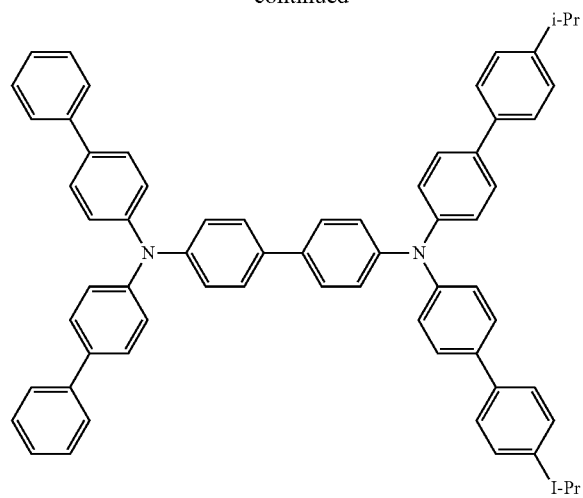
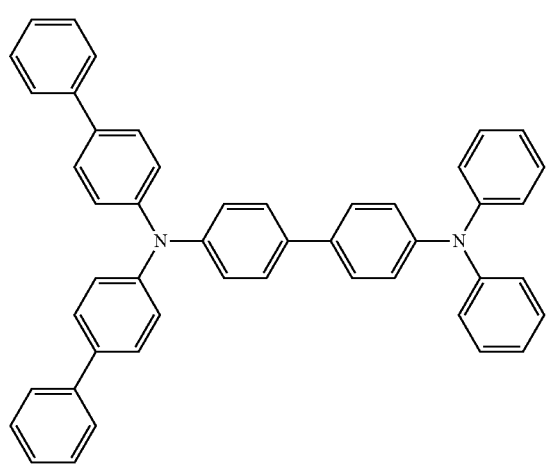
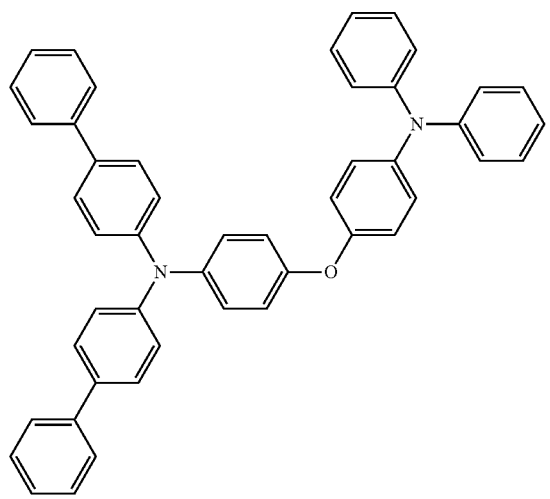
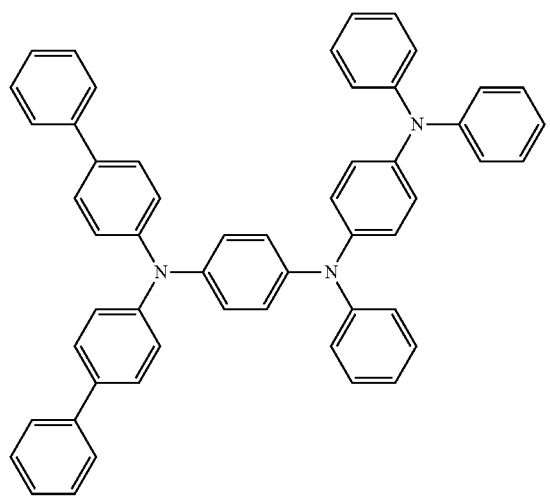

107
-continued
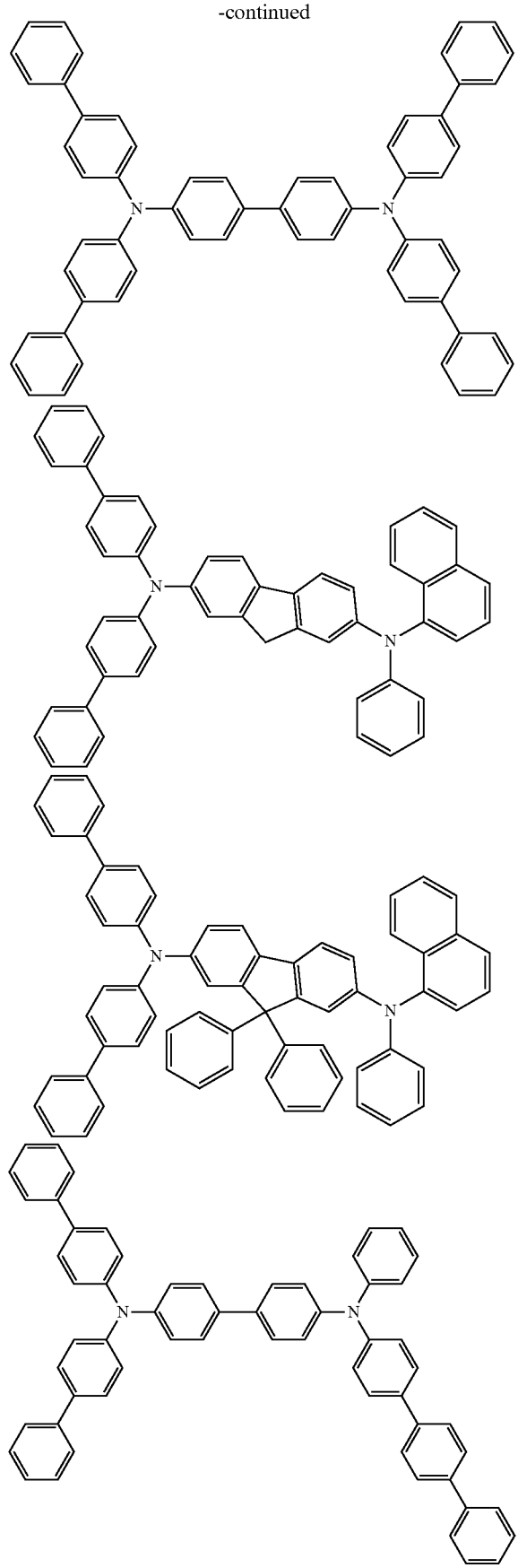
108
-continued
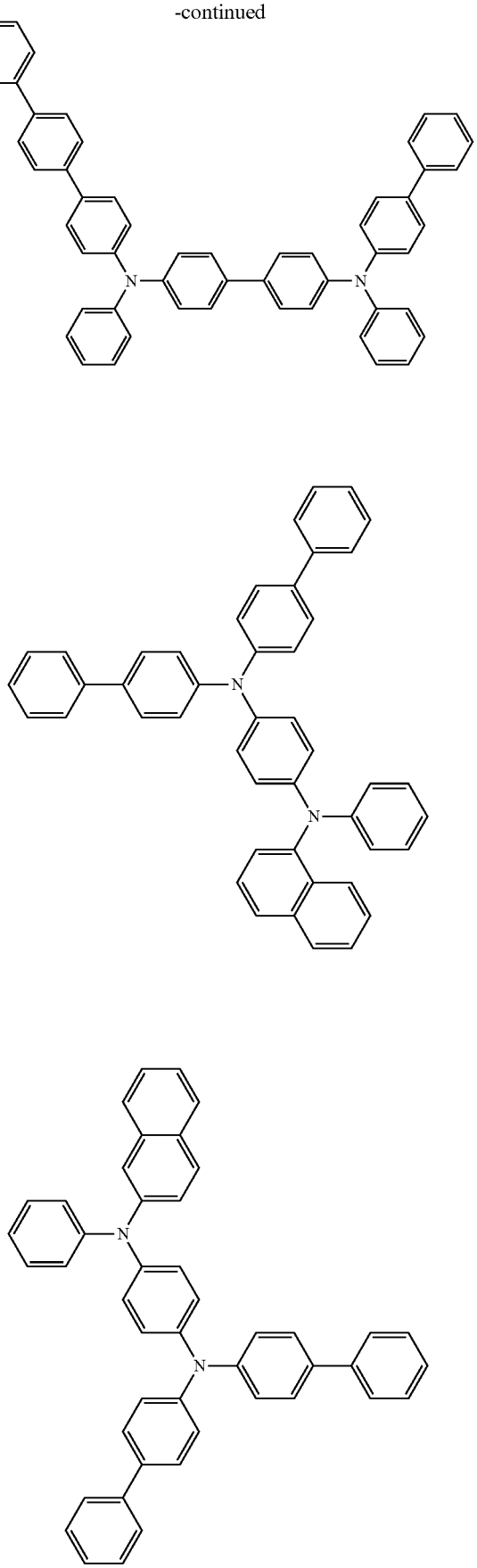

109
-continued
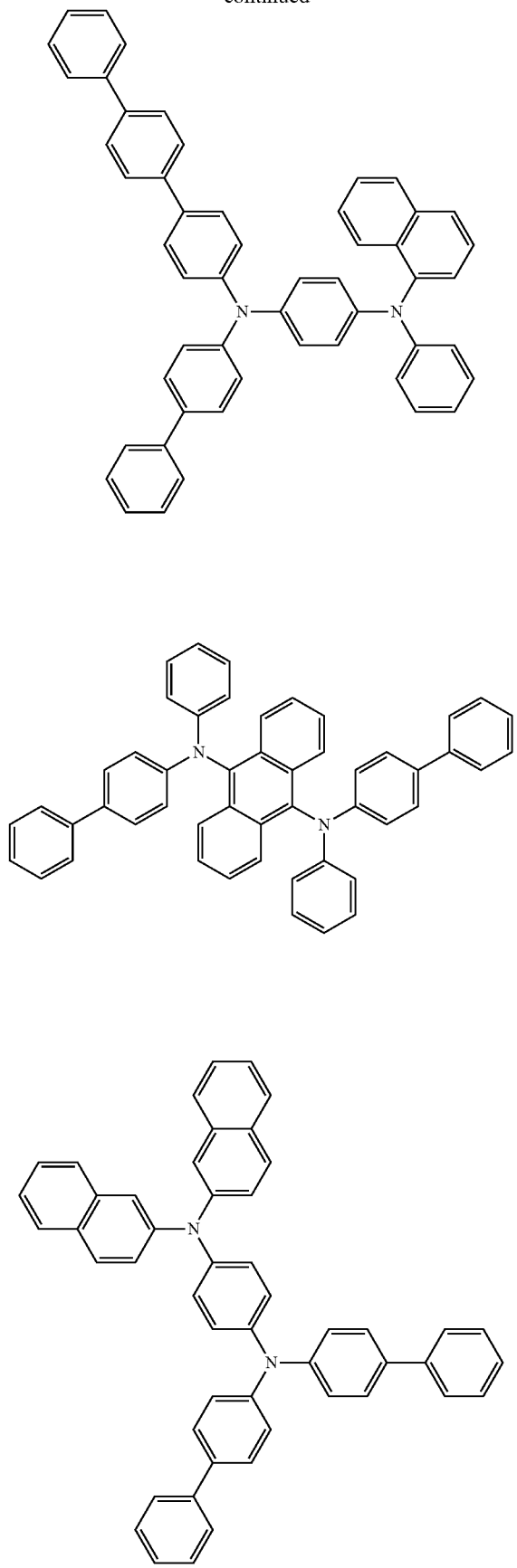
110
-continued
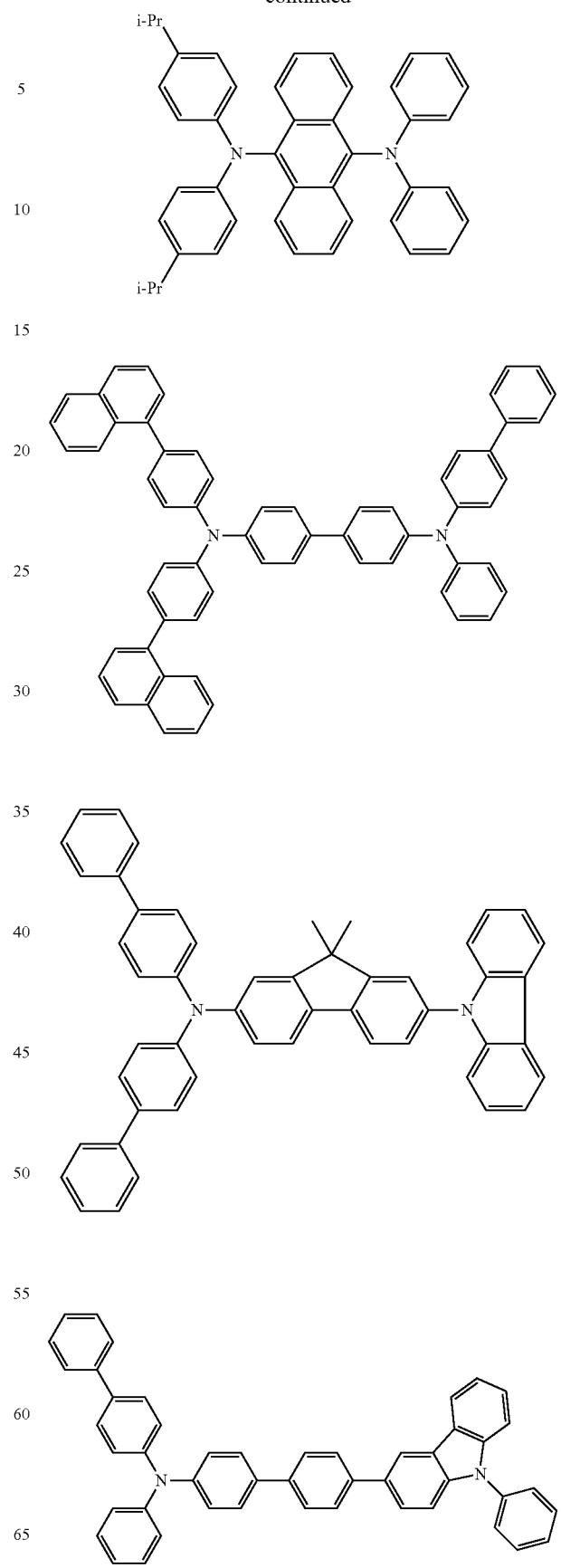

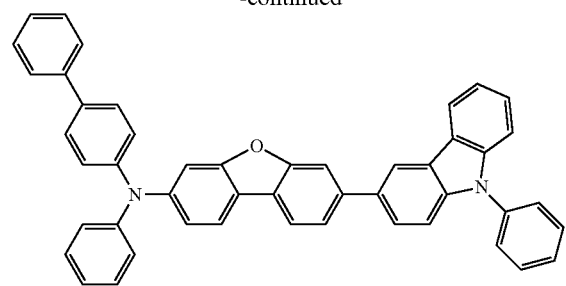
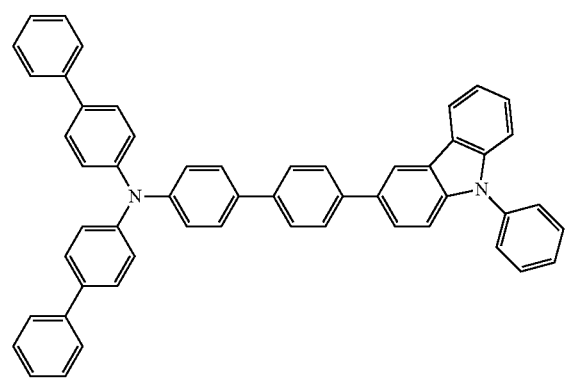
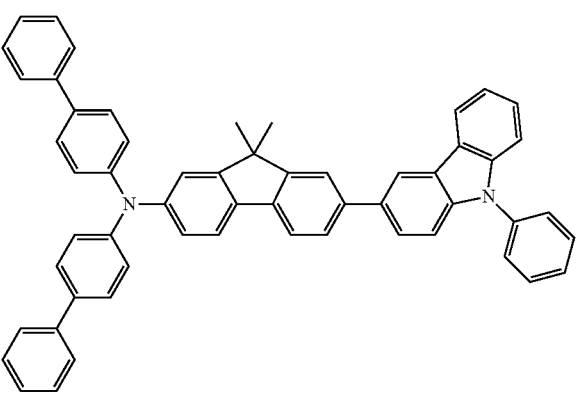
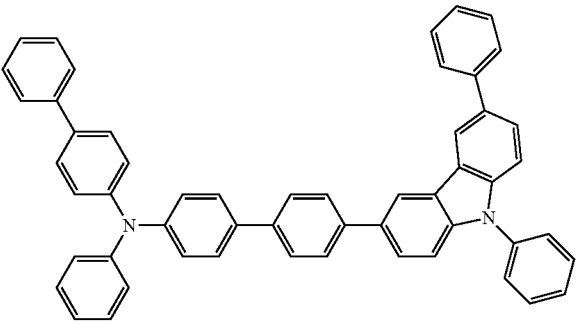
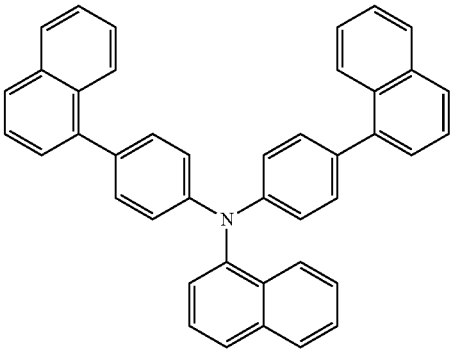
An aromatic amine represented by formula (II) is also preferably used to form the hole transporting layer:
$$Ar^2-N\begin{smallmatrix}Ar^1\\ \\Ar^3\end{smallmatrix} \quad (II)$$
wherein $Ar^1$ to $Ar^3$ are the same as defined with respect to $Ar^1$ to $Ar^4$ of formula (I). Examples of the compound represented by formula (II) are shown below, although not limited thereto.

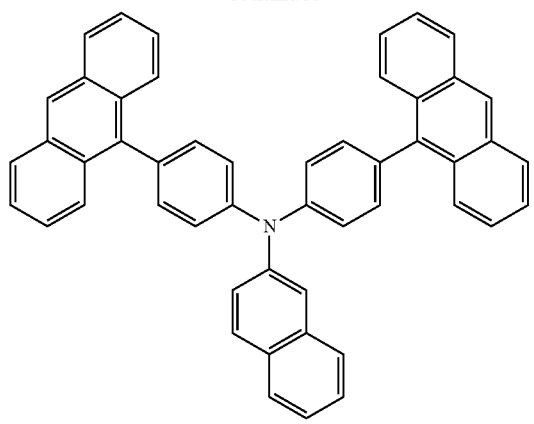
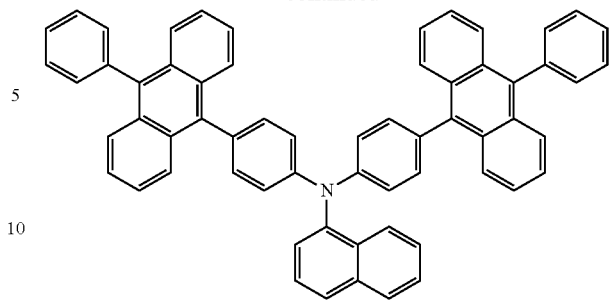
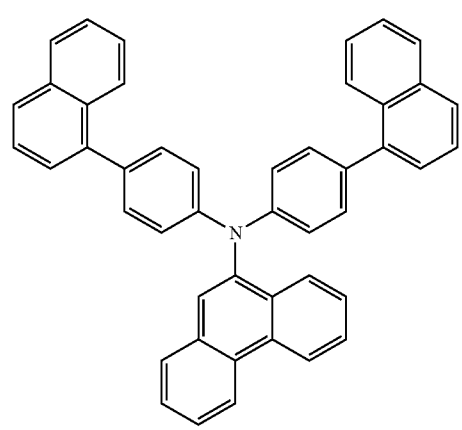
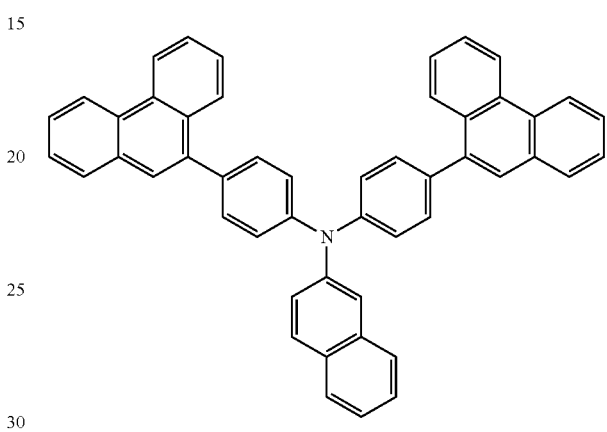
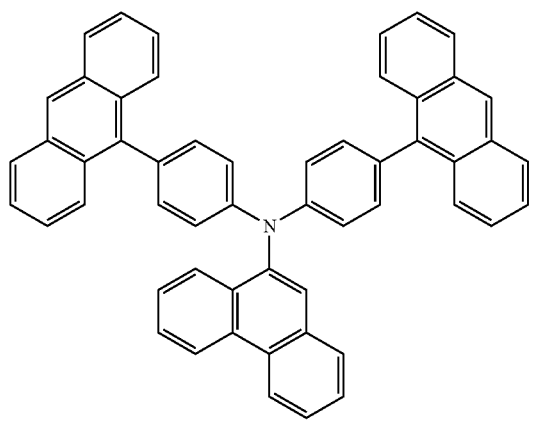
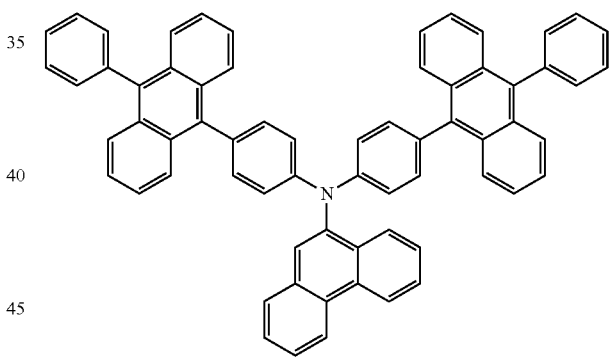
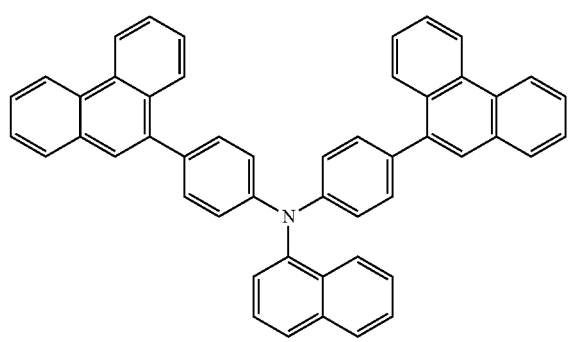
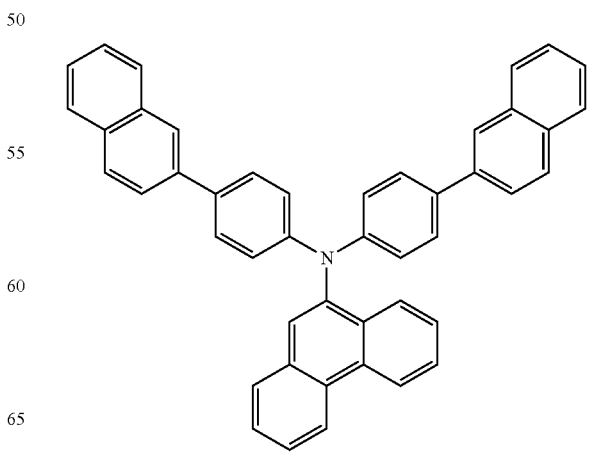

115
-continued
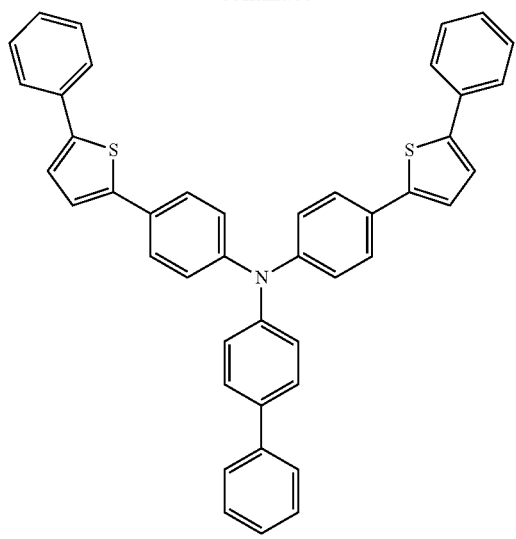
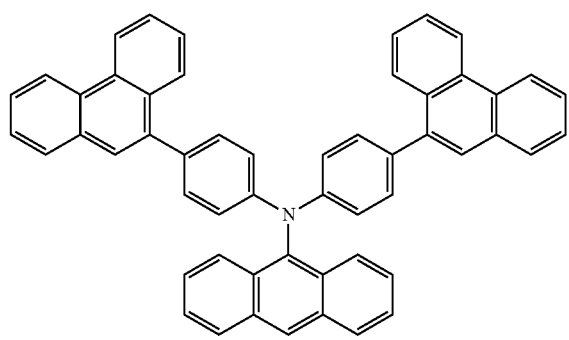
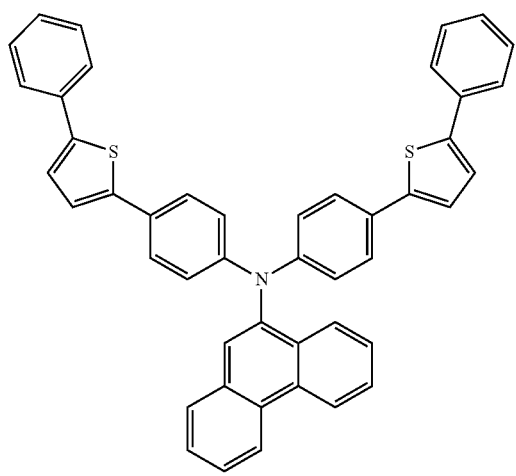
116
-continued
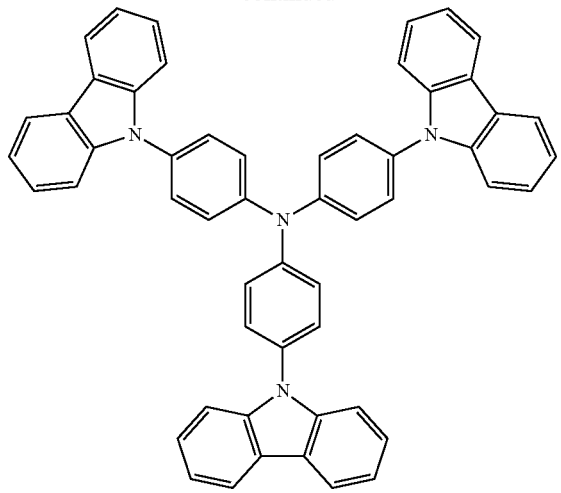
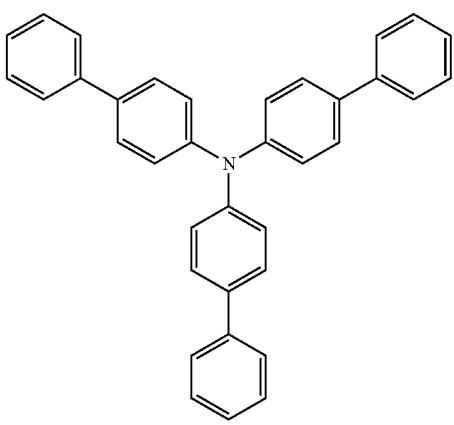
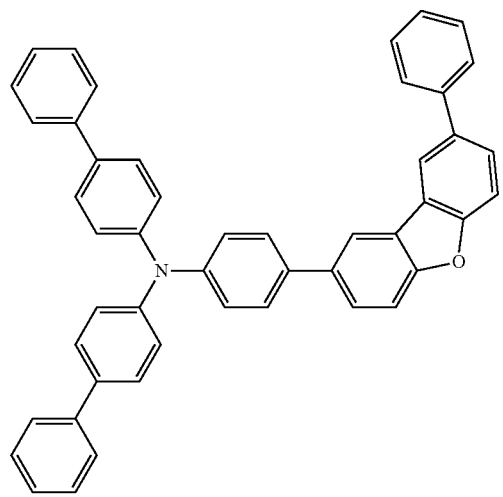

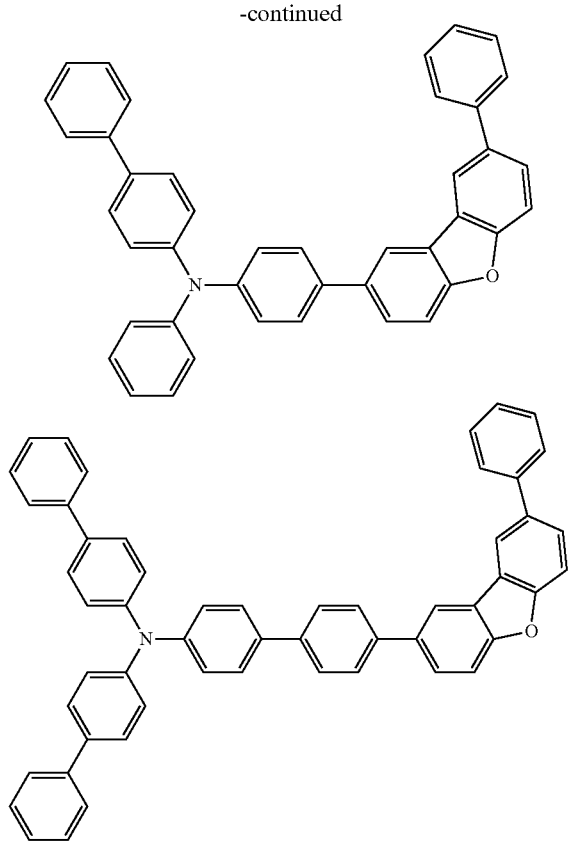

The hole transporting layer may be made into two-layered structure of a first hole transporting layer (anode side) and a second hole transporting layer (cathode side).

The thickness of the hole transporting layer is preferably 10 to 200 nm, although not particularly limited thereto.

The organic EL device of the invention may have a layer comprising an electron-accepting compound which is attached to the anode side of each of the hole transporting layer or the first hole transporting layer. With such a layer, it is expected that the driving voltage is lowered and the production cost is reduced.

The electron-accepting compound is preferably a compound represented by formula (A):

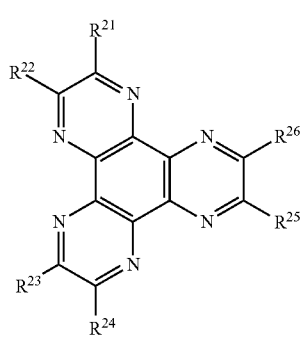

(A)

wherein $R^{21}$ to $R^{26}$ may be the same or different and each independently represents a cyano group, —$CONH_2$, a carboxyl group, or —$COOR^{27}$ wherein $R^{27}$ represents an alkyl group having 1 to 20 carbon atoms or a cycloalkyl group having 3 to 20 carbon atoms. One or more of a pair of $R^{21}$ and $R^{22}$, a pair of $R^{23}$ and $R^{24}$, and a pair of $R^{25}$ and $R^{26}$ may bond to each other to form a group represented by —CO—O—CO—.

Examples of $R^{27}$ include methyl group, ethyl group, n-propyl group, isopropyl group, n-butyl group, isobutyl group, t-butyl group, cyclopentyl group, and cyclohexyl group.

The thickness of the layer comprising the electron-accepting compound is preferably 5 to 20 nm, although not particularly limited thereto.

N/P Doping

The carrier injecting properties of the hole transporting layer and the electron transporting layer can be controlled by, as described in JP 3695714B, the doping (n) with a donor material or the doping (p) with an acceptor material.

A typical example of the n-doping is an electron transporting material doped with a metal, such as Li and Cs, and a typical example of the p-doping is a hole transporting material doped with an acceptor material, such as $F_4TCNQ$.

Space Layer

For example, in an organic EL device wherein a fluorescent light emitting layer and a phosphorescent light emitting layer are laminated, a space layer is disposed between the fluorescent light emitting layer and the phosphorescent light emitting layer to prevent the diffusion of excitons generated in the phosphorescent light emitting layer to the fluorescent light emitting layer or to control the carrier balance. The space layer may be disposed between two or more phosphorescent light emitting layers.

Since the space layer is disposed between the light emitting layers, a material combining the electron transporting ability and the hole transporting ability is preferably used for forming the space layer. To prevent the diffusion of triplet energy in the adjacent phosphorescent light emitting layer, the triplet energy of the material for the space layer is preferably 2.6 eV or more. The materials described with respect to the hole transporting layer are usable as the material for the space layer.

Blocking Layer

The organic EL device of the invention preferably has a blocking layer, such as an electron blocking layer, a hole blocking layer, and a triplet blocking layer, which is disposed adjacent to the light emitting layer. The electron blocking layer is a layer which prevents the diffusion of electrons from the light emitting layer to the hole transporting layer. The hole blocking layer is a layer which prevents the diffusion of holes from the light emitting layer to the electron transporting layer.

The triplet blocking layer, as described below, prevents the diffusion of triplet excitons generated in the light emitting layer to adjacent layers and has a function of confining the triplet excitons in the light emitting layer, thereby preventing the deactivation of energy on molecules other than the emitting dopant of triplet excitons, for example, on molecules in the electron transporting layer.

If a device having a triplet blocking layer satisfies the following energy relationship:

$$E^T_d < E^T_{TB}$$

wherein $E^T_d$ is the triplet energy of the phosphorescent dopant in the light emitting layer and $E^T_{TB}$ is the triplet energy of the compound forming the triplet blocking layer, the triplet excitons of phosphorescent dopant are confined (not diffuse to other molecules). Therefore, the energy deactivation process other than the emission on the phosphorescent dopant may be prevented to cause the emission with high efficiency. However, even in case of satisfying the relationship of $E^T_d < E^T_{TB}$, the triplet excitons may move into other molecules if the energy difference ($\Delta E^T = E^T_{TB} - E^T_d$) is small, because the energy difference $\Delta E^T$ may be overcome by the absorption of ambient heat energy when driving a device at around room temperature as generally employed in practical drive of device. As compared with the fluorescent emission, the phosphorescent emission is relatively likely to be affected by the diffusion of excitons due to the heat absorption because the lifetime of triplet excitons is longer. Therefore, as for the energy difference $\Delta E^T$, the larger as compared with the heat energy of room temperature, the better. The energy difference $\Delta E^T$ is more preferably 0.1 eV or more and particularly preferably 0.2 eV or more.

The triplet energy referred to herein was determined as follows.

A sample was dissolved in EPA solvent (diethyl ether: isopentane:ethanol=5:5:2 (by volume)) in a concentration of 10 μmol/L to prepare a specimen for phosphorescence measurement. The specimen for phosphorescence measurement was placed in a quartz cell and irradiated with excitation ray at 77 K, and the emitted phosphorescence was measured. Using the measured result, the triplet energy was determined as the value calculated from the following conversion formula:

$$E^T(\text{eV}) = 1239.85/\lambda_{edge}$$

wherein $\lambda_{edge}$ is determined as follows.

On the phosphorescence spectrum with a vertical axis of phosphorescent intensity and a horizontal axis of wavelength, a line tangent to the rising portion at the short-wavelength side of the phosphorescent spectrum was drawn, and the wavelength (nm) at the intersection of the tangent line and the horizontal axis was expressed by "$\lambda_{edge}$."

A material satisfying the following relationship:

$$A_b - A_h \leq 0.1 \text{ eV}$$

wherein $A_b$ is the affinity of the blocking layer material and $A_h$ is the affinity of the host material in the light emitting layer, is preferably used as the host material in the light emitting layer.

The affinity Af (electron affinity) is defined as the amount of energy released or absorbed when one electron is added to a molecule. The electron affinity is expressed by a positive sign when the energy is released and a negative sign when the energy is absorbed. Using the ionization potential Ip and the optical energy gap Eg(S), the electron affinity Af is expressed by:

$$Af = Ip - Eg(S).$$

The ionization potential Ip is the amount of energy required to remove an electron from a compound to ionize the compound. In the present, invention, Ip is a positive value measured by a photoelectronic spectrophotometer (AC-3, manufactured by Riken Keiki Co., Ltd.) in the atmosphere. The optical energy gap Eg(S) is the difference between the conduction level and the valence level. In the present invention, Eg(S) is a positive value which is determined by measuring an ultraviolet/visible absorption spectrum of a diluted dichloromethane solution of a material, drawing a line tangent to the spectrum at the long-wavelength side, and converting the wavelength of the intersection between the tangent line and the base line (zero absorption) to the unit of energy.

The electron mobility of the material for the triplet blocking layer is preferably $10^{-6}$ cm$^2$/Vs or more at an electric field strength in a range of 0.04 to 0.5 MV/cm. There are several methods for measuring the electron mobility of organic material, for example, Time of Flight method. In the present invention, the electron mobility is determined by impedance spectroscopy.

The electron mobility of the electron injecting layer is preferably $10^{-6}$ cm$^2$/Vs or more at an electric field strength in a range of 0.04 to 0.5 MV/cm. Within the above range, the injection of electrons from the cathode to the electron transporting layer is promoted and the injection of electrons to the adjacent blocking layer and light emitting layer is also promoted, thereby enabling to drive a device at lower voltage.

The organic EL device of the invention is applicable to an emitting flat panel, such as a flat panel display of a wall-mount television, a photocopier, a printer, a backlight of liquid crystal display, a light source of instruments, a display board, a beacon light, etc. The material of the invention is, in addition to an organic EL devices, applicable to an electrophotographic photoreceptor, a photoelectric converter, a solar cell, an image sensor, etc.

EXAMPLES

Intermediate Synthesis 1

Synthesis of Intermediate 1

Under an argon atmosphere, into a mixture of 28.3 g of 4-iodobromobenzene (100.0 mmol), 22.3 g of dibenzofuran-4-boronic acid (105.0 mmol), and 2.31 g of Pd[PPh$_3$]$_4$ (2.00 mmol), 150 ml of toluene, 150 ml of dimethoxyethane, and 150 ml of a 2 M aqueous solution of Na$_2$CO$_3$ (300.0 mmol) were added, and the resultant mixture was stirred for 10 h by refluxing under heating.

After the reaction, the reaction mixture was extracted with dichloromethane in a separation funnel. The organic layer was dried over MgSO$_4$, filtered, and concentrated. The concentrate was purified by silica gel column chromatography to obtain 26.2 g of white solid, which was identified as Intermediate 1 by FD-MS analysis (yield: 81%).

Intermediate 1

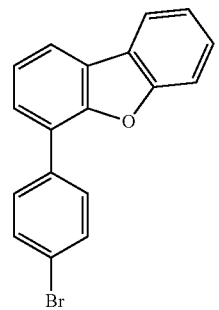

Intermediate Synthesis 2

Synthesis of Intermediate 2

Under an argon atmosphere, into a mixture of 18.5 g of 1-acetamide (313.0 mmol), 32.3 g of Intermediate 1 (100.0 mmol), 54.4 g of potassium carbonate (394.0 mmol), and 1.25 g of copper powder (20.0 mmol), 200 ml of decalin was added, and the resultant mixture was stirred at 190° C. for 4 days by refluxing under heating.

After the reaction, the reaction mixture was cooled, 200 ml of toluene was added, and then the insolubles were collected by filtration. The collected insolubles were diluted with 500 ml of chloroform. After removing the insolubles, the obtained solution was treated with activated carbon and concentrated.

The concentrate was recrystallized from acetone to obtain 18.1 g of white solid, which was identified as Intermediate 2 by FD-MS analysis (yield: 60%).

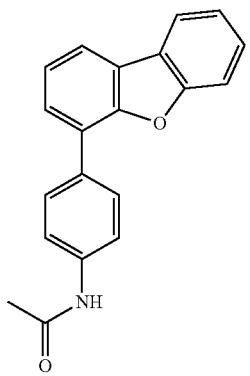

Intermediate 2

Intermediate Synthesis 3

Synthesis of Intermediate 3

Into 18.0 g of Intermediate 2 (60.0 mmol), 21.6 ml of water (1.2 mol), 60 ml of ethanol, and 120 ml of xylene were added, and the resultant mixture was stirred. After further adding 20.0 g of potassium hydroxide (360.0 mmol), the mixture was stirred at 120° C. for 8 h by refluxing under heating.

After the reaction, the reaction mixture was poured into a separation funnel, 100 ml of a saturated saline was added, and then the reaction mixture was extracted with toluene. The organic layer was dried over MgSO₄, filtered, and concentrated. The concentrate was recrystallized from xylene to obtain 14.1 g of white solid, which was identified as Intermediate 3 by FD-MS analysis (yield: 90%).

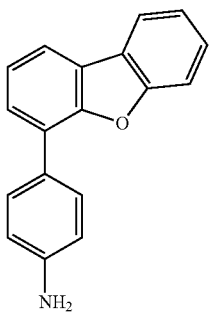

Intermediate 3

Intermediate Synthesis 4

Synthesis of Intermediate 4

The reaction was conducted in the same manner as in Intermediate Synthesis 2 except for using 67.8 g of Intermediate 1 (209.8 mmol) to obtain 33.0 g of white crystal, which was identified as Intermediate 4 by FD-MS analysis (yield: 61%).

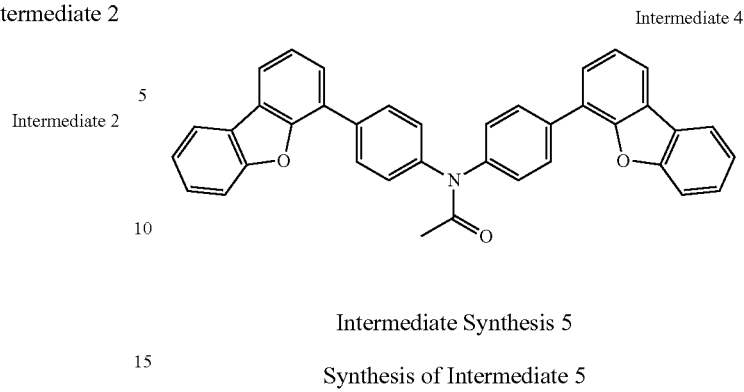

Intermediate 4

Intermediate Synthesis 5

Synthesis of Intermediate 5

The reaction was conducted in the same manner as in Intermediate Synthesis 3 except for using 33.0 g Intermediate 4 (60.7 mmol) in place of Intermediate 2 to obtain 19.8 g of white crystal, which was identified as Intermediate 5 by FD-MS analysis (yield: 65%).

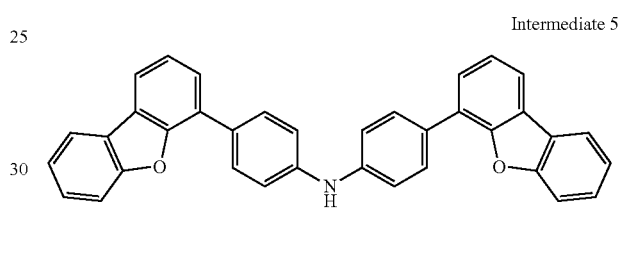

Intermediate 5

Intermediate Synthesis 6

Synthesis of Intermediate 6

Under a nitrogen atmosphere, 150 g of dibenzofuran (0.89 mol) was dissolved in 1000 ml of acetic acid under heating. After adding 188 g of bromine (1.18 mol), the solution was stirred at room temperature for 20 h. The precipitated crystals were collected by filtration and washed successively with acetic acid and water. The crude product was repeatedly recrystallized from methanol to obtain 66.8 g of white crystal, which was identified as Intermediate 6 by FD-MS analysis (yield: 30%).

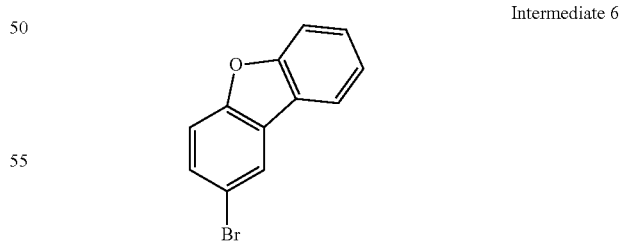

Intermediate 6

Intermediate Synthesis 7

Synthesis of Intermediate 7

Under an argon atmosphere, 400 ml of dry THF was added to 24.7 g of Intermediate 6 (100.0 mmol) and the resultant mixture was cooled to −40° C. Then, 63 ml of a 1.6 M hexane solution of n-butyl lithium (100.0 mmol) was added gradually. The resultant solution was stirred for one hour while heating to 0° C. and then cooled again to −78° C. Thereafter, 50 ml of a solution of 26.0 g of trimethyl borate (250.0 mmol) in 50 ml of dry THF was added dropwise. After the dropwise addition, the solution was stirred at room temperature for 5 h. After adding 200 ml of a 1 N hydrochloric acid, the solution was stirred for one hour and then the water layer was removed. The organic layer was dried over MgSO$_4$ and the solvent was removed by evaporation under reduced pressure. The obtained solid was washed with toluene to obtain 15.2 g of white crystal (yield: 72%).

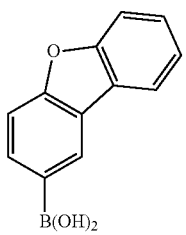

Intermediate 7

Intermediate Synthesis 8

Synthesis of Intermediate 8

Under an argon atmosphere, into a mixture of 28.3 g of 3-iodobromobenzene (100.0 mmol), 22.3 g of Intermediate 7 (105.0 mmol), and 2.31 g of Pd[PPh$_3$]$_4$ (2.00 mmol), 150 ml of toluene, 150 ml of dimethoxyethane, and 150 ml of a 2 M aqueous solution of Na$_2$CO$_3$ (300.0 mmol) were added, and the resultant mixture was stirred for 10 h by refluxing under heating.

After the reaction, the reaction mixture was extracted with dichloromethane in a separation funnel. The organic layer was dried over MgSO$_4$, filtered, and concentrated. The concentrate was purified by silica gel column chromatography to obtain 24.2 g of white solid, which was identified as Intermediate 8 by FD-MS analysis (yield: 75%).

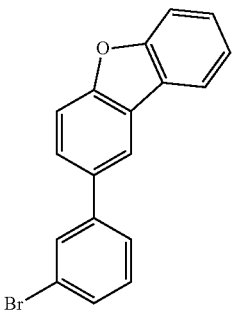

Intermediate 8

Intermediate Synthesis 9

Synthesis of Intermediate 9

Under an argon atmosphere, into a mixture of 28.3 g of 3-iodobromobenzene (100.0 mmol), 22.3 g of dibenzofuran-4-boronic acid (105.0 mmol), and 2.31 g of Pd[PPh$_3$]$_4$ (2.00 mmol), 150 ml of toluene, 150 ml of dimethoxyethane, and 150 ml of a 2 M aqueous solution of Na$_2$CO$_3$ (300.0 mmol) were added, and the resultant mixture was stirred for 10 h by refluxing under heating.

After the reaction, the reaction mixture was extracted with dichloromethane in a separation funnel. The organic layer was dried over MgSO$_4$, filtered, and concentrated. The concentrate was purified by silica gel column chromatography to obtain 22.0 g of white solid, which was identified as Intermediate 9 by FD-MS analysis (yield: 68%)

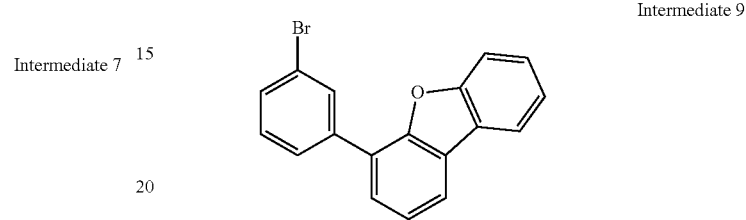

Intermediate 9

Synthesis Example 1

Production of Aromatic Amine Derivative (H1)

Under an argon atmosphere, 80 ml of dry toluene was added to a mixture of 10.0 g of Intermediate 5 (20.0 mmol), 6.5 g of Intermediate 8 (20.0 mmol), and 3.8 g of t-butoxysodium (40.0 mmol), and the resultant mixture was stirred. After further adding 0.23 g of Pd(OAc)$_2$ (1.0 mmol) and 0.40 g of P(tBu)$_3$ (2.0 mmol), the mixture was refluxed under heating at 80° C. for 4 h.

After the reaction, the reaction mixture was cooled to 50° C. and filtered through celite and silica gel. The filtrate was concentrated and the concentrate was purified by silica gel column chromatography to obtain white solid. The crude product was recrystallized from toluene to obtain 9.9 g white crystal, which was identified as the aromatic amine derivative (H1) by FD-MS analysis (yield: 67%)

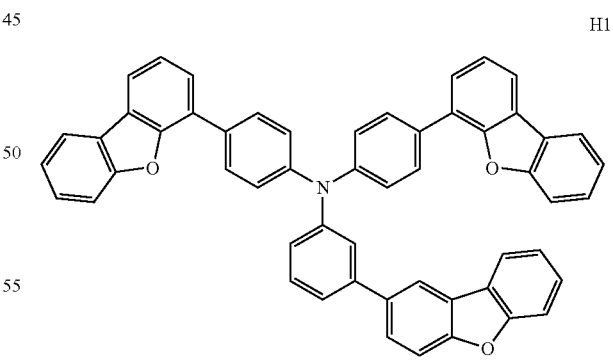

H1

Synthesis Example 2

Production of Aromatic Amine Derivative (H2)

The reaction was conducted in the same manner as in Synthesis Example 1 except for using 6.5 g of Intermediate 9 in place of Intermediate 8 to obtain 8.9 g of white crystal,

H2

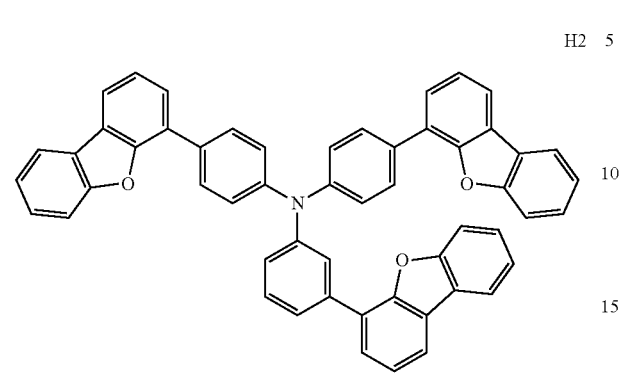

Synthesis Example 3

Production of Aromatic Amine Derivative (H3)

The reaction was conducted in the same manner as in Synthesis Example 1 except for using 6.4 g of 9-(3-bromophenyl)-9H-carbazole in place of Intermediate 8 to obtain 9.5 g of white crystal, which was identified as the aromatic amine derivative (H3) by FD-MS analysis (yield: 64%).

H3

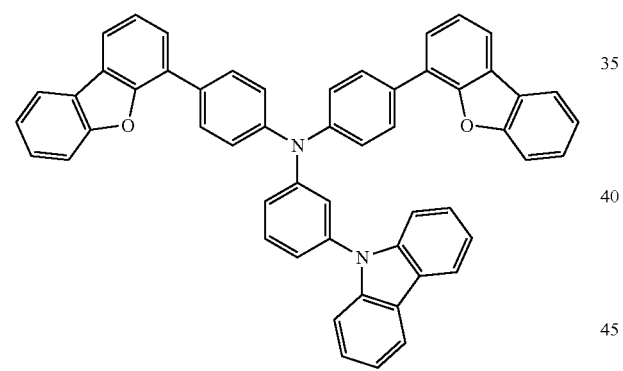

Synthesis Example 4

Production of Aromatic Amine Derivative (H4)

Under an argon atmosphere, 80 ml of dry toluene was added to a mixture of 5.2 g of Intermediate 3 (20.0 mmol), 12.9 g of Intermediate 8 (40.0 mmol), and 3.8 g of t-butoxysodium (40.0 mmol), and the resultant mixture was stirred. After further adding 0.23 g of Pd(OAc)$_2$ (1.0 mmol) and 0.40 g of P(tBu)$_3$ (2.0 mmol), the mixture was refluxed under heating at 80° C. for 4 h.

After the reaction, the reaction mixture was cooled to 50° C. and filtered through celite and silica gel. The filtrate was concentrated and the concentrate was purified by silica gel column chromatography to obtain white solid. The crude product was recrystallized from toluene to obtain 7.9 g of white crystal, which was identified as the aromatic amine derivative (H4) by FD-MS analysis (yield: 53%).

H4

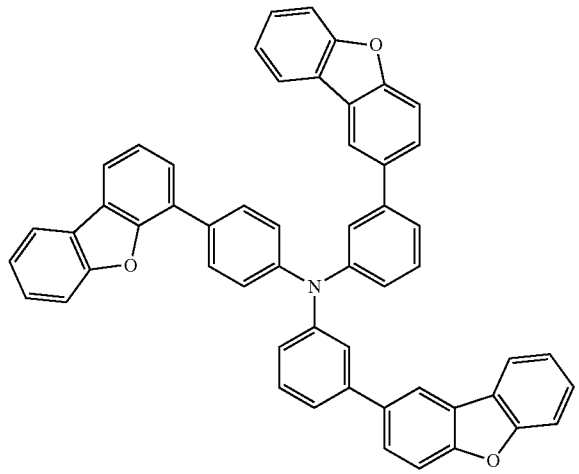

Synthesis Example 5

Production of Aromatic Amine Derivative (H5)

The reaction was conducted in the same manner as in Synthesis Example 4 except for using 12.9 g of Intermediate 9 in place of Intermediate 8 to obtain 8.1 g of white crystal, which was identified as the aromatic amine derivative (H5) by FD-MS analysis (yield: 54%)

H5

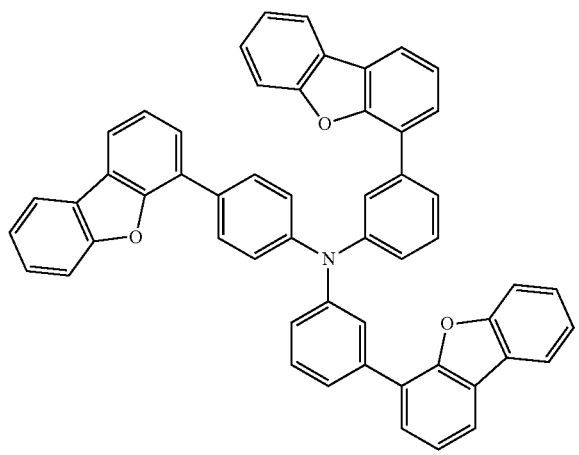

Example 1

Production of Organic EL Device

A glass substrate with an ITO transparent electrode having a size of 25 mm×75 mm×1.1 mm (manufactured by GEO-MATEC Co., Ltd.) was ultrasonically cleaned in isopropyl alcohol for 5 min and then UV (ultraviolet)/ozone cleaned for 30 min. The thickness of the ITO transparent electrode was 130 nm.

The cleaned glass substrate with the transparent electrode line was mounted on the substrate holder of a vacuum deposition apparatus. First, the following electron-accepting compound (A) was vapor-deposited onto the surface on the side where the transparent electrode line was formed so as to cover the transparent electrode, thereby forming a film A having a thickness of 5 nm. On the film A, the following aromatic amine derivative (X1) was vapor-deposited as a first hole transporting material to form a first hole transporting layer having a thickness of 80 nm.

Successively after forming the first hole transporting layer, the aromatic amine derivative (H1) obtained in Synthesis Example 1 was vapor-deposited as a second hole transporting material to form a second hole transporting layer having a thickness of 15 nm.

On the second hole transporting layer, the compound (BH) (host material) and the compound (BD) (emitting dopant material) were vapor co-deposited to form a light emitting layer having a thickness of 25 nm. The concentration of the compound (BD) in the light emitting layer was 5.0% by mass. The co-deposited film works as a light emitting layer.

Successively after forming the light emitting layer, the compound (ET1) was deposited into a film having a thickness of 20 nm. Then, the compound (ET2) was deposited into a film having a thickness of 5 nm. These films work as an electron transporting layer.

Further, LiF was deposited into a film having a thickness of 1 nm at a film-forming speed of 1 Å/min to form an electron injecting electrode (cathode). On the LiF film, metallic Al was deposited to form a metal cathode having a thickness of 80 nm.

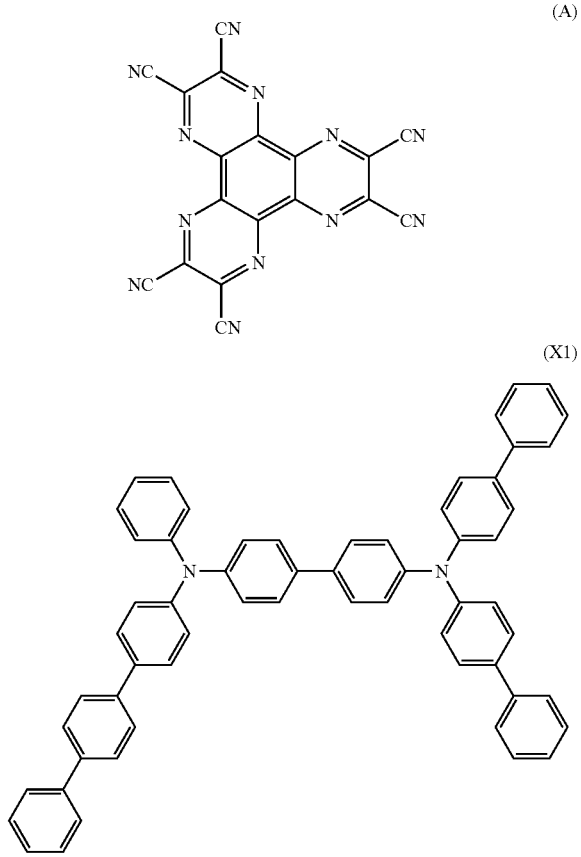

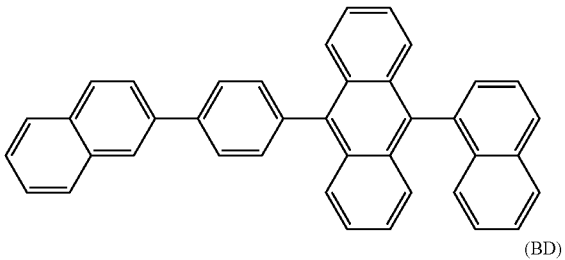

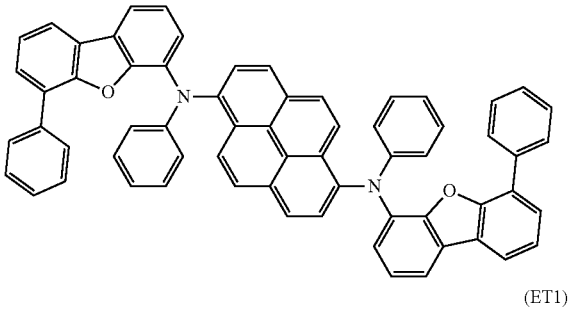

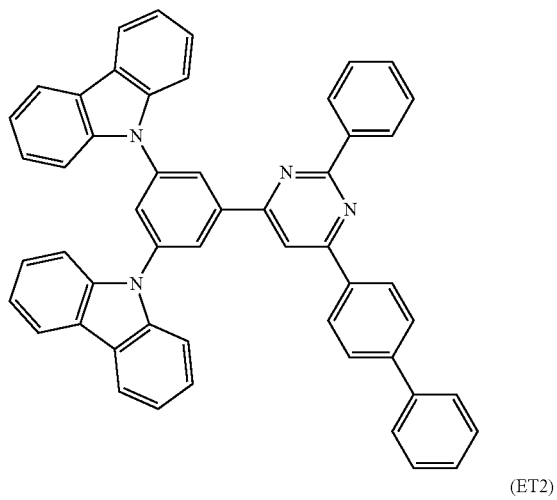

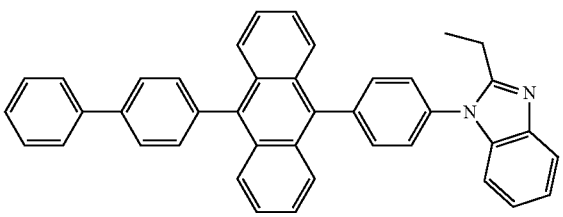

Evaluation of Emission Performance of Organic EL Device

The organic EL device thus produced was measured for the luminance (L) and the current density by allowing the device to emit light under a direct current drive, thereby determining the current efficiency (L/J) and the driving voltage (V) at a current density of 10 mA/cm$^2$. In addition, the organic EL device was measured for the lifetime at a current density of 50 mA/cm$^2$. The results are shown in Table 1.

Examples 2 to 5

Each organic EL device was produced in the same manner as in Example 1 except for using each aromatic amine derivative listed in Table 1 as the second hole transporting material in place of the aromatic amine derivative (H1). Each of the obtained organic EL devices was measured for the luminance (L) and the current density by allowing the device to emit light under a direct current drive, thereby determining the current efficiency (L/J) and the driving voltage (V) at a current density of 10 mA/cm². In addition, each organic EL device was measured for the lifetime at a current density of 50 mA/cm². The results are shown in Table 1.

Comparative Examples 1 to 4

Each organic EL device was produced in the same manner as in Example 1 except for using each of the following comparative compounds 1 to 4 as the second hole transporting material in place of the aromatic amine derivative (H1). Each of the obtained organic EL devices was measured for the luminance (L) and the current density by allowing the device to emit light under a direct current drive, thereby determining the current efficiency (L/J) and the driving voltage (V) at a current density of 10 mA/cm². In addition, each organic EL device was measured for the lifetime at a current density of 50 mA/cm². The results are shown in Table 1.

Comparative compound 1

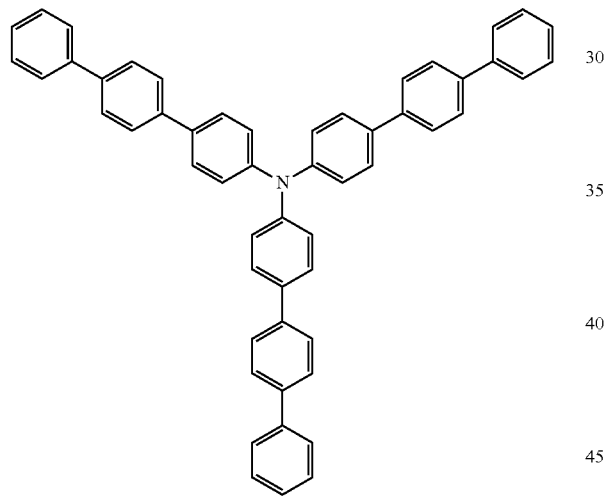

Comparative compound 2

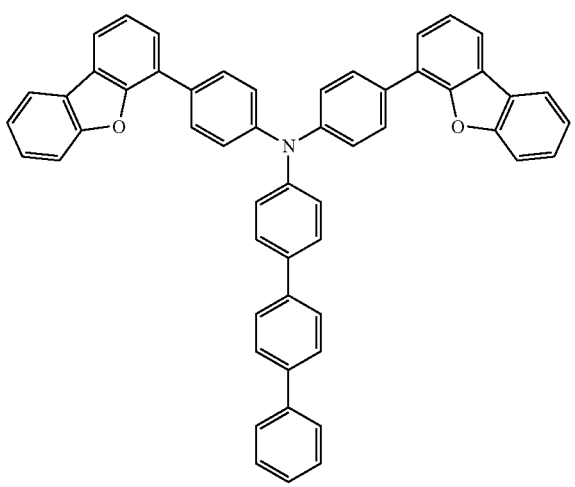

Comparative compound 3

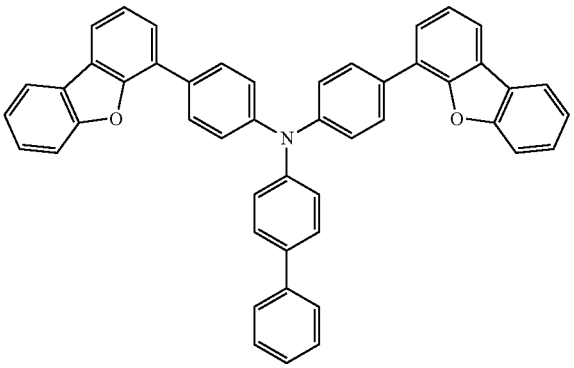

Comparative compound 4

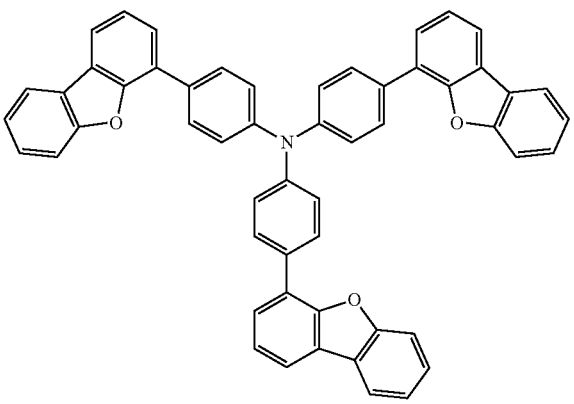

TABLE 1

| | Results of measurements | | | |
|---|---|---|---|---|
| | Second hole transporting material | Emission efficiency (cd/A) @10 mA/cm² | Driving voltage (V) @10 mA/cm² | 80% Lifetime (h) |
| Examples | | | | |
| 1 | H1 | 9.2 | 4.1 | 600 |
| 2 | H2 | 9.1 | 4.1 | 500 |
| 3 | H3 | 9.2 | 4.2 | 550 |
| 4 | H4 | 9.5 | 4.3 | 480 |
| 5 | H5 | 9.4 | 4.3 | 450 |
| Comparative Examples | | | | |
| 1 | Comparative compound 1 | 7.4 | 4.2 | 320 |
| 2 | Comparative compound 2 | 7.7 | 4.1 | 600 |
| 3 | Comparative compound 3 | 7.6 | 4.2 | 500 |
| 4 | Comparative compound 4 | 7.5 | 4.1 | 600 |

Upon comparing Examples 1 to 5 with Comparative Example 1, it can be seen that the device which employs the aromatic amine derivative including a dibenzofuranyl group of the invention has a longer device life. As compared with Comparative Example 1 using the comparative compound 1 in which the substituents are bonded only via p-phenylene groups, the device which employs the aromatic amine derivatives of the invention having a substituent bonded via a m-phenylene group has a higher efficiency.

Upon comparing Examples 1 to 5 with Comparative Examples 2 to 4, it can be seen that the device which employs the aromatic amine derivative of the invention having a substituent bonded via a m-phenylene group has a higher efficiency.

From the above, it can be seen that an organic EL device having a prolonged lifetime and a higher efficiency is obtained by using the aromatic amine derivative of the invention which is characterized by the molecular structure in which both (i) a dibenzofuranyl group and (ii) a substituent bonded via a m-phenylene are present in the same molecular.

The comparison between Examples 1 to 3 and Examples 4 and 5 shows that the aromatic amine derivative represented by formula (9) prolongs the lifetime of an organic EL device and the aromatic amine derivative represented by formula (10) improves the emission efficiency.

INDUSTRIAL APPLICABILITY

As described above in detail, by using the aromatic amine derivative of the invention in the organic thin film layer, an organic EL device having a high efficiency and a long lifetime is obtained. Such an organic EL device is extremely useful as a device with high practical value.

REFERENCE NUMERALS

1: Organic electroluminescence device
2: Substrate
3: Anode
4: Cathode
5: Light emitting layer
6: Hole transporting layer
7: Electron transporting layer
10: Emission unit

What is claimed is:
1. An aromatic amine derivative represented by formula (1):

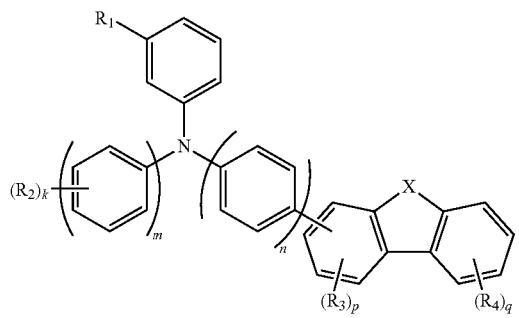

(1)

wherein:
R$_1$ represents a substituted or unsubstituted heteroaryl group having 5 to 30 ring atoms;
each R$_2$ independently represents a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted haloalkyl group having 1 to 30 carbon atoms, a substituted or unsubstituted cycloalkyl group having 3 to 30 ring carbon atoms, a substituted or unsubstituted silyl group, a cyano group, a substituted or unsubstituted alkoxy group having 1 to 30 carbon atoms, a substituted or unsubstituted aryloxy group having 6 to 30 ring carbon atoms, a substituted or unsubstituted aralkyl group having 7 to 30 carbon atoms, a halogen atom, or a substituted carbonyl group, and when k is 2 or more, the groups R$_2$ on adjacent ring carbon atoms may be bonded to each other to form a hydrocarbon ring;

each of R$_3$ and R$_4$ independently represents a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted haloalkyl group having 1 to 30 carbon atoms, a substituted or unsubstituted cycloalkyl group having 3 to 30 ring carbon atoms, a substituted or unsubstituted silyl group, a cyano group, a substituted or unsubstituted alkoxy group having 1 to 30 carbon atoms, a substituted or unsubstituted aryloxy group having 6 to 30 ring carbon atoms, a substituted or unsubstituted aralkyl group having 7 to 30 carbon atoms, a halogen atom, or a substituted carbonyl group, when p is 2 or more, the groups R$_3$ on adjacent ring carbon atoms may be bonded to each other to form a hydrocarbon ring, and when q is 2 or more, the groups R$_4$ on adjacent ring carbon atoms may be bonded to each other to form a hydrocarbon ring;

X represents an oxygen atom or a sulfur atom;
k represents an integer of 0 to 5;
m represents an integer of 1 to 2;
n represents an integer of 1 to 2;
p represents an integer of 0 to 3; and
q represents an integer of 0 to 4.

2. The aromatic amine derivative according to claim 1, wherein the aromatic amine derivative is represented by formula (2):

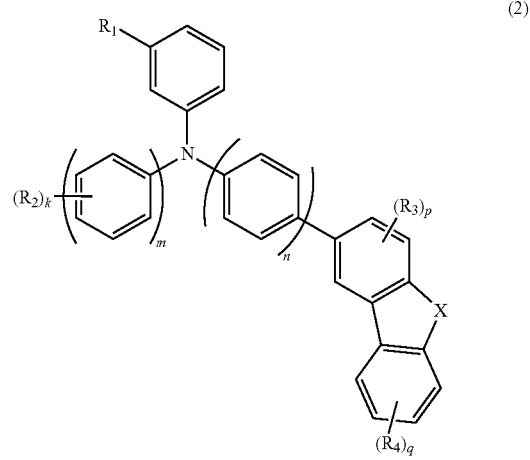

(2)

wherein R$_1$, R$_2$, R$_3$, R$_4$, X, k, m, n, p, and q are as defined above.

3. The aromatic amine derivative according to claim 2, wherein the aromatic amine derivative is represented by formula (3):

(3)

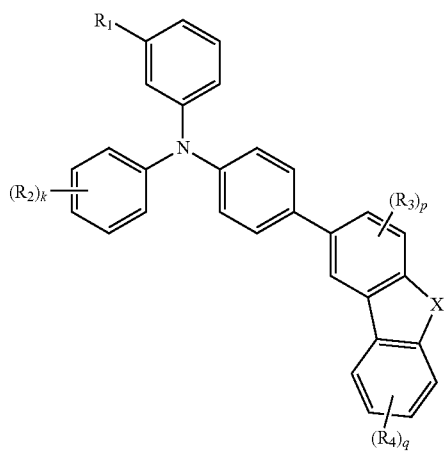

wherein R₁, R₂, R₃, R₄, X, k, p, and q are as defined above.

4. The aromatic amine derivative according to claim 1, wherein the aromatic amine derivative is represented by formula (4):

(4)

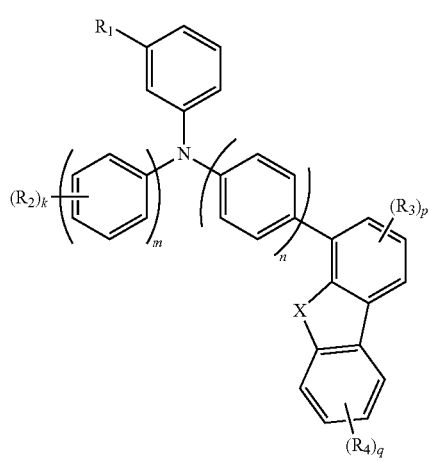

wherein R₁, R₂, R₃, R₄, X, k, m, n, p, and q are as defined above.

5. The aromatic amine derivative according to claim 4, wherein the aromatic amine derivative is represented by formula (5):

(5)

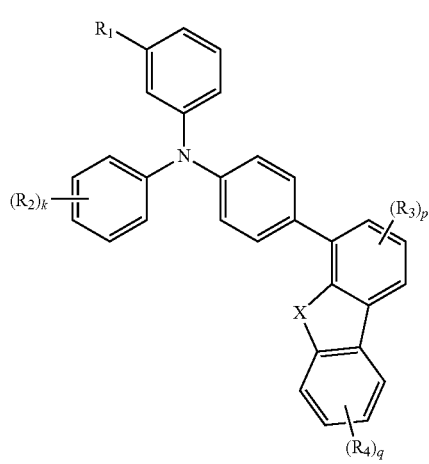

wherein R₁, R₂, R₃, R₄, X, k, p, and q are as defined above.

6. The aromatic amine derivative according to claim 1, wherein the aromatic amine derivative is represented by formula (6):

(6)

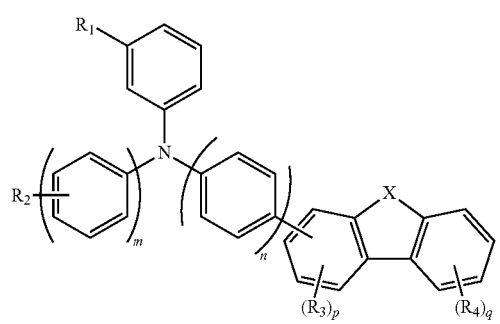

wherein R₁, R₂, R₃, R₄, X, m, n, p, and q are as defined above.

7. The aromatic amine derivative according to claim 3, wherein the aromatic amine derivative is represented by formula (7):

(7)

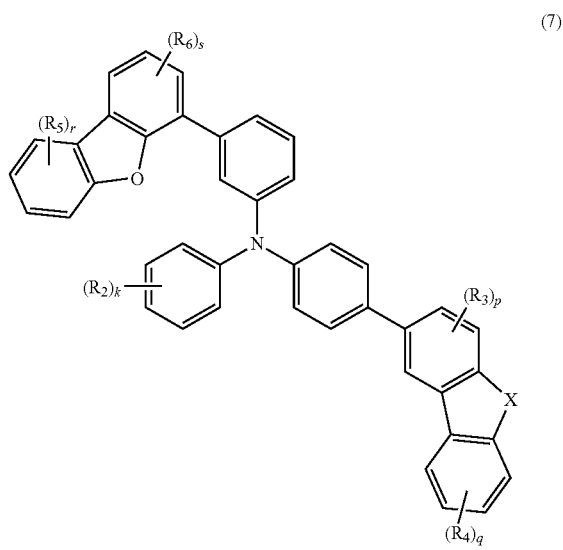

wherein:

R₂, R₃, R₄, X, k, p, and q are as defined above;

each of R₅ and R₆ independently represents a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted haloalkyl group having 1 to 30 carbon atoms, a substituted or unsubstituted cycloalkyl group having 3 to 30 ring carbon atoms, a substituted or unsubstituted silyl group, a cyano group, a substituted or unsubstituted alkoxy group having 1 to 30 carbon atoms, a substituted or unsubstituted aryloxy group having 6 to 30 ring carbon atoms, a substituted or unsubstituted aralkyl group having 7 to 30 carbon atoms, a halogen atom, or a substituted carbonyl group, when r is 2 or more, the groups R₅ on adjacent ring carbon atoms may be bonded to each other to form a hydrocarbon ring, and when s is 2 or more, the groups $R_6$ on adjacent ring carbon atoms may be bonded to each other to form a hydrocarbon ring;

r represents an integer of 0 to 4; and s represents an integer of 0 to 3.

8. The aromatic amine derivative according to claim 5, wherein the aromatic amine derivative is represented by formula (8):

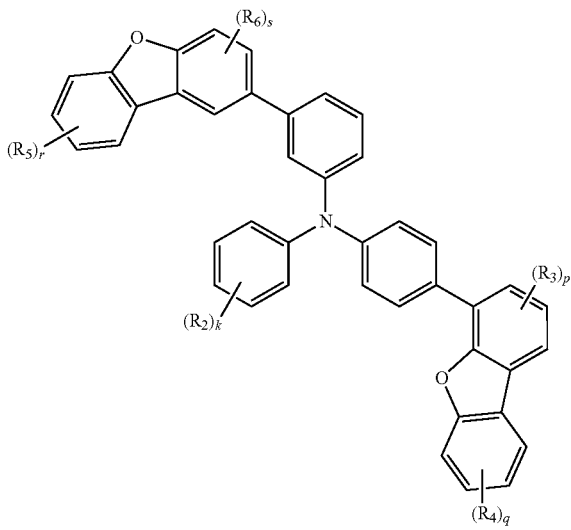

(8)

wherein $R_2$, $R_3$, $R_4$, $R_5$, $R_6$, X, k, p, q, r, and s are as defined above.

9. The aromatic amine derivative according to claim 1, wherein $R_1$ in formulae (1) to (6) is represented by any one of formulae (11-1) to (11-4):

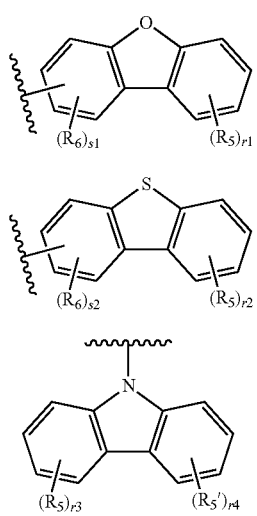

(11-1)

(11-2)

(11-3)

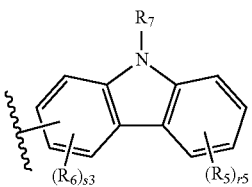

(11-4)

wherein:
each of $R_5$, $R_5'$ and $R_6$ independently represents a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted haloalkyl group having 1 to 30 carbon atoms, a substituted or unsubstituted cycloalkyl group having 3 to 30 ring carbon atoms, a substituted or unsubstituted silyl group, a cyano group, a substituted or unsubstituted alkoxy group having 1 to 30 carbon atoms, a substituted or unsubstituted aryloxy group having 6 to 30 ring carbon atoms, a substituted or unsubstituted aralkyl group having 7 to 30 carbon atoms, a halogen atom, or a substituted carbonyl group;

when each of r1 to r5 is 2 or more, the groups $R_5$ or the groups $R_5'$ on adjacent ring carbon atoms may be bonded to each other to form a hydrocarbon ring, and when each of s1 to s3 is 2 or more, the groups $R_6$ on adjacent ring carbon atoms may be bonded to each other to form a hydrocarbon ring;

$R_7$ represents a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted haloalkyl group having 1 to 30 carbon atoms, a substituted or unsubstituted cycloalkyl group having 3 to 30 ring carbon atoms, or a substituted or unsubstituted aralkyl group having 7 to 30 carbon atoms;

each of r1 to r5 independently represents an integer of 0 to 4; and each of s1 to s3 independently represents an integer of 0 to 3.

10. The aromatic amine derivative according to claim 1, wherein the aromatic amine derivative is a material for an organic electroluminescence device.

11. The aromatic amine derivative according to claim 1, wherein the aromatic amine derivative is a hole injecting material or a hole transporting material for an organic electroluminescence device.

12. An organic electroluminescence device which comprises a cathode, an anode, and an organic thin film layer comprising one or more layers between the cathode and the anode, wherein the organic thin film layer comprises a light emitting layer, and at least one layer of the organic thin film layer comprises the aromatic amine derivative according to claim 1 singly or in combination.

13. The organic electroluminescence device according to claim 12, wherein the organic thin film layer comprises a hole transporting layer and the hole transporting layer comprises the aromatic amine derivative.

* * * * *